(12) United States Patent
Baynes et al.

(10) Patent No.: US 9,102,961 B2
(45) Date of Patent: Aug. 11, 2015

(54) BIOLOGICAL SYNTHESIS OF DIFUNCTIONAL HEXANES AND PENTANES FROM CARBOHYDRATE FEEDSTOCKS

(71) Applicant: Celexion, LLC, Cambridge, MA (US)

(72) Inventors: Brian M. Baynes, Cambridge, MA (US); John Michael Geremia, Somverville, MA (US); Shaun M. Lippow, San Francisco, CA (US)

(73) Assignee: Celexion, LLC, Cambridge, MA (US)

( * ) Notice: Subject to any disclaimer, the term of this patent is extended or adjusted under 35 U.S.C. 154(b) by 0 days.

(21) Appl. No.: 14/248,672

(22) Filed: Apr. 9, 2014

(65) Prior Publication Data

US 2014/0212934 A1    Jul. 31, 2014

Related U.S. Application Data

(62) Division of application No. 13/616,157, filed on Sep. 14, 2012, now Pat. No. 8,722,385, which is a division of application No. 12/661,125, filed on Mar. 11, 2010, now Pat. No. 8,404,465.

(60) Provisional application No. 61/209,917, filed on Mar. 11, 2009.

(51) Int. Cl.
| | | |
|---|---|---|
| *C12P 13/00* | (2006.01) | |
| *C12P 7/62* | (2006.01) | |
| *C12N 9/00* | (2006.01) | |
| *C12N 15/00* | (2006.01) | |
| *C07H 21/04* | (2006.01) | |
| *C12N 15/52* | (2006.01) | |
| *C12N 15/63* | (2006.01) | |

(52) U.S. Cl.
CPC ............... *C12P 13/001* (2013.01); *C12N 15/52* (2013.01); *C12N 15/63* (2013.01); *C12P 13/005* (2013.01)

(58) Field of Classification Search
None
See application file for complete search history.

(56) References Cited

U.S. PATENT DOCUMENTS

| | | |
|---|---|---|
| 3,485,821 A | 12/1969 | Sheehan |
| 4,400,468 A | 8/1983 | Faber |
| 4,683,195 A | 7/1987 | Mullis |
| 4,725,542 A | 2/1988 | Barer |
| 4,730,040 A | 3/1988 | Vagt et al. |
| 4,929,396 A | 5/1990 | Barer |
| 5,221,800 A | 6/1993 | Park |
| 5,258,292 A | 11/1993 | Yeh |
| 5,272,073 A | 12/1993 | Frost |
| 5,487,987 A | 1/1996 | Frost |
| 5,616,496 A | 4/1997 | Frost |
| 5,629,190 A | 5/1997 | Petre |
| 5,994,478 A | 11/1999 | Asrar |
| 6,180,388 B1 | 1/2001 | Crouzet |
| 6,365,376 B1 | 4/2002 | Brzostowicz |
| 6,498,242 B1 | 12/2002 | Cheng |
| 6,794,165 B2 | 9/2004 | Cheng |
| 7,189,543 B2 | 3/2007 | Nishi |
| 7,323,320 B2 | 1/2008 | Oleinikov |
| 7,439,050 B2 | 10/2008 | Pompejus |
| 7,491,520 B2 | 2/2009 | Raemakers-franken et al. |
| 7,563,600 B2 | 7/2009 | Oleinikov |
| 2002/0127666 A1 | 9/2002 | Brzostowicz |
| 2003/0087403 A1 | 5/2003 | Cheng |
| 2004/0053382 A1 | 3/2004 | Senkpeil |
| 2006/0084152 A1 | 4/2006 | Pompejus |
| 2006/0160138 A1 | 7/2006 | Church |
| 2007/0117183 A1 | 5/2007 | Pompejus |
| 2007/0117191 A1 | 5/2007 | Kamachi |
| 2007/0269870 A1 | 11/2007 | Church |
| 2008/0064610 A1 | 3/2008 | Lipovsek |
| 2008/0287320 A1 | 11/2008 | Baynes |
| 2009/0087840 A1 | 4/2009 | Baynes |
| 2009/0246838 A1 | 10/2009 | Zelder |

FOREIGN PATENT DOCUMENTS

| | | |
|---|---|---|
| JP | 2002/223770 | 8/2008 |
| WO | WO 95/07996 | 3/1995 |
| WO | WO 01/66573 | 9/2001 |
| WO | WO 03/106691 | 12/2003 |
| WO | WO 2004/013341 | 2/2004 |
| WO | WO 2005/068643 | 7/2005 |
| WO | WO 2007/099029 | 9/2007 |
| WO | WO 2007/101867 | 9/2007 |
| WO | WO 2008/092720 | 9/2008 |
| WO | WO 2008/127283 | 10/2008 |
| WO | WO 2009/046375 | 4/2009 |
| WO | WO 2009/113853 | 9/2009 |
| WO | WO 2009/113855 | 9/2009 |
| WO | WO 2009/133114 | 11/2009 |
| WO | WO 2009/151728 | 12/2009 |
| WO | WO 2010/068944 | 6/2010 |
| WO | WO 2010/129936 | 11/2010 |

OTHER PUBLICATIONS

Andi B. et al. "Stabilization and characterization of histidine-tagged homocitrate synthase from *Saccharomyces cerevisiae*." Archives of Biochemistry and Biophysics (2004), 421 (2): 243-254.

(Continued)

*Primary Examiner* — Christian Fronda

(74) *Attorney, Agent, or Firm* — Greenberg Traurig, LLP; Natalie Salem

(57) ABSTRACT

Provided herein are methods for the production of difunctional alkanes in microorganisms. Also provided are enzymes and nucleic acids encoding such enzymes, associated with the difunctional alkane production from carbohydrates feedstocks in microorganisms. The invention also provides recombinant microorganisms and metabolic pathways for the production of difunctional alkanes.

20 Claims, 10 Drawing Sheets

(56) References Cited

OTHER PUBLICATIONS

Atsumi, Shota et al., "Non-fermentative pathways for synthesis of branched-chain higher alcohols as biofuels" Nature, vol. 451, pp. 86-90, 2008.
Caspi, Ron, et al., "The MetaCyc database of metabolic pathways and enzymes and the BioCyc collection of pathways/genome database" Nucleic Acids Research, vol. 36, D623-D631, 2008.
Chica et al. "Semi-rational approaches to engineering enzyme activity: combining the benefits of directed evolution and rational design" Curr. Opin. Biotechnol. 16(4): 378-384.
de la Plaza M. et al. "Biochemical and molecular characterization of—ketoisovalerate decarboxylase, an enzyme involved in the formation of aldehydes from amino acids by *Lactococcus lactis*" FEMS Microbiology Letters 238, pp. 367-374, 2004.
De Las Rivas B. et al. "Gene cloning, expression, and functional characterization of an ornithine decarboxylase protein from *Serratia liquefaciens* IFI65" J. Microbiol. Biotechnol., 17(3), pp. 408-413, 2007.
Donoghue and Trudgill "The metabolism of cyclohexanol by Acinetobacter NCIB 9871." Eur J Biochem. 1975, vol. 60, No. 1, pp. 1-7.
Drevland et al., "Methanogen Homoaconitase Catalyzes Both Hydrolyase Reactions in Coenzyme B Biosynthesis", Journal of Biological Chemistry, vol. 283, pp. 28888-28896, 2008.
Fotheringham Ian, "Engineering biosynthetic pathways: new routes for chiral amino acids" Current opinion in Biology, vol. 4, pp. 120-124, 2000.
Fujii T. et al., "Cloning and characterization of pcd encoding delta'-piperideine-6-carboxylate dehydrogenase from flavobacterium lutescens 1F03084." J. Biochem. 2000, 128(3):391-7.
Goh D.L. M. et al. "Characterization of the human gene encoding α-aminoadipate aminotransferase (AADAT)" Molecular Genetics and Metabolism, 76, pp. 172-180, 2002.
Goodlove et al., "Cloning and sequence analysis of the fermentative alcohol-dehydrogenase-encoding gene of *Escherichia coli*.", Gene, 1989, vol. 85, No. 1, pp. 209-214.
Howell et al., "Alpha-keto acid chain elongation reactions involved in the biosynthesis of coenzyme B (7-mercaptoheptanoyl threonine phosphate) in methanogenic Archaea", Biochemistry, 1998, vol. 37, No. 28, pp. 1010810117.
Howell et al., "Identification of Enzymes Homologous to Isocitrate Dehydrogenase That Are Involved in Coenzyme B and Leucine Biosynthesis in Methanoarchaea", J. Bacteriol., 2000, vol. 182, No. 17, pp. 5013C35016.
Hudson et al. "An LL-Diaminopimelate Aminotransferase Defines a Novel Variant of the Lysine Biosynthesis Pathway in Plants" Plant Physiol. 140(1) 292-301, 2006.
Iwaki et al. "Identification of a Transcriptional Activator (ChnR) and a 6-Oxohexanoate Dehydrogenase (ChnE) in the Cyclohexanol Catabolic Pathway in Acinetobacter sp. Strain NCIMB 9871 and Localization of the Genes That Encode Them" Applied and Environmental Microbiology, 1999, p. 5158-5162, vol. 65, No. 11.
Jia Y et al. "Kinetics and product analysis of the reaction catalysed by recombinant homoaconitase from Thermus thermophilus." Biochem J. (2006) 396(3):479-85.
Jones Prather, Kristala L., et al., "*De novo* biosynthetic pathways: rational design of microbial chemical factories" Current Opinion in Biotechnology, vol. 19, pp. 468-474, 2008.
Kim et al. "Characterization of (R)-2-Hydroxyisocaproate Dehydrogenase and a Family III Coenzyme A Transferase Involved in Reduction of L-Leucine to Isocaproate by Clostridium difficile" Applied and Environmental Microbiology, 2006, vol. 72, pp. 6062-6069.
Kingsbury J.M. et al. "Novel chimeric spermidine synthase-saccharopine dehydrogenase gene (SPE3-LYS9) in the human pathogen *Cryptococcus neoformans*" Eukaryotic Cell, 3(3), pp. 752-763, 2004.
Lin Y. et al. "Complete kinetic mechanism of homoisocitrate dehydrogenase from *Saccharomyces cerevisiae*." Biochemistry (2007) 46 (3): 890-898.
Miyazaki T. et al. "alpha-Aminoadipate aminotransferase from an extremely thermophilic bacterium, Thermus thermophilus" 2004, Microbiology, 150:2327-2334.
Niu, Wei et al., "Benzene-free synthesis of adipic acid" Biotechnol. Prog., vol. 18, pp. 201-211, 2002.
Sen et al. "Developments in Directed Evolution for Improving Enzyme Functions", Appl. Biochem. Biotechnol. 143(3): 212-223, 2007.
Tanaka et al., "Metabolism of cyclohexanol by Pseudomonas sp." Hakko Kagaku Kaishi (1977), 55(2), 62-7.
Tsujimoto et al. "L-Lysine biosynthetic pathway of Methylophilus methylotrophus and construction of an L-Lysine producer" J. Biotechnol. 2006 124(2):327-337.
Yan H. et al. "Cloning, sequencing and characterization of the α-aminoadipate reductase gene (LYS2) from *Saccharomycopsis fibuligera*" Yeast, 24, pp. 189-199, 2007.
Zhang et al., "Expanding metabolism for synthesis of nonnatural alcohols" P.N.A.S, 2008, vol. 105, No. 52, pp. 20653-20658.
Zheng. et al. "Purification of the Azotobacter vinelandii nifV-encoded homocitrate synthase". J. Bacteriol., 1997, vol. 179, No. 18, pp. 5963-5966.
Communication Relating to the Results of the Partial International Search for International Application No. PCT/US2012/021274 dated Apr. 24, 2013.
International Search Report for PCT/US2012/051274 mailed Jul. 19, 2013.

BIOLOGICAL SYNTHESIS OF DIFUNCTIONAL HEXANES AND PENTANES FROM CARBOHYDRATE FEEDSTOCKS

RELATED APPLICATIONS

This application is a divisional of U.S. patent application Ser. No. 13/616,157, filed Sep. 14, 2012, now U.S. Pat. No. 8,722,385, which is a divisional of U.S. patent application Ser. No. 12/661,125, filed Mar. 11, 2010, now U.S. Pat. No. 8,404,465 which claims priority to and the benefit of U.S. Provisional Application No. 61/209,917, filed Mar. 11, 2009, the disclosure of all of which are incorporated herein by reference in their entirety.

FIELD OF INVENTION

Aspects of the invention relate to methods for the production of difunctional alkanes in microorganisms. In particular, aspects of the invention describe enzymes, and nucleic acids encoding such enzymes, associated with the difunctional alkane production from carbohydrates feedstocks in microorganisms. More specifically, aspects of the invention describe recombinant microorganisms and metabolic pathways for the production of adipic acid, aminocaproic acid, hexamethylenediamine, 6-hydroxyhexanoate and 6-hydroxyhexanamine and 1,6-hexanediol, 5-aminopentanol, 5-aminopentanoate, 1,5-pentanediol, glutarate and 5-hydroxypentanoate.

BACKGROUND

Crude oil is the number one starting material for the synthesis of key organic chemicals and polymers. As oil becomes increasingly scarce and expensive, biological processing of renewable raw materials in the production of chemicals using live microorganisms or their purified enzymes becomes increasingly interesting. Biological processing, in particular, fermentations have been used for centuries to make beverages. Over the last 50 years, microorganisms have been used commercially to make compounds such as antibiotics, vitamins, and amino acids. However, the use of microorganisms for making industrial chemicals has been much less widespread. It has been realized only recently that microorganisms may be able to provide an economical route to certain compounds that are difficult or costly to make by conventional chemical means.

SUMMARY OF THE INVENTION

In one aspect, the invention provides a microorganism producing 6-aminocaproic acid from lysine, and the microorganism includes at least one nucleic acid encoding a polypeptide that catalyzes a substrate to product conversion such as:
  i) lysine to beta-lysine,
  ii) beta-lysine to 6-amino-3-oxohexanoic acid,
  iii) 6-amino-3-oxohexanoic acid to 6-amino-3-hydroxyhexanoic acid,
  iv) 6-amino-3-hydroxyhexanoic acid to 6-aminohex-2-enoic acid, or
  v) 6-aminohex-2-enoic acid to 6-aminocaproic acid.

In some embodiments, the nucleic acid molecule is heterologous to the recombinant microorganism.

In other embodiments, the microorganism also includes a nucleic acid encoding a polypeptide that catalyzes a substrate to product conversion such as:
  i) 6-amino-3-hydroxyhexanoic acid to 6-amino-3-hydroxyhexanoyl-CoA,
  ii) 6-amino-3-hydroxyhexanoyl-CoA to 6-aminohex-2-enoyl-CoA, or
  iii) 6-aminohex-2-enoyl-CoA to 6-aminohex-2-enoic acid.

In other embodiments, the microorganism also includes a nucleic acid encoding a polypeptide that catalyzes a substrate to product conversion such as:
  i) 6-amino-3-hydroxyhexanoyl-CoA to 6-aminohexanoyl-CoA or
  ii) 6-aminohexanoyl-CoA to 6-aminocaproic acid.

In a second aspect, the invention provides in part a recombinant microorganism producing 6-aminocaproic acid from lysine, and the recombinant microorganism includes at least one nucleic acid encoding a polypeptide that catalyzes a substrate to product conversion such as:
  i) lysine to beta-lysine,
  ii) beta-lysine to 3,6-diaminohexanoyl-CoA,
  iii) 3,6-diaminohexanoyl-CoA to 6-aminohex-2-enoyl-CoA,
  iv) 6-aminohex-2-enoyl-CoA to 6-aminohex-2-enoic acid, or
  v) 6-aminohex-2-enoic acid to 6-aminocaproic acid. The at least one nucleic acid molecule is generally heterologous to the recombinant microorganism.

In another aspect, the invention provides a recombinant microorganism producing 6-aminocaproic acid from lysine, the recombinant microorganism includes at least one nucleic acid encoding a polypeptide that catalyzes a substrate to product conversion that includes:
  i) lysine to beta-lysine,
  ii) beta-lysine to 3,6-diaminohexanoyl-CoA,
  iii) 3,6-diaminohexanoyl-CoA to 6-aminohex-2-enoyl-CoA,
  iv) 6-aminohex-2-enoyl-CoA to 6-aminohexanoyl-CoA, or
  v) 6-aminohexanoyl-CoA to 6-aminocaproic acid.

In a further aspect, provided is a recombinant microorganism producing 6-aminocaproic acid from lysine, where the recombinant microorganism includes at least one nucleic acid encoding a polypeptide that catalyzes a substrate to product conversion such as:
  i) lysine to beta-lysine,
  ii) beta-lysine to 6-aminohex-2-enoic acid, or
  iii) 6-aminohex-2-enoic acid to 6-aminocaproic acid.

In certain embodiments, the at least one nucleic acid molecule is heterologous to the recombinant microorganism.

In a further aspect, provided is a recombinant microorganism producing 6-aminocaproic acid from lysine, where the recombinant microorganism includes at least one nucleic acid encoding a polypeptide that catalyzes a substrate to product conversion such as:
  i) lysine to 6-amino-2-oxohexanoic acid,
  ii) 6-amino-2-oxohexanoic acid to 6-amino-2-hydroxyhexanoic acid,
  iii) 6-amino-2-hydroxyhexanoic acid to 6-aminohex-2-enoic acid, or
  iv) 6-aminohex-2-enoic acid to 6-aminocaproic acid.

In certain embodiments, the recombinant microorganism also includes at least one nucleic acid encoding a polypeptide that catalyzes a substrate to product conversion such as:
  i) 6-amino-2-hydroxyhexanoic to 6-amino-2-hydroxyhexanoyl-CoA, or ii) 6-amino-2-hydroxyhexanoyl-CoA to 6-aminohex-2-enoyl-CoA.

In certain embodiments, the recombinant microorganism also includes at least one nucleic acid encoding a polypeptide that catalyzes a substrate to product conversion such as:
  i) 6-amino-2-hydroxyhexanoic to 6-amino-2-hydroxyhexanoyl-CoA,
  ii) 6-amino-2-hydroxyhexanoyl-CoA to 6-aminohexanoyl-CoA, or
  iii) 6-aminohexanoyl-CoA to 6-aminocaproic acid.

In another aspect, the invention provides a recombinant microorganism producing 6-aminocaproic acid from L-2,3-dihydrodipicolinate, and the recombinant microorganism includes at least one nucleic acid encoding a polypeptide that catalyzes a substrate to product conversion such as:
  i) L-2,3-dihydrodipicolinate to $\Delta^1$-piperideine-2,6-dicarboxylate,
  ii) $\Delta^1$-piperideine-2,6-dicarboxylate to $\Delta^1$-piperideine-2-carboxylate,
  iii) $\Delta^1$-piperideine-2-carboxylate to L-pipecolate,
  iv) L-pipecolate to 6-amino-2-oxohexanoic acid,
  v) 6-amino-2-oxohexanoic acid to 6-amino-2-hydroxyhexanoic acid,
  vi) 6-amino-2-hydroxyhexanoic acid to 6-aminohex-2-enoic acid, or
  vii) 6-aminohex-2-enoic acid to 6-aminocaproic acid.

In some embodiments the at least one nucleic acid molecule is heterologous to the recombinant microorganism.

In another aspect, provided is a recombinant microorganism producing 6-aminocaproic acid from L-2,3-dihydrodipicolinate, where the recombinant microorganism includes at least one nucleic acid encoding a polypeptide that catalyzes a substrate to product conversion such as:
  i) L-2,3-dihydrodipicolinate to $\Delta^1$-piperideine-2,6-dicarboxylate,
  ii) $\Delta^1$-piperideine-2,6-dicarboxylate to $\Delta^1$-piperideine-2-carboxylate,
  iii) $\Delta^1$-piperideine-2-carboxylate to L-pipecolate,
  iv) L-pipecolate to 6-amino-2-oxohexanoic acid,
  v) 6-amino-2-hydroxyhexanoic to 6-amino-2-hydroxyhexanoyl-CoA,
  vi) 6-amino-2-hydroxyhexanoyl-CoA to 6-aminohex-2-enoyl-CoA,
  vii) 6-aminohex-2-enoyl-CoA to 6-aminohex-2-enoic acid, or
  viii) 6-aminohex-2-enoic acid to 6-aminocaproic acid.

In some embodiments the at least one nucleic acid molecule is heterologous to the recombinant microorganism.

In another aspect, provided is a recombinant microorganism producing 6-aminocaproic acid from L-2,3-dihydrodipicolinate, the recombinant microorganism includes at least one nucleic acid encoding a polypeptide that catalyzes a substrate to product conversion such as:
  i) L-2,3-dihydrodipicolinate to $\Delta^1$-piperideine-2,6-dicarboxylate,
  ii) $\Delta^1$-piperideine-2,6-dicarboxylate to $\Delta^1$-piperideine-2-carboxylate,
  iii) $\Delta^1$-piperideine-2-carboxylate to L-pipecolate,
  iv) L-pipecolate to 6-amino-2-oxohexanoic acid,
  v) 6-amino-2-hydroxyhexanoic to 6-amino-2-hydroxyhexanoyl-CoA,
  vi) 6-amino-2-hydroxyhexanoyl-CoA to 6-aminohex-2-enoyl-CoA,
  vii) 6-aminohex-2-enoyl-CoA to 6-aminohexanoyl-CoA, or
  viii) 6-aminohexanoyl-CoA to 6-aminocaproic acid.

In another aspect, provided is a recombinant microorganism producing 6-aminocaproic acid from L-2,3-dihydrodipicolinate, the recombinant microorganism includes at least one nucleic acid encoding a polypeptide that catalyzes a substrate to product conversion such as:
  i) L-2,3-dihydrodipicolinate to $\Delta^1$-piperideine-2,6-dicarboxylate,
  ii) $\Delta^1$-piperideine-2,6-dicarboxylate to $\Delta^1$-piperideine-2-carboxylate,
  iii) $\Delta^1$-piperideine-2-carboxylate to 6-amino-2-oxohexanoic acid,
  iv) 6-amino-2-oxohexanoic acid to 6-amino-2-hydroxyhexanoic acid,
  v) 6-amino-2-hydroxyhexanoic acid to 6-amino-2-hydroxyhexanoyl-CoA,
  vi) 6-amino-2-hydroxyhexanoyl-CoA to 6-amino-hex-2-enoyl-CoA,
  vii) 6-amino-hex-2-enoyl-CoA to 6-amino-hex-2-enoic acid, or
  viii) 6-amino-hex-2-enoic acid to 6-aminocaproic acid.

In another aspect, provided is a recombinant microorganism producing 6-aminocaproic acid from L-2,3-dihydrodipicolinate, the recombinant microorganism includes at least one nucleic acid encoding a polypeptide that catalyzes a substrate to product conversion such as:
  i) L-2,3-dihydrodipicolinate to $\Delta^1$-piperideine-2,6-dicarboxylate,
  ii) $\Delta^1$-piperideine-2,6-dicarboxylate to 2-amino-6-oxoheptanedioic acid,
  iii) 2-amino-6-oxoheptanedioic acid to 6-amino-2-oxohexanoic acid,
  iv) 6-amino-2-oxohexanoic acid to 6-amino-hex-2-enoic acid, or
  v) 6-amino-hex-2-enoic acid to 6-aminocaproic acid.

In another aspect, provided is a recombinant microorganism producing 6-aminocaproic acid from L-2,3-dihydrodipicolinate, the recombinant microorganism includes at least one nucleic acid encoding a polypeptide that catalyzes a substrate to product conversion such as:
  i) L-2,3-dihydrodipicolinate to 5,6-dihydropyridine-2-carboxylic acid,
  ii) 5,6-dihydropyridine-2-carboxylic acid to 6-amino-2-oxohex-3-enoic acid,
  iii) 6-amino-2-oxohex-3-enoic acid to 6-amino-2-oxohexanoic acid,
  iv) 6-amino-2-oxohexanoic acid to 6-amino-hex-2-enoic acid, or
  v) 6-amino-hex-2-enoic acid to 6-aminocaproic acid.

In another aspect, provided is a recombinant microorganism producing 6-aminocaproic acid from L-lysine, the recombinant microorganism includes at least one nucleic acid encoding a polypeptide that catalyzes a substrate to product conversion such as:
  i) L-lysine to D-lysine,
  ii) D-lysine to D-pipecolate, or
  iii) D-pipecolate to 6-aminocaproic acid.

In another aspect, provided is a recombinant microorganism producing adipic acid from L-2,3-dihydrodipicolinate, the recombinant microorganism includes at least one nucleic acid encoding a polypeptide that catalyzes a substrate to product conversion such as:
  i) L-2,3-dihydrodipicolinate to $\Delta^1$-piperideine-2,6-dicarboxylate,
  ii) $\Delta^1$-piperideine-2,6-dicarboxylate to $\Delta^1$-piperideine-2-carboxylate,
  iii) $\Delta^1$-piperideine-2-carboxylate to L-pipecolate,
  iv) L-pipecolate to $\Delta^1$-piperideine-6-carboxylate, v) $\Delta^1$-piperideine-6-carboxylate to 2-aminoadipate-6-semialdehyde, vi) 2-aminoadipate-6-semialdehyde to 2-aminoadipate, or vii) 2-aminoadipate to adipic acid.

In another aspect, provided is a recombinant microorganism producing adipic acid from L-2,3-dihydrodipicolinate, the recombinant microorganism includes at least one nucleic acid encoding a polypeptide that catalyzes a substrate to product conversion such as:

i) L-2,3-dihydrodipicolinate to $\Delta^1$-piperideine-2,6-dicarboxylate, ii) $\Delta^1$-piperideine-2,6-dicarboxylate to $\Delta^1$-piperideine-2-carboxylate, iii) $\Delta^1$-piperideine-2-carboxylate to L-pipecolate, iv) L-pipecolate to $\Delta^1$-piperideine-6-carboxylate, v) $\Delta^1$-piperideine-6-carboxylate to 2-aminoadipate-6-semialdehyde, vi) 2-aminoadipate-6-semialdehyde to adipate semialdehyde, or vii) adipate semialdehyde to adipic acid.

In another aspect, provided is a recombinant microorganism producing 1,6-hexanediol from L-2,3-dihydrodipicolinate, the recombinant microorganism includes at least one nucleic acid encoding a polypeptide that catalyzes a substrate to product conversion such as:

i) L-2,3-dihydrodipicolinate to $\Delta^1$-piperideine-2,6-dicarboxylate, ii) $\Delta^1$-piperideine-2,6-dicarboxylate to $\Delta^1$-piperideine-2-carboxylate, iii) $\Delta^1$-piperideine-2-carboxylate to L-pipecolate, iv) L-pipecolate to $\Delta^1$-piperideine-6-carboxylate, v) $\Delta^1$-piperideine-6-carboxylate to 2-aminoadipate-6-semialdehyde, vi) 2-aminoadipate-6-semialdehyde to adipate semialdehyde, or vii) adipate semialdehyde to 1,6-hexanediol.

In another aspect, provided is a recombinant microorganism producing 6-hydroxyhexanoate from L-2,3-dihydrodipicolinate, the recombinant microorganism includes at least one nucleic acid encoding a polypeptide that catalyzes a substrate to product conversion such as:

i) L-2,3-dihydrodipicolinate to $\Delta^1$-piperideine-2,6-dicarboxylate, ii) $\Delta^1$-piperideine-2,6-dicarboxylate to $\Delta^1$-piperideine-2-carboxylate, iii) $\Delta^1$-piperideine-2-carboxylate to L-pipecolate, iv) L-pipecolate to $\Delta^1$-piperideine-6-carboxylate, v) $\Delta^1$-piperideine-6-carboxylate to 2-aminoadipate-6-semialdehyde, vi) 2-aminoadipate-6-semialdehyde to adipate semialdehyde, or vii) adipate semialdehyde to 6-hydroxyhexanoate.

In another aspect, provided is a recombinant microorganism producing 6-aminocaproic acid from lysine, the recombinant microorganism includes at least one nucleic acid encoding a polypeptide that catalyzes a substrate to product conversion such as:

i) lysine to 6-amino-2-oxohexanoic acid, ii) 6-amino-2-oxohexanoic acid to 7-amino-2-oxoheptanoic acid, iii) 7-amino-2-oxoheptanoic acid to 6-aminohexanal, or iv) 6-aminohexanal to 6-aminocaproic acid.

In another aspect, provided is a recombinant microorganism producing 6-aminocaproic acid from lysine, the recombinant microorganism includes at least one nucleic acid encoding a polypeptide that catalyzes a substrate to product conversion such as:

i) lysine to 2,7-diaminoheptanoic acid, ii) 2,7-diaminoheptanoic acid to 7-amino-2-oxoheptanoic acid, iii) 7-amino-2-oxoheptanoic acid to 6-aminohexanal, or iv) 6-aminohexanal to 6-aminocaproic acid.

In another aspect, provided is a recombinant microorganism producing 6-aminocaproic acid from lysine, the recombinant microorganism includes at least one nucleic acid encoding a polypeptide that catalyzes a substrate to product conversion such as:

i) lysine to 2,7-diaminoheptanoic acid, ii) 2,7-diaminoheptanoic acid to 7-amino-2-oxoheptanoic acid, iii) 7-amino-2-oxoheptanoic acid to 6-aminohexanamide, or iv) 6-aminohexanamide to 6-aminocaproic acid.

In another aspect, provided is a recombinant microorganism producing hexamethylenediamine from lysine, the recombinant microorganism includes at least one nucleic acid encoding a polypeptide that catalyzes a substrate to product conversion such as:

i) lysine to 2,7-diaminoheptanoic acid, or ii) 2,7-diaminoheptanoic acid to hexamethylenediamine.

In certain embodiments, the recombinant microorganisms described herein are bacterial or yeast cells.

In further embodiments, one or more of the nucleic acids described herein encodes an enzyme. For example, the enzyme exists in a natural biological system or, alternatively, the enzyme does not exist in a natural biological system.

In still further embodiments, the nucleic acids encode a plurality of enzymes and the plurality of enzymes do not exist together in a natural biological system.

Also provided are nucleic acid preparations that encode at least one polypeptide that catalyzes a substrate to product conversion described herein. In some embodiments, the nucleic acids include plasmids or other vector molecules.

Also provided are nucleic acid preparations containing one or more nucleic acid molecules that are engineered nucleic acids, and these engineered nucleic acids have less than 99%, less than 95%, less than 90%, less than 80%, less than 70%, or less than 60% identity with a natural nucleic acid. Nucleic acid preparations are provided that encode one or more proteins, which have less than 99%, less than 95%, less than 90%, less than 80%, less than 70%, or less than 60% identity with a natural protein.

In another aspect, provided are engineered metabolic pathways for the production of 6-aminocaproic acid in a recombinant microorganism, which include a plurality of polypeptides that catalyze the substrate to product conversions described herein. In some embodiments, the plurality of polypeptides does not exist in a natural biological system.

In another aspect, provided is an engineered metabolic pathway for the production of adipic acid in a recombinant microorganism, which includes a plurality of polypeptides that catalyze the substrate to product conversions described herein. In some embodiments, the plurality of polypeptides does not exist in a natural biological system.

In a further aspect, provided is an engineered metabolic pathway for the production of 1,6-hexanediol in a recombinant microorganism includes a plurality of polypeptides that catalyze one or more of the substrate to product conversions described herein. In some embodiments, the plurality of polypeptides does not exist in a natural biological system.

In another aspect, provided is an engineered metabolic pathway for the production of 6-hydroxyhexanoate in a recombinant microorganism that includes a plurality of polypeptides that catalyze a substrate to product conversion described herein.

In another aspect, provided is an engineered metabolic pathway for the production of hexamethylenediamine in a recombinant microorganism that includes a plurality of polypeptides that catalyze the substrate to product conversion described herein.

BRIEF DESCRIPTION OF THE DRAWINGS

The invention can be more fully understood from the following detailed description and the figures which form part of the application

DETAILED DESCRIPTION OF THE INVENTION

Figure 1:
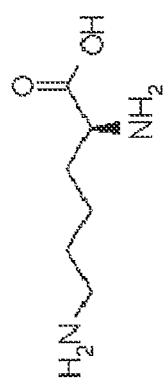
FIG. 1 shows the structure of L-lysine

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The terms "comprise" and "comprising" are used in the inclusive, open sense, meaning that additional elements may be included.

The term "including" is used to mean "including but not limited to". "Including" and "including but not limited to" are used interchangeably.

All publications mentioned herein are incorporated herein by reference. The publications discussed herein are provided solely for their disclosure prior to the filing date of the present invention. Nothing herein is to be construed as an admission that the present invention is not entitled to antedate such publication by virtue of prior invention.

Aspects of the invention provide methods and materials for producing organic aliphatic compounds of interest in a rapid, inexpensive and environmentally responsible way. As such, the present invention meets a number of commercial and industrial needs. The term "organic molecule" refers, for example, to any molecule that is made up predominantly of carbon and hydrogen, such as, for example, alkanes. Organic compounds of interest, such as difunctional alkanes, diols, dicarboxylic acids, etc. can be used to synthesize plastic, nylons and other products usually derived from petroleum and hydrocarbons. Aspects of the invention relate to the synthesis of difunctional n-alkanes with hydrocarbon chains derived from a hydrocarbon chain $C_n$ wherein n is a number of from about 1 to about 8, such as from about 2 to about 5, from about 3 to about 4, or preferably from 5 to 6. In a preferred embodiment, the difunctional n-alkanes are derived from lysine, lysine precursors and/or lysine degradation compounds.

Aspects of the invention relate to the production of difunctional alkanes of interest in a microorganism and provide methods for the production of difunctional alkanes from a carbohydrate source in a microorganism. As used herein "difunctional alkanes" refers to alkanes having two functional groups. The term "functional group" refers, for example, to a group of atoms arranged in a way that determines the chemical properties of the group and the molecule to which it is attached. Examples of functional groups include halogen atoms, hydroxyl groups (—OH), carboxylic acid groups (—COOH) and amine groups (—NH$_2$) and the like. "Alcohol" refers, for example, to an alkyl moiety in which one or more of the hydrogen atoms has been replaced by an —OH group. The term "primary alcohol" refers, for example to alcohols in which the —OH group is bonded to a terminal or chain-ending carbon atom, such as in 1-hexanol and the like. The term "secondary alcohol" refers, for example to alcohols in which the —OH group is bonded to a carbon atom that is bonded to one hydrogen atom and to two other carbon atoms, such as in 2-hexanol and the like. The term "tertiary alcohol" refers, for example to alcohols in which the —OH group is bonded to a carbon atom that is bonded to three other carbon atoms. "Amine" refers, for example, to an alkyl moiety in which one or more of the hydrogen atoms has been replaced by an —NH$_2$ group. "Carbonyl compound" refers, for example, to an organic compound containing a carbonyl group, C═O, such as, for example, aldehydes, which have the general formula RCOH; ketones, which have the general formula RCOR; carboxylic acids, which have the general formula RCOOH; and esters, which have the general formula RCOOR'.

The method incorporates microorganisms capable of producing one of the following C6-difunctional alkanes of interest, particularly, adipic acid, amino caproic acid, hexamethylenediamine (HMD), or 6-hydroxyhexanoate. Other difunctional alkanes of interest include 5-aminopentanol, 5-aminopentanoate, 1,5-pentanediol, glutarate, 5-hydroxypentanoate, cadaverine, etc. Several chemical synthesis routes have been described, for example, for adipic acid and its intermediates such as muconic acid and adipate semialdehyde; for caprolactam, and its intermediates such as 6-amino caproic acid; for hexane 1,6 diamine or hexanemethylenediamine; but only a few biological routes have been disclosed for some of these organic chemicals. Therefore, aspects of the invention provide engineered metabolic routes, methods to produce difunctional alkanes from sustainable feedstock, and materials associated therewith, including isolated nucleic acids or engineered nucleic acids, polypeptides or engineered polypeptides, and host cells or genetically engineered host cells. Carbon sources suitable as starting materials for such biosynthetic pathways include carbohydrates and synthetic intermediates. Examples of carbohydrates which cells are capable of metabolizing include sugars, dextroses, triglycerides and fatty acids. Intermediate products from metabolic pathway such as pyruvate, oxaloacetate, and 2-ketoglutatrate can also be used as starting materials. Aspects of the invention relate to engineered polypeptides, and polynucleotides encoding such polypeptides, having enzymatic activity or an improved activity for a natural or unnatural substrate or having broad substrate specificity (e.g., catalytic promiscuity such as substrate promiscuity). The terms "polypeptide," "protein" and peptide," which are used interchangeably herein, refer to a polymer of amino acids, including, for example, gene products, naturally-occurring proteins, homologs, orthologs, paralogs, fragments, and other equivalents, variants and analogs of the forgoing. The term "polypeptide having enzymatic activity" refers to any polypeptide that catalyzes a chemical reaction of other substances without itself being destroyed or altered upon completion of the reaction. Typically, a polypeptide having enzymatic activity catalyzes the formation of one or more products from one or more substrates. In some aspects of the invention, the catalytic promiscuity properties of some enzymes may be combined with protein engineering and may be exploited in novel metabolic pathways and biosynthesis applications. In some embodiments, existing enzymes are modified for use in organic biosynthesis. In some preferred embodiments, the enzymes involved in the production of the difunctional n-alkanes of interest include but are not limited to 2 amino-decarboxylases, 2-ketodecarboxylases, terminal-aminotransferases, 2-aminotransferases, 2 amino-aldehyde mutase, alcohol dehydrogenases, aldehyde dehydrogenases, amino-aldehyde dehydrogenases, dehydrogenases, dehydratases, CoA ligases, CoA-S transferases, deaminases and thioestrerases. In some embodiments, the reaction mechanism of the reference enzyme(s) may be altered to catalyze new reactions, to change, expand or improve substrate specificity. One should appreciate that if the enzyme structure (e.g. crystal structure) is known, enzymes properties may be modified by rational redesign (see US patent application US20060160138, US20080064610 and US20080287320). Modification or improvement in enzyme properties may arise from the introduction of modifications into a polypeptide chain that may, in effect, perturb the structure-function of the enzyme and/or alter its interaction with another molecule (e.g., association with a natural substrate versus an unnatural substrate). It is well known in the art that certain regions of a protein may be critical for enzyme activity, for example amino acids involved in catalysis and substrate binding domains, such that small perturbations to these regions will have significant effects on enzyme function. Some amino acid residues may be at important positions for maintaining the secondary or tertiary structure of the enzyme, and thus also produce noticeable changes in enzyme properties when modified. In some embodiments, the potential pathway components are variants of any of the foregoing. Such variants may be produced by random mutagenesis or may be produced by rational design for production of an enzymatic activity having, for example, an altered substrate specificity, increased enzymatic activity, greater stability, etc. Thus, in some embodiments, the number of modifications to a reference parent enzyme that produces a variant enzyme having the desired property may comprise one or more amino acids, 2 or more amino acids, 5 or more amino acids, 10 or more amino acids, or 20 or more amino acids, up to 10% of the total number of amino acids, up to 20% of the total number of amino acids, up to 30% of the total number of amino acids, up to 40% of the total number of amino acids making up the reference enzyme, or up to 50% of the total number of amino acids making up the reference enzyme.

Those skilled in the art will understand that the engineered pathways exemplified herein are described in relation to, but are not limited to, species specific genes and proteins and that the invention encompasses homologs and orthologs of such gene and protein sequences. Homolog and ortholog sequences possess a relatively high degree of sequence identity/similarity when aligned using methods known in the art. Such homologs or orthologs can suitably be obtained by means of any appropriate cloning strategy known to one skilled in the art. In some embodiments, useful polypeptide sequences have at least 30%, at least 45%, at least 60%, at least 75%, at least 85%, or at least 95% identity to the amino acid sequence of the reference enzyme of interest.

Aspects of the invention relate to new microorganisms or "genetically modified" microorganisms or host cells that have been engineered to possess new metabolic capabilities or new metabolic pathways. As used herein the terms "host cell" and "microorganism" are used interchangeably. As used herein the term "genetically modified," with reference to microorganisms, refers to microorganisms having at least one genetic alteration not normally found in the wild type strain of the reference species. In some embodiments, genetically engineered microorganisms are engineered to express or overexpress at least one particular enzyme at critical points in a metabolic pathway, and/or to block the synthesis of other enzymes, to overcome or circumvent metabolic bottlenecks. The term "metabolic pathway" refers to a series of two or more enzymatic reactions in which the product of one enzymatic reaction becomes the substrate for the next enzymatic reaction. At each step of a metabolic pathway, intermediate compounds are formed and utilized as substrates for a subsequent step. These compounds may be called "metabolic intermediates." The products of each step are also called "metabolites."

Aspects of the invention provide methods for designing and making engineered metabolic pathways. In some aspects of the invention, alternative pathways for making a product of interest from one or more available and sustainable substrates may be made in one or more host cells or microorganisms of interest. One should appreciate that the engineered pathway for making difunctional alkanes of interest may involve multiple enzymes and therefore the flux through the pathway may not be optimum for the production of the product of interest. Consequently, in some aspects of the invention, the carbon flux is optimally balanced by modulating the activity level of the pathway enzymes relative to one another. Examples of such modulation are provided throughout the application. As used herein the term "carbon flux" refers to the number of feedstock molecules (e.g. glucose) which proceed down the engineered pathway relative to competitive paths.

A host cell as used herein refers to an in vivo or in vitro eukaryotic cell, a prokaryotic cell or a cell from a multicellular organism (e.g. cell line) cultured as a unicellular entity. A host cell may be prokaryotic (e.g., a bacterial cell) or eukaryotic (e.g., a yeast, mammal or insect cell). For example, host cells may be bacterial cells (e.g., *Escherichia coli, Bacillus subtilis, Mycobacterium* spp., *M. tuberculosis*, or other suitable bacterial cells), Archaea (for example, *Methanococcus Jannaschii* or *Methanococcus Maripaludis* or other suitable archaic cells), yeast cells (for example, *Saccharomyces* species such as *S. cerevisiae, S. pombe, Picchia* species, *Candida* species such as *C. albicans*, or other suitable yeast species). Eukaryotic or prokaryotic host cells can be, or have been, genetically modified (also referred as "recombinant", "metabolically engineered" or "genetically engineered") and used as recipients for a nucleic acid, such as an expression vector, that comprises a nucleotide sequence encoding one or more biosynthetic or engineered pathway gene products. Eukaryotic and prokaryotic host cells also denote the progeny of the original cell which has been genetically engineered by the nucleic acid. In some embodiments, a host cell may be selected for its metabolic properties. For example, if a selection or screen is related to a particular metabolic pathway, it may be helpful to use a host cell that has a related pathway. Such a host cell may have certain physiological adaptations that allow it to process or import or export one or more intermediates or products of the pathway. However, in other embodiments, a host cell that expresses no enzymes associated with a particular pathway of interest may be selected in order to be able to identify all of the components required for that pathway using appropriate sets of genetic elements and not relying on the host cell to provide one or more missing steps.

According to aspects of the invention, aerobic or anaerobic microorganisms are metabolically engineered. As used herein, an anaerobic organism is any organism that does not require oxygen for growth (i.e. anaerobic conditions), such as certain bacterial cells. Advantageously, the bacterial cell can be an *E. coli, C. glutanicum, B. flavum* or *B. lactofermentum* cell; these strains are currently being employed industrially to make amino compounds using bacterial fermentation processes. For example, *C. glutanicum* has been used extensively for amino acid production (e.g. L-glutamate, L-lysine, see Eggleging L et al., 2005, Handbook for *Corynebacterium glutanicum*. Boca Raton, USA: CRC Press).

The metabolically engineered cell of the invention is made by transforming a host cell with at least one nucleotide sequence encoding enzymes involved in the engineered metabolic pathways. As used herein the terms "nucleotide sequence", "nucleic acid sequence" and "genetic construct" are used interchangeably and mean a polymer of RNA or DNA, single- or double-stranded, optionally containing synthetic, non-natural or altered nucleotide bases. A nucleotide sequence may comprise one or more segments of cDNA, genomic DNA, synthetic DNA, or RNA. In a preferred embodiment, the nucleotide sequence is codon-optimized to reflect the typical codon usage of the host cell without altering the polypeptide encoded by the nucleotide sequence. In certain embodiments, the term "codon optimization" or "codon-optimized" refers to modifying the codon content of a nucleic acid sequence without modifying the sequence of the polypeptide encoded by the nucleic acid to enhance expression in a particular host cell. In certain embodiments, the term is meant to encompass modifying the codon content of a nucleic acid sequence as a means to control the level of expression of a polypeptide (e.g., to either increase or decrease the level of expression). Accordingly, aspects of the invention include nucleic acid sequences encoding the enzymes involved in the engineered metabolic pathways. In some embodiments, a metabolically engineered cell may express one or more polypeptides having an enzymatic activity necessary to perform the steps described throughout the description. For example, a particular cell comprises one, two, three, four, five or more than five nucleic acid sequences with each one encoding the polypeptide(s) necessary to perform the conversion of lysine, lysine metabolite precursor and/or lysine degradation metabolites into difunctional alkane(s). Alternatively, a single nucleic acid molecule can encode one, or more than one, polypeptide. For example, a single nucleic acid molecule can contain nucleic acid sequences that encode two, three, four or even five different polypeptides. Nucleic acid sequences useful for the invention described herein may be obtained from a variety of sources such as, for example, amplification of cDNA sequence, DNA libraries, de novo synthesis, excision of genomic segments, etc. The sequences obtained from such sources may then be modified using standard molecular biology and/or recombinant DNA technology to produce nucleic acid sequences having the desired modifications. Exemplary methods for modification of nucleic acid sequences include for example, site directed mutagenesis, PCR mutagenesis, deletion, insertion, or substitution, or swapping portions of the sequence using restriction enzymes, optionally in combination with ligation, homologous recombination, site specific recombination or various combination thereof. In other embodiments, the nucleic acid sequence may be a synthetic nucleic acid sequence. Synthetic polynucleotide sequences may be produce using a variety of methods described in U.S. Pat. No. 7,323,320, and in copending application having Ser. No. 11/804,996 and in U.S. Patent Publication Nos. 2006/0160138, 2007/0269870, 2008/0064610, and 2008/0287320.

Methods of transformation for bacteria, plant, and animal cells are well known in the art. Common bacterial transformation methods include electroporation and chemical modification.

In some embodiments, a genetically modified host cell is genetically modified such that it produces, when cultured in vitro in a suitable medium, the product of interest or an intermediate at a level of at least 0.1 g/l, at least 1 g/l, at least 10 g/l, at least 50 g/l, at least 100 g/l or at least 150 g/l. One should appreciate that the level of the metabolite of interest or its metabolic intermediates produced by a genetically modified host cell can be controlled in various ways. In some embodiment, the level of expression is controlled by the number of copies of the nucleic acid sequences encoding one or more enzymes involved in the engineered pathway that are contained in the host cell (e.g. high copy expression vector versus medium or low copy expression vectors). Preferably, the nucleic acid sequences are introduced into the cell using a vector. Low copy expression vectors generally provide fewer than 20 vector copies per cell (e.g. from 1 to about 5, from 5 to about 10, from 10 to about 15, from 15 to about 20 copies of the expression vector per cell). Suitable low copy expression vectors for prokaryotic cells (e.g. *E. Coli*) include, but are not limited to pAYC184, pBeloBac11, pBR332, pBAD33, pBBR1MCS and its derivatives, pSC101, SuperCos (cosmid) and pWE15 (cosmid). Medium copy number expression vectors generally provide from about 20 to about 50 expression vectors copies per cell or form about 20 to 80 expression vectors copies per cell. Suitable medium copy expression vectors for prokaryotic cells (e.g. *E. Coli*) include, but are not limited to, pTrc99A, pBAD24 and vectors containing a ColE1 origin of replication and its derivatives. High copy number expression vectors generally provide from about 80 to about 200 or more expression vector copies per cell. Suitable high copy expression vectors for prokaryotic cells (e.g. *E. Coli*) include, but are not limited to, pUC, PCV1, pBluescript, pGEM and pTZ vectors.

Aspects of the invention provide expression cassettes comprising a nucleic acid or a subsequence thereof encoding a polypeptide involved in the engineered pathway. In some embodiments, the expression cassette can comprise the nucleic acid operably linked to control sequences, such as a transcriptional element (e.g. promoter) and to a terminator. As used herein, the term "cassette" refers to a nucleotide sequence capable of expressing a particular gene if the gene is inserted so as to be operably linked to one or more regulatory sequences present in the nucleotide sequence. Thus, for example, the expression cassette may comprise a heterologous gene which is desired to be expressed in the host cell. In some embodiments, one or more expression cassettes may be introduced into a vector by known recombinant techniques. A promoter is a sequence of nucleotides that initiates and controls the transcription of a desired nucleic acid sequence by an RNA polymerase enzyme. In some embodiments, the promoter may be inducible. In other embodiment, promoters may be constitutive. Non limiting examples of suitable promoters for the use in prokaryotic host cells include a bacteriophage T7 RNA polymerase promoter, a trp promoter, a lac operon promoter and the like. Non limiting examples of suitable strong promoters for the use in prokaryotic cells include lacUV5 promoter, T5, T7, Trc, Tac and the like. Non limiting examples of suitable promoters for use in eukaryotic cells include a CMV immediate early promoter, a SV40 early or late promoter, a HSV thymidine kinase promoter and the like. Termination control regions may also be derived from various genes native to the preferred host.

In some embodiments, a first enzyme of the engineered pathway may be under the control of a first promoter and the second enzyme of the engineered pathway may be under the control of a second promoter, wherein the first and the second promoter have different strengths. For example, the first promoter may be stronger than the second promoter or the second promoter may be stronger than the first promoter. Consequently, the level of a first enzyme may be increased relative to the level of a second enzyme in the engineered pathway by increasing the number of copies of the first enzyme and/or by increasing the promoter strength to which the first enzyme is operably linked to relative to the promoter strength to which the second enzyme is operably linked to. In some other embodiments, the plurality of enzymes of the engineered pathway may be under the control of the same promoter. In other embodiments, altering the ribosomal binding site affects relative translation and expression of different enzymes in the pathway. Altering the ribosomal binding site can be used alone to control relative expression of enzymes in the pathway, or it can be used in concert with the aforementioned promoter modifications and codon optimization that also affects gene expression levels.

In an exemplary embodiment, expression of the potential pathway enzymes may be dependent upon the presence of a substrate that the pathway enzyme will act on in the reaction mixture. For example, expression of an enzyme that catalyzes conversion of A to B may be induced in the presence of A in the media. Expression of such pathway enzymes may be induced either by adding the compound that causes induction or by the natural build-up of the compound during the process of the biosynthetic pathway (e.g., the inducer may be an intermediate produced during the biosynthetic process to yield a desired product).

One should appreciate that the designation of the enzymes are governed by the specific reaction catalyzed by them as is depicted in FIG. 2-9. It is possible for a single enzyme to catalyze two reactions that are chemically identical but are assigned to different pathways on the basis of the respective substrate. This may be associated with different enzyme classification numbers (e.g. EC numbers). In some instance, enzymes have not been yet allocated an EC number, which is why reference is only made for definition of the relevant enzymatic reaction.

In some embodiments, computer-implemented design techniques may be used to generate alternative pathways for generating an organic compound of interest. In some embodiments, the databases contain genomic information and their link may be utilized for designing novel metabolic pathways. Examples of database are MetaCyc (a database of metabolic pathways and enzymes), the University of Minnesota biocatalysis/biodegradation database (a database of microbial catalytic reactions and biodegradation pathways for organic chemical compounds), LGAND (a composite database that provides information about metabolites and other chemical compounds, substrate-product relations representing metabolic and other reactions and information about enzyme molecules). A database of pathway components may also contain components of predicted, putative, or unknown functions. It may also contain pseudo-components of defined function that may have an undefined composition. In some embodiments, a program may design combinations of regulatory and/or functional elements that are in the public domain (e.g., that are not covered by patent rights and/or are not subject to a licensing fee). Databases of freely available genetic elements may be generated and/or used as a source of nucleic acid sequences that can be combined to produce alternative pathways. Alternative pathways containing different combinations of known functional and/or regulatory elements (e.g., from different species) may be designed, assembled, and/or tested. Libraries including variations in enzymatic element regions may be used to ascertain the relative effects of different types of enzymes or of different variants of the same enzyme. Libraries including variations in regulatory element regions may be used to ascertain the optimal expression level or regulatory control among a set of genes. In some embodiments, the functional properties of different engineered pathways may be tested in vivo by transforming host cells or organisms with the appropriate assembled nucleic acids, and assaying the properties of the engineered organisms. In some embodiments, the functional properties of different engineered pathways may be tested in vitro by isolating components expressed from assembled nucleic acids and testing the appropriate combinations of components in an in vitro system.

1. Engineered Pathways for the Production of C6 Difunctional Alkanes

Aspects of the invention relate to design and assembly of engineered pathways for the production of C6 difunctional alkanes of interest. Particularly, aspects of the invention relate to the production of adipic acid, amino caproic acid (a stable precursor of caprolactam acid), hexamethylenediamine, 6-amino hexanol, 1,6-hexanediol and 6-hydroxyhexanoate.

A. Background on C6 Difunctional Hexane Molecules

1. Overview on Adipic Acid:

In 2005, global demand for adipic acid was 2.7 million metric tons. Historically the demand for adipic acid has grown 2% per year and a 2-3% increase is expected through the year 2009. Adipic acid consistently ranks as one of the top fifty chemicals produced in the US. Nearly 90% of domestic adipic acid is used to produce nylon-6,6. Other uses of adipic acid include production of lubricants resins, polyester polyols and plasticizers, and food acidulant.

There are three major commercial production processes: cyclohexane process, cyclohexanol process, butadiene carbonylation process. The dominant industrial process for synthesizing adipic acid employs initial air oxidation of cyclohexane to yield a mixture of cyclohexanone (ketone) and cyclohexanol (alcohol), which is designated KA (see for example U.S. Pat. No. 5,221,800). Hydrogenation of phenol to yield KA is also used commercially, although this process accounts for just 2% of all adipic acid production. KA produced via both methods is oxidized with nitric acid to produce adipic acid. Reduced nitrogen oxides including $NO_2$, NO, and $N_2O$ are produced as by-products and are recycled back to nitric acid at varying levels. It is becoming increasingly more interesting to industry and beneficial to the environment to engineer non-synthetic, biological routes to adipic acid. A number of microbiological routes have been described. Wild-type and mutant organisms have been shown to convert renewable feedstocks such as glucose and other hydrocarbons to adipic acid (see for example WO9507996, and U.S. Pat.

No. 5,272,073, U.S. Pat. No. 5,487,987 and U.S. Pat. No. 5,616,496). Similarly, organisms possessing nitrilase activity have been shown to convert nitriles to carboxylic acids including adipic acid (see for example U.S. Pat. No. 5,629,190). Additionally, wild-type organisms have been used to convert cyclohexane and cyclohexanol and other alcohols to adipic acid (see for example U.S. Pat. No. 6,794,165; and US Patent Applications No 2003087403 and 20020127666). For example, in one enzymatic pathway, cyclohexanol is converted in adipic acid, the enzymatic pathway comprising genes isolated from an *Acinetobacter* encoding hydroxylacylCoA dehydrogenase; enoylCoA hydratase, acylCoA dehydrogenase, ubiquinone oxidoreductase, monoxygenase, aldehyde dehydrogenase. Another enzymatic pathway for the conversion of cyclohexanol to adipic acid has been suggested as including the intermediates cyclohexanol, cyclohexanone, 2-hydroxycyclohexanone, ε-caprolactone, 6-hydroxycaproic acid. Some specific enzyme activities in this pathway have been demonstrated, including cyclohexanol dehydrogenase, NADPH-linked cyclohexanone oxygenase, ε-caprolactone hydrolase, and NAD (NADP)-linked 6-hydroxycaproic acid dehydrogenase (Tanaka et al., Hakko Kogaku Kaishi (1977), 55(2), 62-7). An alternate enzymatic pathway has been postulated to comprise cyclohexanol, cyclohexanone, 1-oxa-2-oxocycloheptane, 6-hydroxyhexanoate, 6-oxohexanoate and adipate (Donoghue et al., Eur. J. Biochem., 1975, 60(1), 1-7).

2. Caprolactam and 6-Aminocaproic Acid Overview

Aminocaproic acid (or ε-aminocaproic acid, or IUPAC name 6-aminohexanoic acid) is a possible intermediate for the production of caprolactam. Caprolactam is primarily used in the manufacture of synthetic fibers, especially nylon 6 that is also used in bristle brushes, textile stiffeners, film coatings, synthetic leather, plastics, plasticizers, vehicles, cross linking for polyurethanes, and in the synthesis of lysine. About 2.5 billion tons of nylon 6 is produced annually on a worldwide basis. The production of nylon 6 is accomplished by the ring opening polymerization of the monomer ε-caprolactam. The starting chemical compound for the production of s-caprolactam is benzene which is converted to either cyclohexane or phenol and either chemical is converted via cyclohexanone to cyclohexanone oxime and then this intermediate is heated in sulfuric acid.

3. Other C6 Difunctional Alkanes

Hexamethylenediamine is mostly used for the production of Nylon 6,6, Nylon 6,10, Nylon 6,66. Nylon 6,6 and nylon 6,10 can be made into various kinds of nylon resins and nylon fiber. 6-hydroxyhexanoate (6HH) is a 6-carbon hydroxyalkanoate that can be circularized to caprolactone or directly polymerized to make polyester plastics (polyhydroxyalkanoate PHA). 1,6-hexanediol is a valuable intermediate for the chemical industry. It has applications in a variety of polymer syntheses such as the production of polyesters for polyurethane elastomers and polymeric plasticizers and is also used in gasoline refining.

The problem to be solved therefore is to provide a synthesis route for difunctional alkanes which not only avoids reliance on environmentally sensitive starting materials such as petroleum but also makes efficient use of non-petrochemical inexpensive, renewable resources. It would further be desirable to provide a synthesis route for difunctional alkanes which avoids the need for significant energy inputs, optimizes carbon flux and minimizes the formation of toxic by-products.

B. Engineered Pathways for the Production of 6-Aminocaproic Acid and its Intermediates from Lysine Lysine (Lys or K) is a 1,2,6-trifunctional hexane with the chemical formula $NH_2(CH2)_4CHNH_2COOH$ (FIG. 1). L-lysine is an important economic product obtained principally by industrial-scale fermentation utilizing the Gram positive *Corynebacterium glutamicum, Brevibacterium flavum* and *Brevibacterium lactofermentum*. A considerable amount is known regarding the biochemical pathway for L-lysine synthesis in *Corynebacterium* species (see for example WO04013341 and WO01665730). In plants and microorganisms, lysine is synthesized from aspartic acid, which is first converted to β-aspartyl-semialdehyde, cyclizated into dihydropicolinate, which is then reduced to $\Delta^1$-piperidine-2,6-dicarboxylate. Ring-opening of this heterocycle gives a series of derivatives of pimelic acid, and ultimately leads to lysine. Enzymes involves in the lysine biosynthesis include (Lehninger, A. L., D. L. Nelson, and M. M. Cox. 2000. *Lehninger Principles of Biochemistry*, 3rd ed. New York: Worth Publishing): aspartokinase, β-aspartate semialdehyde dehydrogenase, dihydropicolinate synthase, Δ1-piperdine-2,6-dicarboxylate dehydrogenase, N-succinyl-2-amino-6-ketopimelate synthase, succinyl diaminopimelate aminotransferase, succinyl diaminopimelate desuccinylase, diaminopimelate epimerase, diaminopimelate decarboxylase. In mammals, lysine is metabolized to give acetyl-CoA, via an initial transamination with α-ketoglutarate. The bacterial degradation of lysine yields to cadaverine by decarboxylation.

One skilled in the art will appreciate that lysine is an ideal precursor of difunctional alkanes as it can be produced in high yield and it contains an unbroken 6-carbon-chain with functionalized ends. Aspects of the invention provide potential pathways for the bioproduction of C6 difunctional alkanes. Detailed explanations of the relevant metabolic pathways are given hereinafter.

Figure 2:
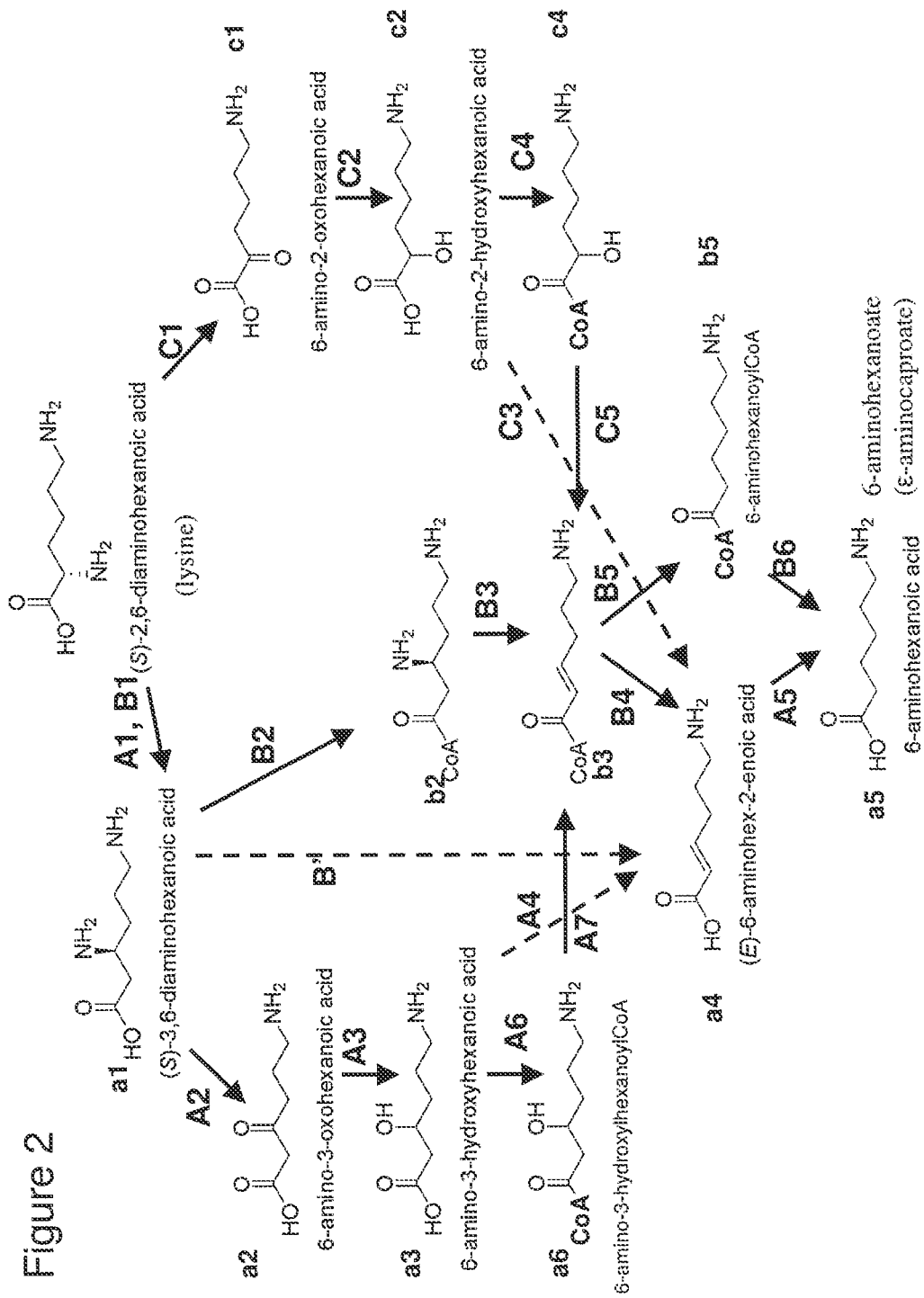
FIG. 2 represents a flow diagram for the bioproduction of aminocaproic acid from lysine.

Aspects of the invention provide several metabolic pathways that can be used to produce organic compounds such as aminocaproic acid and its intermediates from lysine. These pathways are shown in FIGS. 2-3. Accordingly, aspects of the invention provide a recombinant microorganism having an engineered aminocaproic acid biosynthetic pathway. In some embodiments, L-lysine production involves the use of molecular biology techniques to augment L-lysine production. Accordingly, in some embodiments, recombinant microorganisms have at least one gene that is expressed at a level lower or higher than that expressed prior to manipulation of the microorganism or in a comparable microorganism which has not been manipulated. Genes are selected from the group of genes which play a key role in the biosynthesis of lysine such as aspartokinase, aspartate semialdehyde dehydrogenase, dihydrodipicolinate synthase, dihydrodipicolinate reductase, tetrahydrodipicolinate succinylase, succinyl-amino-ketopimelate transaminase, succinyl-diaminopimelate desuccinylase, diaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, phosphogluconolactonase, fructose 1,6-biphosphatase, homoserine dehydrogenase, phophoenolpyruvate carboxykinase, succinyl-CoA synthetase, methyl-malonyl-CoA mutase.

As described in FIG. 2, 6-aminohex-2-enoic and/or 6-aminohex-2-enoyl-CoA are intermediates to several of the aminocaproic acid biosynthetic pathway. Accordingly, other aspects of the invention provide a recombinant microorganism having an engineered 6-aminohex-2-enoic acid or 6-aminohex-2-enoyl-CoA biosynthetic pathway. In some embodiments, the 6-aminohex-2-enoic acid biosynthetic pathway is the same as the aminocaproic biosynthetic pathway with omission of the last enzymatic step. In a preferred embodiment, the engineered microorganisms are used for the commercial production of aminocaproic acid or its intermediates. One skilled in the art will appreciate that aminocaproic acid $NH_2(CH2)_5COOH$ is a derivative and analogue of the amino acid lysine $NH_2(CH2)_4CHNH_2COOH$ and lysine is therefore an ideal biological precursor of the aminocaproic acid. Aspects of the invention relate to a process for aminocaproic acid production and applying at least one enzymatic step A, B, B' and/or C as illustrated in the pathway shown in FIG. 2. Accordingly, aspects of the invention provide a recombinant host cell or microorganism comprising at least one nucleic acid molecule encoding at least one polypeptide that catalyzes a substrate to product conversion as illustrated in FIG. 2.

Aspects of the invention relate to different possible pathways to aminocaproic acid:
1) Pathway I comprising enzymatic steps A1, B2, B3, B4, and A5;
2) Pathway II comprising enzymatic steps A1, A2, A3, A4 and A5;
3) Pathway III comprising enzymatic steps A1, A2, A3, A6, A7, B5 and B6;
4) Pathway IV comprising enzymatic steps A1, A2, A3, A6, A7, B4 and A5;
5) Pathway V comprising enzymatic steps A1, B2, B3, B5 and B6;
6) Pathway VI comprising enzymatic steps A1, B' and A5;
7) Pathway VII comprising enzymatic steps C1, C2, C3 and A5;
8) Pathway VIII comprising enzymatic steps C1, C2, C4, C5, B4 and A5; and
9) Pathway IX comprising enzymatic steps C1, C2, C4, C5, B5 and B6.

a) Conversion of Lysine to 3,6-Diaminohexanoic Acid

In some embodiments, the aminocaproic biosynthetic pathway begins with the conversion of lysine to 3,6-diaminohexanoic acid by action of an aminomutase as shown in the substrate to product conversion step A1 in FIG. 2 (Pathways I through VI). In a preferred embodiment, the lysine aminomutase is a lysine 2,3-aminomutase (KAM or LAM) (EC 5.4.3.2) which facilitates the conversion of the amino acid lysine to 3,6-diaminohexanoic acid or beta-lysine as shown below:

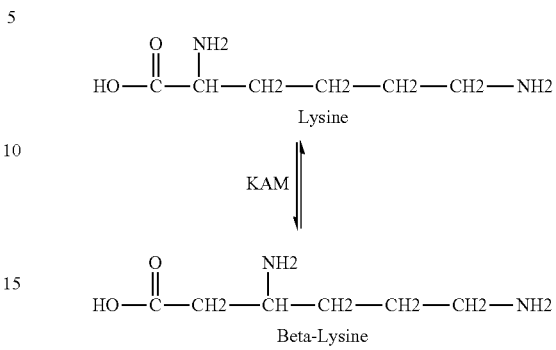

Lysine 2,3 aminomutase uses Pyridoxal phosphate, Zinc and a 4 Iron-4 Sulfur cluster as cofactors and a 5'-deoxyadenosyl radical formed in an S-Adenosyl methionine (SAM) activated radical reaction pathway. The skilled person will appreciate that polypeptides having an L-lysine 2,3-aminomutase activity may be isolated from a variety of sources. Examples of L-lysine 2,3-aminomutase, include but are not limited, to EC 5.4.3.2. (encoded by kamA in *Fusobacterium nucleatum, Clostridium subterminale* or *Bacillus subtilis*), EC 5.4.3.-(encoded by yjeK in *Escherichia Coli* K1), EC 5.4.3.7 (leucine 2,3-aminomutase from *Andrographis paniculata, Candida utilis, Clostridium lentoputrescens, Clostridium sporogenes, Rattus norvegicus*), and EC 5.4.3.6 (Tyrosine 2,3-aminomutase).

b) Conversion of 3,6-diaminohexanoic acid to 6-amino-3-oxohexanoic acid

According to the pathways II, III and IV, 3,6-diaminohexanoic acid (a1) is first converted into 6-amino-3-oxohexanoic acid (b2, step A2). Although there are no reported enzymes that catalyze the substrate to product conversion of a1 to a2, the substrate shows some similarity to those utilized in Table 1 and may be converted by action of an enzyme having an aminotransferase (or dehydrogenase) activity as listed in Table 1. As meant herein, enzymes having an aminotransferase or dehydrogenase activity are understood to be enzymes that catalyze the transfer of a 2-amino group from a lysine molecule to a recipient molecule, leaving behind a β-ketoacid (or 3-oxoacid) molecule containing a primary amino group. The skilled person will appreciate that polypeptides useful for converting 3,6-diaminohexanoic acid into 6-amino-3-oxohexanoic acid are exemplified but not limited to the enzymes listed in Table 1 and may be isolated from a variety of sources.

TABLE 1

| Desired substrate and product<br>EC number<br>Name<br>Gene name (organism)<br>Protein accession number | (S)-3,6-diaminohexanoic acid → 6-amino-3-oxohexanoic acid |
|---|---|

TABLE 1-continued 2.6.1.19
4-aminobutanoate: 2-oxoglutarate aminotransferase
GabT from *E. Coli*
puuE from *E. Coli*
UGA1 from *S. cerevisiae*
ABAT from *Homo sapiens*
GabT from *Pseudomonas fluorescens*

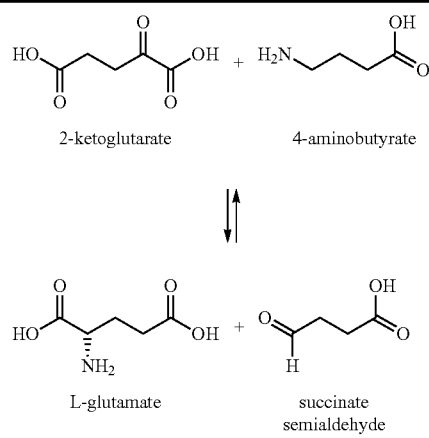

2.6.1.65
N6-acetyl-(β-lysine aminotransferase
*Pseudomonas* sp.

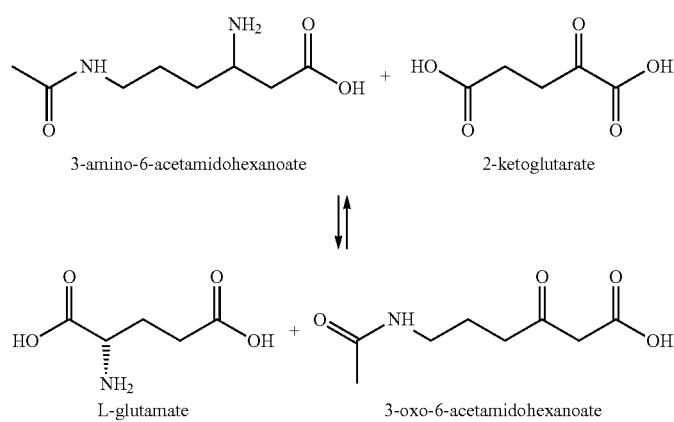

1.4.1.11
L-erythro-3,5-diaminohexanoate dehydrogenase
kdd from *Fusobacterium nucleatum*

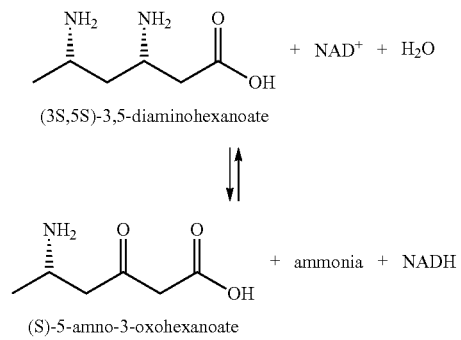

c) Conversion of 6-amino-3-oxohexanoic acid into 6-amino-3-hydroxyhexanoic acid In some embodiments, the resulting product 6-amino-3-oxohexanoic acid (a2) of enzymatic step A2, is further converted into 6-amino-3-hydroxyhexanoic acid (a3) by action of a reductase enzyme (enzymatic step A3, pathways II, III, and IV). Because of the reversibility of most reactions catalyzed by oxido-reductases, enzymatic step A3 may be catalyzed by a dehydrogenase enzyme. As used herein, the reductase/dehydrogenase enzyme catalyses the carbonyl reduction of the β-ketones to its corresponding hydroxyl-derivative (secondary alcohol). In some cases, the oxidizing equivalent is supplied in the form of an oxidized nicotinamide cofactor, NAD(+) or NADP(+). Non-limiting examples of reductase or dehydrogenase enzymes useful in the present invention are listed in Table 2 and may be available from different sources. Although there are no reported enzymes that catalyze the substrate to product conversion of a2 to a3, the substrate shows some similarity to those utilized in Table 2 and may be converted by action of an enzyme having a reductase or dehydrogenase activity as listed in Table 2. Preferably, the reductase enzyme is L-carnitine dehydrogenase, 3-hydroxypropionate dehydrogenase, (S)-carnitine 3-dehydrogenase, Hydroxyacid-oxoacid transhydrogenase, malonate semialdehyde reductase (NADPH) or 3-oxo-acyl-CoA reductase.

TABLE 2
| | |
|---|---|
| Desired substrate product reaction EC number Name Gene name (organism) Protein accession number | 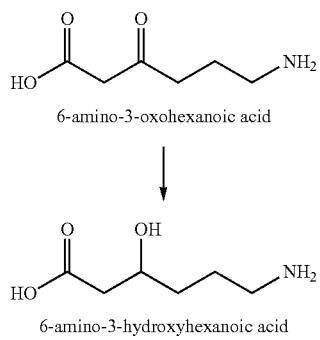 [SMILES: NCCCC(=O)CC(=O)O ; NCCCC(O)CC(=O)O] |
| EC 1.1.1.108 L-carnitine dehydrogenase PP0302 from *Pseudomonas putida* | 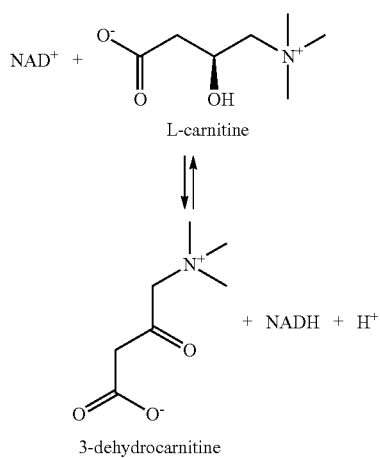 |
| EC 1.1.1.59 3-hydroxypropionate dehydrogenase | 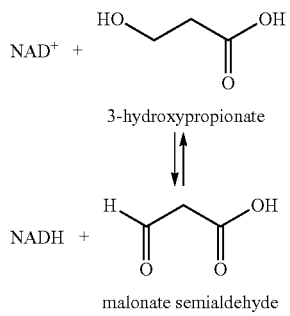 |
| EC.1.1.1.35 enoyl-CoA hydratase fadJ and fadB from *E. Coli* | 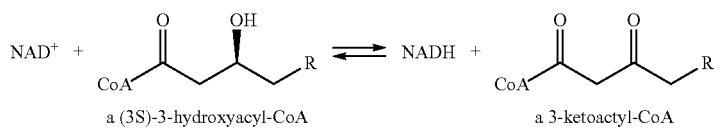 |
| EC 1.1.1.36 phaB (*Rhodobacter sphaeroides*), PhbB (*Zoogloea ramigera*) UniProt: Q3IZW0 | 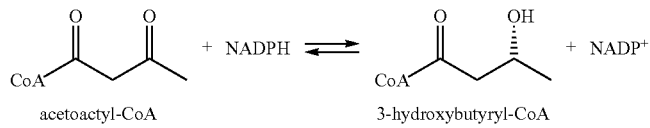 |
| EC 1.1.1.100 | 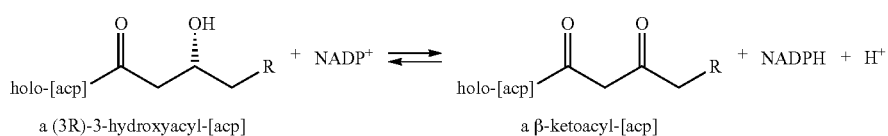 |

TABLE 2-continued

| EC 1.1.1.178 HADH2 (*Homo sapiens*); fadB2x (*Pseudomonas putida*) | 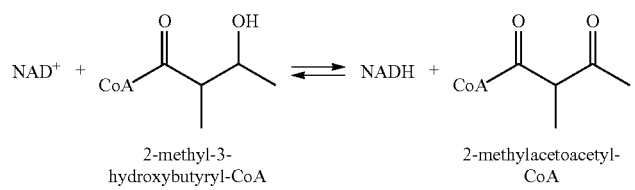 2-methyl-3-hydroxybutyryl-CoA ⇌ 2-methylacetoacetyl-CoA |
| --- | --- |
| EC 1.1.1.211 HADHA (*Homo sapiens*); Hadha (rat) P40939; Q64428 | 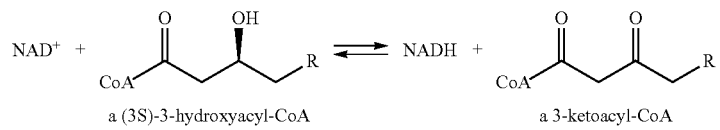 a (3S)-3-hydroxyacyl-CoA ⇌ a 3-ketoacyl-CoA |
| EC 1.1.1.212 | 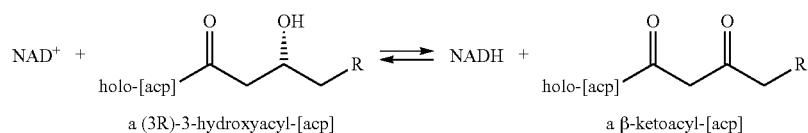 a (3R)-3-hydroxyacyl-[acp] ⇌ a β-ketoacyl-[acp] |
| EC 1.1.1.254 (S)-carnitine 3-dehydrogenase | 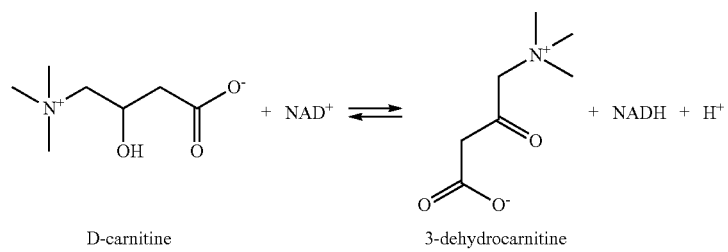 D-carnitine ⇌ 3-dehydrocarnitine |
| EC 1.1.1.259 | 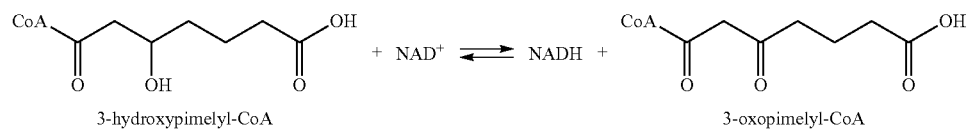 3-hydroxypimelyl-CoA ⇌ 3-oxopimelyl-CoA |
| EC 1.1.99.24 Hydroxyacid-oxoacid transhydrogenase | 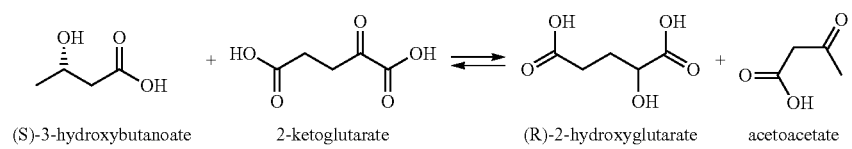 (S)-3-hydroxybutanoate + 2-ketoglutarate ⇌ (R)-2-hydroxyglutarate + acetoacetate |
| EC1.1.99.26 3-hydroxycyclo-hexanone dehydrogenase | 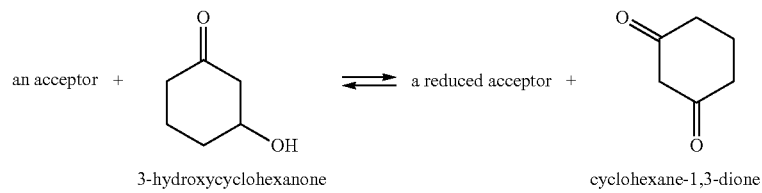 [SMILES: O=C1CCCC(O)C1 ; O=C1CCCC(=O)C1] an acceptor + 3-hydroxycyclohexanone ⇌ a reduced acceptor + cyclohexane-1,3-dione |
| EC 1.1.1.- malonate semialdehyde reductase (NADPH) (*Metallosphaera sedula*) malonyl CoA reductase (*Chloroflexus aurantiacus*) | 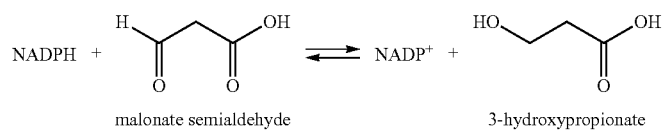 [SMILES: O=CCC(=O)O ; O=C(O)CCO] malonate semialdehyde ⇌ 3-hydroxypropionate |

TABLE 2-continued

EC 1.1.1.-
3-oxo-acyl-CoA
reductase (*Rattus norvegicus*)

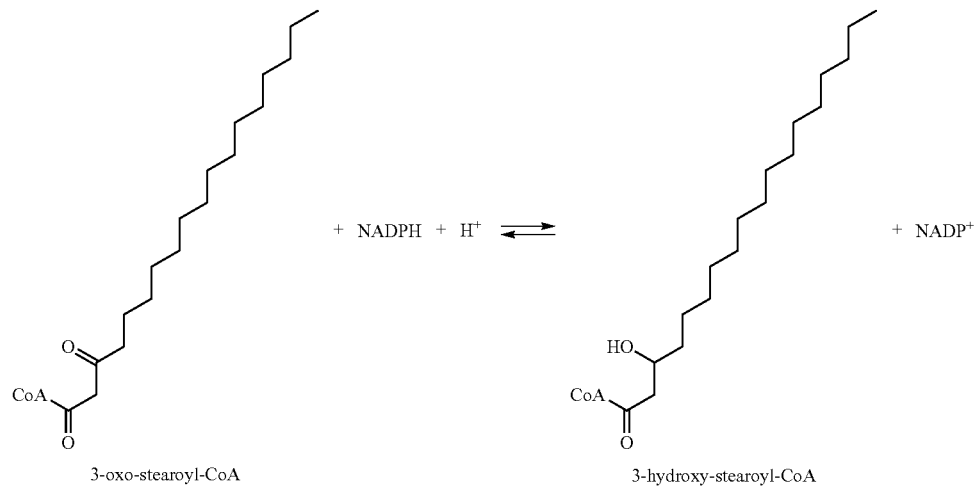

3-oxo-stearoyl-CoA → 3-hydroxy-stearoyl-CoA d) Conversion of 6-amino-3-hydroxyhexanoic acid into (E)-6-aminohex-2-enoic acid In enzymatic step A4 (pathway II, FIG. 2), 6-amino-3-hydroxyhexanoic acid (a3) is converted into (E)-6-aminohex-2-enoic acid (a4) by a dehydratase or hydro-lyase which cleaves carbon-oxygen bonds by elimination of water. Although there are no enzymes reported to catalyze the enzymatic reaction A4, the substrate (E)-6-aminohex-2-enoic acid is similar to those utilized by the reductase enzymes listed in Table 3. Preferably, the reductase enzyme is a trans-L-3-hydroxyproline dehydratase, a dimethylmaleate hydratase, an L-carnitine dehydratase, a fumarate dehydratase, or a 2-oxohept-3-endioate hydroxylation. One skilled in the art will appreciate that polypeptides having a reductase activity include, but are not limited to the ones listed below and may be isolated from a variety of sources.

TABLE 3

| Desired substrate and product reaction<br>EC number<br>Name<br>Gene name (organism)<br>Protein accession number | 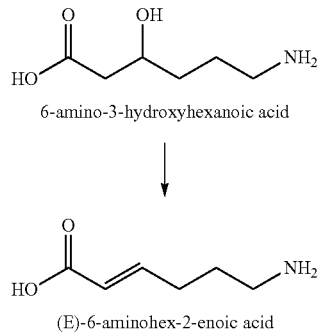 [SMILES: NCCCC(O)CC(=O)O ; NCCC/C=C/C(=O)O]<br>6-amino-3-hydroxyhexanoic acid<br>↓<br>(E)-6-aminohex-2-enoic acid |
|---|---|
| EC 4.2.1.17<br>enoyl-CoA hydratase<br>((3S)-3-hydroxyacyl-CoA hydro-lyase)<br>gene: MaoC (*E. Coli*), PhaJ1 (*Pseudomonas aeruginosa*), perMFE (*Rattus norvegicus*), MFE-2 (*Homo sapiens*)<br>protein accession number: Q64428 (*Rattus norvegicus*); Q95KZ6 (*Bos Taurus*) | 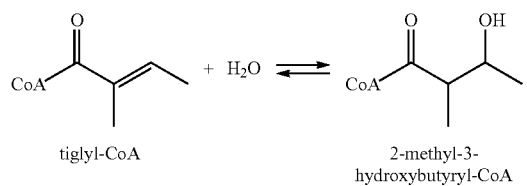<br>tiglyl-CoA → 2-methyl-3-hydroxybutyryl-CoA |

TABLE 3-continued

| | | |
|---|---|---|
| EC 4.2.1.18 methylglutaconyl-CoA hydratase ((S)-3-hydroxy-3-methylglutaryl-CoA hydro-lyase) AUH (*Homo sapiens*), Protein accession number: Q3HW12 (*Acinetobacter* sp.); Q13825 (*Homo sapiens*) | 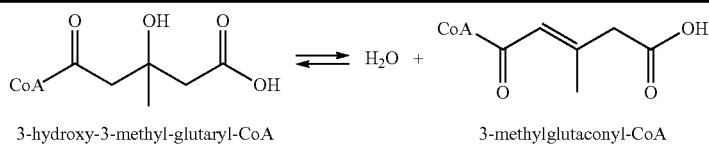 3-hydroxy-3-methyl-glutaryl-CoA | 3-methylglutaconyl-CoA |
| EC 4.2.1.55 Crotonase (3-hydroxybutyryl-CoA dehydratase) Gene: crotonyl-CoA hydratase [(S)-3-hydroxybutyryl-CoA-forming](*Metallosphaera sedula*) Crotonase: crtl (*Clostridium kluyveri*) enoyl-CoA hydratase: ech (*Pseudomonas putida*) Crotonase: crt (*Clostridium acetobutylicum*) Protein accession number: P52046 (*Clostridium acetobutylicum*) | 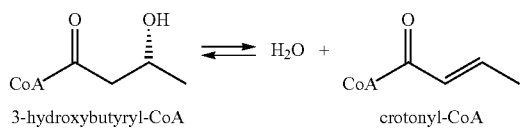 3-hydroxybutyryl-CoA | crotonyl-CoA |
| EC 4.2.1.58 Crotonoyl-[acyl-carrier-protein]hydratase fatty acid synthase: FASN (*Homo sapiens*); β-hydroxyacyl-ACP dehydrase [multifunctional]: fabA (*Escherichia coli* K12); β-hydroxyacyl-ACP dehydratase: fabZ (*Escherichia coli* K12) | 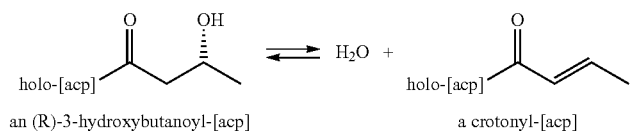 an (R)-3-hydroxybutanoyl-[acp] | a crotonyl-[acp] |
| EC 4.2.1.59 β-hydroxyacyl-ACP dehydratase fabZ (*Escherichia coli* K12); fabA (*Escherichia coli* K12). UniProt accession number: P0A6Q3 (*E. Coli*), P45159 (*Haemophilus influenzae*). | 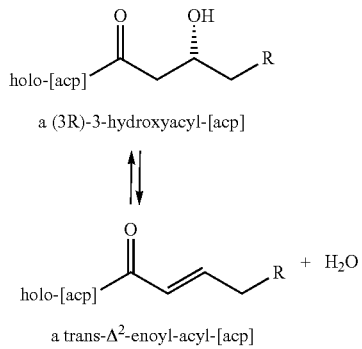 a (3R)-3-hydroxyacyl-[acp] | a trans-$\Delta^2$-enoyl-acyl-[acp] |
| EC 4.2.1.74 Long-chain-enoyl-CoA hydratase HADHA (*Homo sapiens*); Hadha (*Rattus norvegicus*) UniProt P40939 (*Homo sapiens*); UniProtQ64428 (*Rattus norvegicus*) | 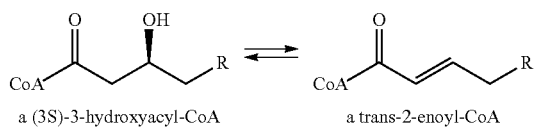 a (3S)-3-hydroxyacyl-CoA | a trans-2-enoyl-CoA |
| EC 4.2.1.77 Trans-L-3-hydroxyproline dehydratase *Rattus norvegicus* | 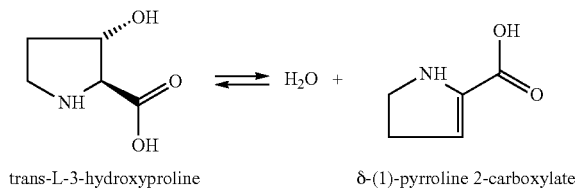 trans-L-3-hydroxyproline | δ-(1)-pyrroline 2-carboxylate |

TABLE 3-continued
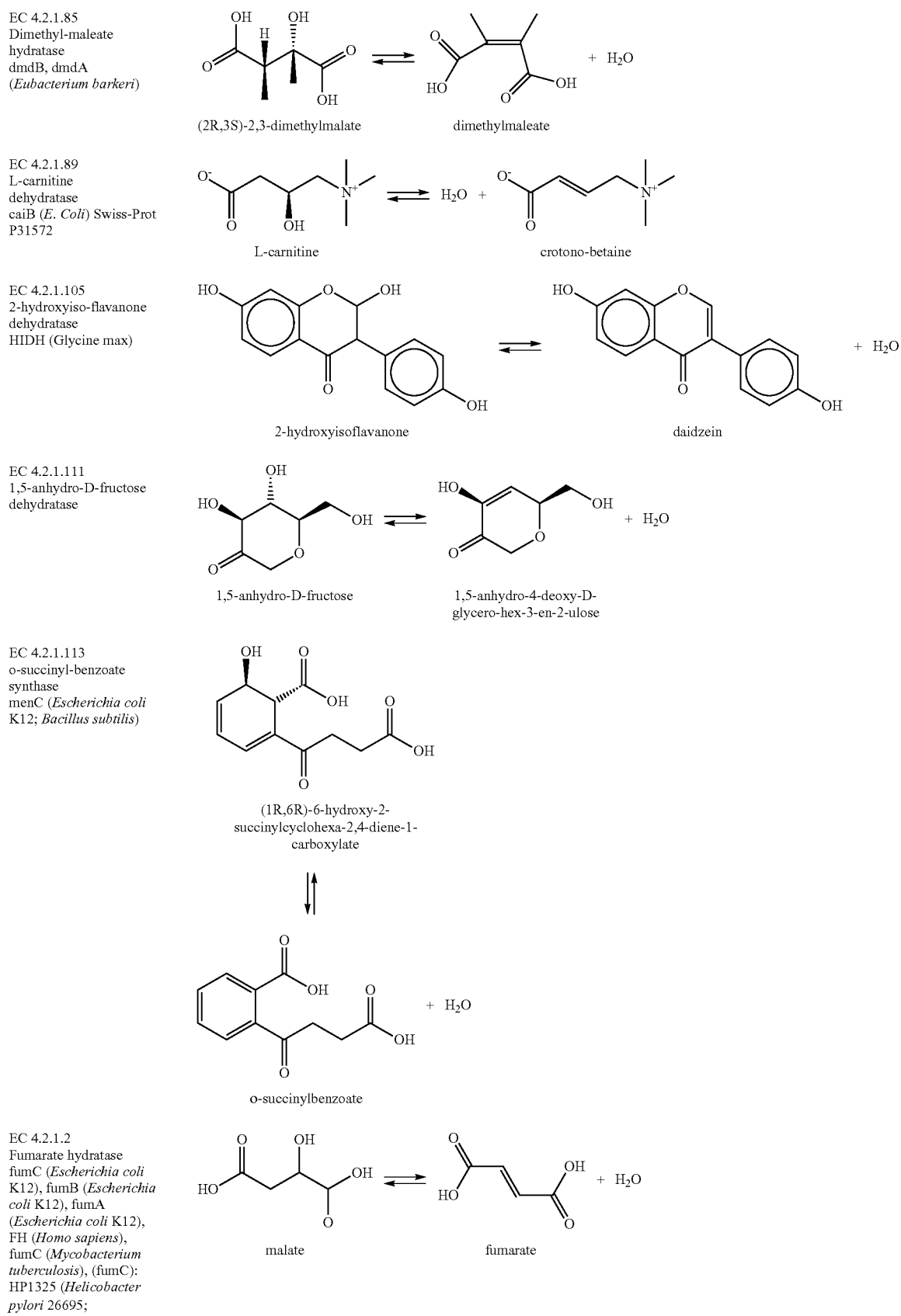

TABLE 3-continued

*Methanococcus
maripaludis,
Desulfobacter
hydrogenophilus*
UniProt: O25883,
UniProt: O53446,
UniProt: O66271,
UniProt: O69294,
UniProt: O84863,
UniProt: O94552,
UniProt: P05042,
UniProt: P07343,
UniProt: P08417,
UniProt: P0AC33
UniProt: P10173,
UniProt: P14407,
UniProt: P14408,
UniProt: P39461,
UniProt: P93033
UniProt: Q7M4Z3,
UniProt: Q9JTE3,
UniProt: Q9JTR0,
UniProt: Q04718,
UniProt: Q43180,
UniProt: Q51404,
UniProt: Q55674,
UniProt: Q58034,
UniProt: Q58690,
UniProt: Q60022

EC 4.2.1.-
crotonobetainyl-CoA
hydratase
caiD (*Escherichia coli*
K12)

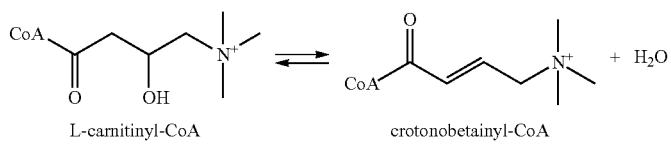

L-carnitinyl-CoA     crotonobetainyl-CoA

EC 4.2.1.-
2-hydroxy-isoflavanone
dehydratase
HIDH (*Glycine max*)

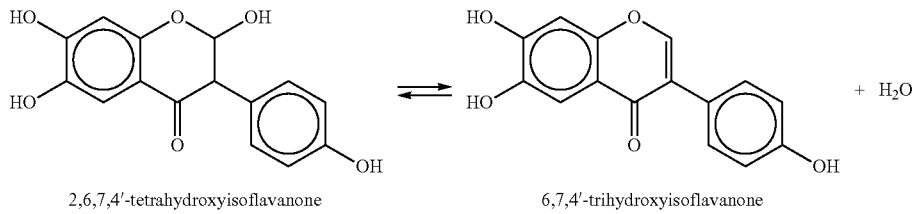

2,6,7,4'-tetrahydroxyisoflavanone     6,7,4'-trihydroxyisoflavanone

EC 4.2.1.-
2-oxohept-3-enedioate-
hydroxylation

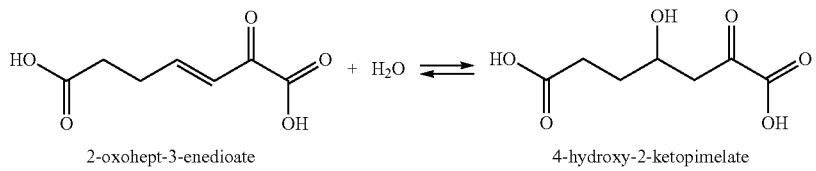 [SMILES: O=C(O)CC/C=C/C(=O)C(=O)O ; O=C(O)CCC(O)CC(=O)C(=O)O]

2-oxohept-3-enedioate     4-hydroxy-2-ketopimelate e) Conversion of 6-aminohex-2-enoic acid into aminocaproic acid Pathways I, II, IV, VI, VII, and VIII conclude with the conversion of 6-aminohex-2-enoic acid into aminocaproic acid. The reduction of (E)-6-aminohex-2-enoic acid to aminocaproic acid (a4→a5, enzymatic step A5) is catalyzed by a polypeptide having a reductase or a dehydrogenase activity. An example of an enzyme catalyzing this reaction is an enoate-reductase capable of hydrogenating the α,β-carbon-carbon double bond at the α,β-position next to a carboxylic acid group into a carbon-carbon single bond. Example of enzymes having a α,β enoate reductase activity can be found in US applications 20070117191 and 20070254341. Other exemplary polypeptides having an enoate reductase activity are listed in Table 4. Preferably, the enoate reductase is a 2-enoate reductase, a NADH-dependent fumarate reductase, a succinate dehydrogenase, a coumarate reductase, a β-nitroacrylate reductase, a methylacetate reductase, or a γ-butyrobetaine reductase.

TABLE 4

| | | |
|---|---|---|
| Desired substrate and product reaction<br>EC number<br>Name<br>Gene name (organism)<br>Protein accession number (organism) | (E)-6-aminohex-2-enoic acid<br>↓<br>6-aminohexanoic acid | |
| EC 1.3.1.31<br>2-enoate reductase<br>P11887 (*Clostridium tyrobutyricum*) | NAD⁺ + butyrate ⇌ NADH + crotonate | |
| EC 1.3.1.6<br>NADH-dependent fumarate reductase | NAD⁺ + succinate ⇌ NADH + fumarate | |
| EC 1.3.99.1<br>Succinate dehydrogenase<br>sdhA (*Mycobacterium tuberculosis*),<br>(*Methanococcus maripaludis*)<br>fumarate reductase<br>(*Aquifex pyrophilus*) | succinate + an acceptor ⇌ fumarate + a reduced acceptor | |
| EC 1.3.1.11<br>Coumarate reductase | melilotate + NAD⁺ ⇌ NADH + 2-coumarate | |
| EC 1.3.1.16<br>β-nitroacrylate reductase | NADP⁺ + 3-nitropropanoate ⇌ NADPH + 3-nitroacrylate | |
| EC 1.3.1.32<br>Maleylacetate reductase<br>pnpE (*Pseudomonas* sp. ENV2030); macA (*Rhodococcus opacus*);<br>(*Xanthobacter flavus*);<br>tftE (*Burkholderia cepacia*)<br>Q45072 (*Burkholderia cepacia*) | 3-nitropropanoate + NADP⁺ ⇌ 3-nitroacrylate + NADH + H⁺ | |

TABLE 4-continued

EC 1.3.1.9
NADPH 2-enoyl CoA reductase
enrA1 (*Brassica napus*)

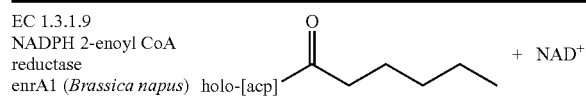

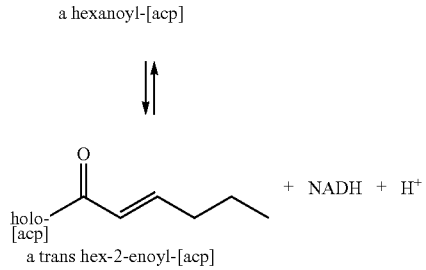

EC 1.3.1.39
Enoyl-[acyl-carrier protein]reductase
FASN (*Homo sapiens*)

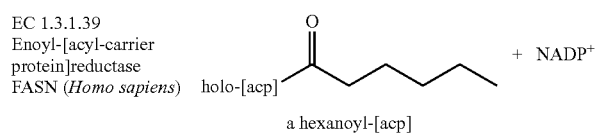

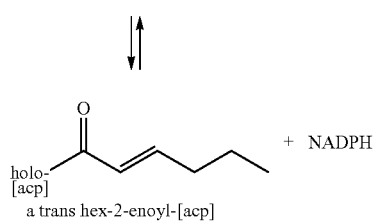

EC 1.-.-.-
N-ethylmaleimide reductase, FMN-linked
Gene: nemA
(*Escherichia coli* K12)
Protein accession: P77258

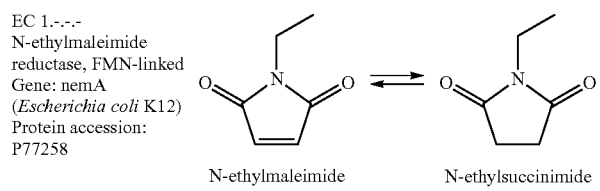

EC 1.3.99.-
Crotonobetaine reductase

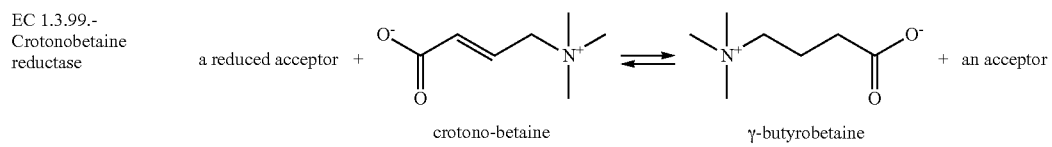

f) Conversion of 6-amino-3-hydroxyhexanoic acid into 6-amino-3-hydroxyhexanoyl-CoA As described in pathways III and IV, 6-amino-3-hydroxyhexanoic acid is converted to 6-amino-3-hydroxyhexanoyl-CoA. Although enzymes that catalyze the substrate to product conversion of 6-amino-3-hydroxyhexanoic acid into 6-amino-3-hydroxyhexanoyl-CoA (enzymatic step A6) have not been described, one skilled in the art will appreciate that the 6-amino-3-hydroxyhexanoic acid substrate is similar to substrates listed in table 5 and is likely to be an acceptable substrate for enzymes having a CoA transferase or a CoA ligase activity listed in Table 5. CoA-transferases catalyze reversible transfer reactions of Coenzyme A groups from CoA-thioesters to free carboxylic acids. Most CoA transferases operate with succinyl-CoA or acetyl-CoA as potential CoA donors and contain two different subunits.

TABLE 5

Desired substrate
product reaction
EC number
Name
Gene name (organism)
Protein accession number

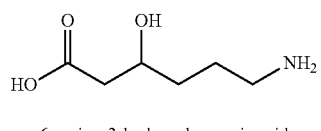

6-amino-3-hydroxyhexanoic acid

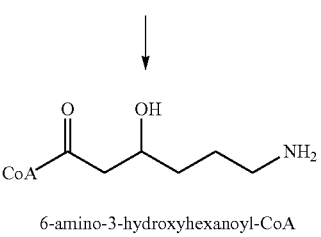

6-amino-3-hydroxyhexanoyl-CoA

EC 6.2.1.3
fatty acyl-CoA synthetase
fadD (*Escherichia coli*
K12); fadK (*Escherichia
coli* K12); ACSL1
(*Homo sapiens*); LACS7
(*Arabidopsis thaliana col*);
LACS6 (*Arabidopsis
thaliana col*); alkK
(*Pseudomonas oleovorans*)
UniProt: O15840, O30039,
O51162 O51539, O60135,
O81614, O83181, P18163,
P30624, P33121, P33124,
P39002, P39518, P44446,
P47912, P69451, P69452
P73004, P94547 Q8JZR0,
Q96338 Q96537, Q96538
Q9CHR0, Q9JTK0 Q9JYJ7,
Q9RTR4 Q9RYK3,
Q9T009 Q9T0A0, Q9X7Y5
Q9X7Z0, Q9YCF0
Q9ZBW6, Q02602 Q10776

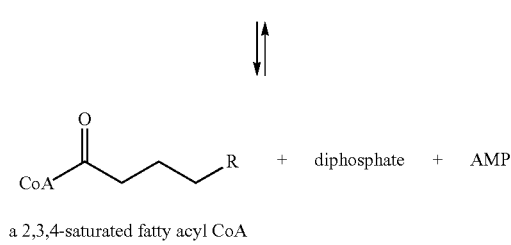

EC 6.2.1.3
acyl-CoA synthetase
LACS2 (*Arabidopsis
thaliana col*); LACS9
(*Arabidopsis thaliana
col*); LACS7
(*Arabidopsis thaliana
col*); LACS6
(*Arabidopsis thaliana col*)

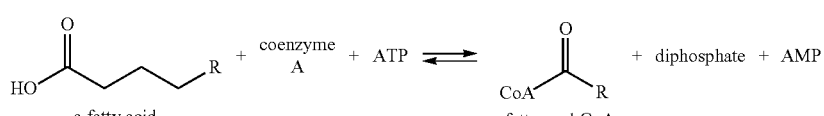

EC 6.2.1.14
6 carboxy-hexanoate-CoA
ligase
bio W (*Lysinibacillus
sphaericus*);
bio W (*Bacillus subtilis*)

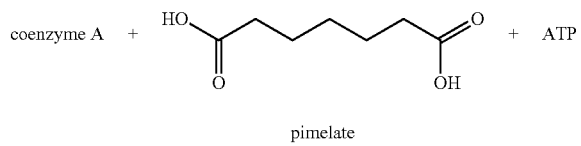

pimelate

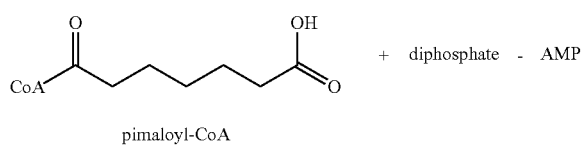

pimaloyl-CoA

TABLE 5-continued

| | | |
|---|---|---|
| EC 2.8.3.14<br>5 hydroxy-pentanoate<br>CoA-transferase | 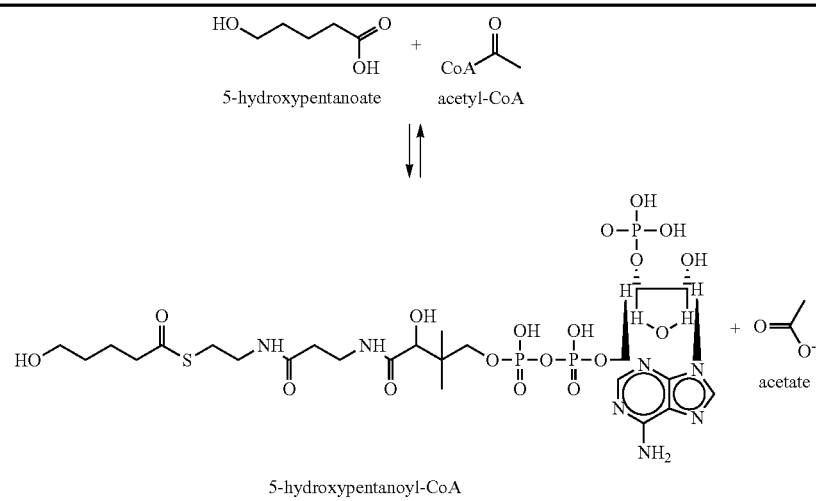 | |

5-hydroxypentanoate + acetyl-CoA ⇌ 5-hydroxypentanoyl-CoA + acetate

| | |
|---|---|
| EC 2.8.3.13<br>Succinate-hydroxymethyl-<br>glutarate CoA-transferase | 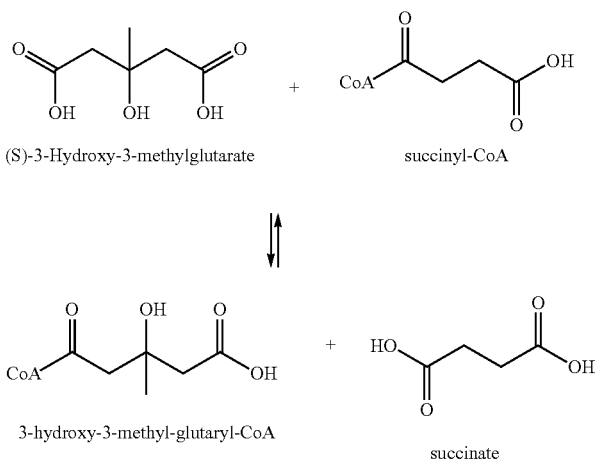 |

(S)-3-Hydroxy-3-methylglutarate + succinyl-CoA ⇌ 3-hydroxy-3-methyl-glutaryl-CoA + succinate

| | |
|---|---|
| EC 2.8.3.-<br>γ-butyrobetainyl-<br>CoA:carnitine<br>CoA transferase<br>caiB<br>(*Escherichia coli* K12) | 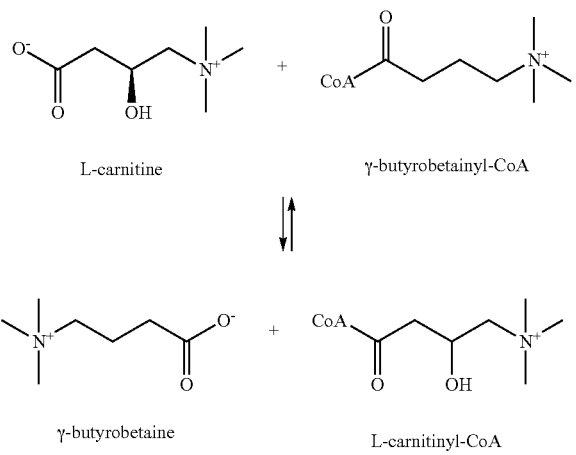 |

L-carnitine + γ-butyrobetainyl-CoA ⇌ γ-butyrobetaine + L-carnitinyl-CoA g) Conversion of 6-amino-3-hydroxyhexanoyl-CoA into 6-amino-hex-2-enoyl-CoA

In some embodiments, 6-amino-3-hydroxyhexanoyl-CoA is converted into 6-amino-hex-2-enoyl-CoA (enzymatic steps A7, pathways III and IV). Although enzymes that catalyze this conversion have not been described, one will appreciate that 6-amino-3-hydroxyhexanoyl-CoA may likely be an acceptable substrate for the dehydratase or hydro-lyase enzymes listed in Table 3. In a preferred embodiment, the reaction is catalyzed by enoyl-CoA hydratase (EC 4.2.1.17), a methyl-glutaconyl-CoA hydratase (EC 4.2.1.18), a crotonase (EC 4.2.1.55), a long-chain-enoylCoA hydratase (EC 4.2.1.74) or a 2-oxohept-3-enedioate hydrolase (EC 4.2.1-).

h) Conversion of 6-aminohex-2-enoyl-CoA to 6-aminohex-2-enoic acid

In Pathways IV and VIII, 6-aminohex-2-enoyl-CoA is converted to (E)-6-aminohex-2-enoic acid (b3 to b4 conversion, enzymatic step B4). Although enzymes that catalyze the substrate b3 to product b4 conversion of 6-aminohex-2-enoyl-CoA to (E)-6-aminohex-2-enoic acid have not been described, one skilled in the art will appreciate that the 6-aminohex-2-enoyl-CoA substrate is similar to glutaconyl CoA (see below) and the substrates listed in Table 5. Therefore 6-aminohex-2-enoyl-CoA is likely to be an acceptable substrate for enzymes having a CoA-transferase activity such as those listed below or in Table 5. Coenzyme A-transferases are a family of enzymes with a diverse substrate specificity and subunit composition. The (E)-glutaconate:acetyl-CoA CoA-transferase (EC 2.8.3.12) which catalyzes the following reaction may catalyze the substrate to product conversion of 6-aminohex-2-enoylCoA to (E)-6-aminohex-2-enoic acid:

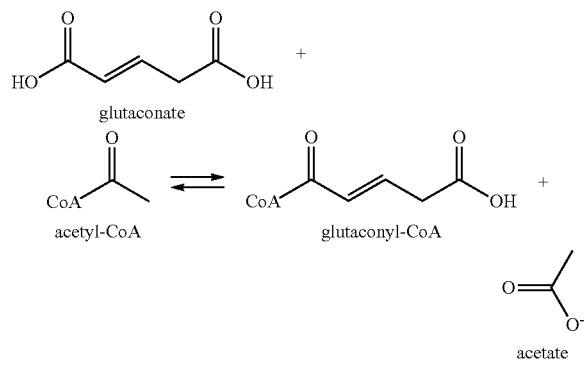

The (E)-glutaconate:acetyl-CoA CoA-transferase enzyme is part of glutamate degradation V (via hydroxyglutarate) pathway and consists of two different subunits (Subunit A and B) encoded by the GctA and GctB genes (UniProt:Q59111 and UniProt:Q59112).

i) Conversion of 6-aminohex-2-enoyl-CoA into 6-aminohexanoyl-CoA

In some embodiments, and more specifically in pathways III, V and IX, 6-aminohex-2-enoyl-CoA is converted into 6-aminohexanoyl-CoA (enzymatic step B5). Although this conversion has not been described, one will appreciate that the dehydrogenase enzymes listed in Table 4 may be able to convert 6-aminohex-2-enoyl-CoA to 6-aminohexanoyl-CoA. In a preferred embodiment, the enzymatic step B5 is catalyzed by a butyryl-CoA dehydrogenase (EC1.3.2.1, bcd, *Megasphaera elsdenii, Clostridium acetobutylicum*), a Glutaryl-CoA dehydrogenase (EC 1.3.99.7), 2-methylacyl-CoA dehydrogenase (EC 1.3.99.10, acdH *Streptomyces avermitilis*), 2-methyl branched-chain acyl-CoA dehydrogenase (acdH *Streptomyces avermitilis*), Acadsb (*Rattus norvegicus*), or a crotonobetaine reductase (EC 1.3.99.-, caiA, *Escherichia coli* K12). In another preferred embodiment, the dehydrogenase of enzymatic step B5 is an acyl-CoA dehydrogenase. Acyl-CoA dehydrogenases are a class of enzymes (EC 1.3.99.3, encoded by fadE in *Escherichia coli* K12, isovaleryl-CoA dehydrogenase encoded by aidB in *Escherichia coli* K12, encoded by acdB in *Clostridium difficile*) which catalyze the initial step in each cycle of fatty acid β-oxidation in the mitochondria of cells. Their action results in the introduction of a trans double-bond between C2 and C3 of the acyl-CoA thioester substrate. FAD is a required co-factor in the mechanism in order for the enzyme to bind to its appropriate substrate.

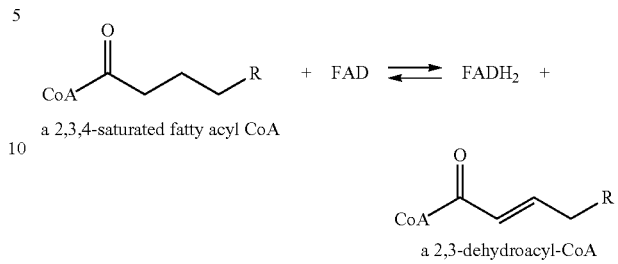

j) Conversion of 1-amino-6-hexanoyl-CoA into 6-aminohexanoic acid

In enzymatic step (B6), 1-amino-6-hexanoyl-CoA is converted to 6-aminohexanoic acid (Pathways III, V, and IX). Although enzymes that catalyze this substrate conversion have not been described, one skilled in the art will appreciate that the substrate 1-amino-6-hexanoyl-CoA is similar to the substrates listed in Table 5. Therefore, 1-amino-6-hexanoyl-CoA is likely to be an acceptable substrate for enzymes having a CoA-transferase activity, such as those listed below and in Table 5. In a preferred embodiment, the CoA-transferase enzymes belong to the EC 2.8.1.x class. A preferable CoA transferase is a 2-hydroxyisocaproate CoA transferase. 2-hydroxyisocaproate CoA transferase has been shown to catalyze the reversible conversion of 2-hydroxyisocaproate into 2-hydroxyisocaproate CoA in the reduction of L-Leucine to isocaproate pathway in *Clostridium difficile* (Kim et al., Applied and Environmental Microbiology, 2006, Vol. 72, pp 6062-6069).

k) Conversion of (S)-3,6-diaminohexanoic acid to (S)-3,6-diaminohexanoyl-CoA According to pathways I and V, (S)-3,6-diaminohexanoic acid is converted to 3,6-diaminohexanoyl-CoA (enzymatic step B2). Although enzymes that catalyze the substrate to product conversion of (S)-3,6-diaminohexanoic acid to 3,6-diaminohexanoyl-CoA have not been described, one skilled in the art will appreciate that the (S)-3,6-diaminohexanoic acid substrate is similar to substrates listed in Table 5. Therefore, (S)-3,6-diaminohexanoic acid is likely to be an acceptable substrate for enzymes having a CoA transferase or a CoA ligase activity, such as the enzymes listed in Table 5. CoA-transferases catalyze reversible transfer reactions of Coenzyme A groups from CoA-thioesters to free carboxylic acids. Most CoA transferases operate with succinyl-CoA or acetyl-CoA as potential CoA donors and contain two different subunits.

l) Conversion of 3,6-diaminohexanoyl-CoA into 6-aminohex-2-enoyl-CoA

In enzymatic step B3 (Pathways I and V), 3,6-diaminohexanoyl-CoA is converted to 6-aminohex-2-enoyl-CoA. Although enzymes that catalyze the substrate to product conversion of 3,6-diaminohexanoyl-CoA to 6-aminohex-2-enoyl-CoA have not been described, one skilled in the art will appreciate that the 3,6-diaminohexanoyl-CoA substrate is similar to substrates listed in Table 6. Therefore, 3,6-diaminohexanoyl-CoA is likely to be an acceptable substrate for enzymes having a deaminase activity, such as those listed in Table 6.

TABLE 6

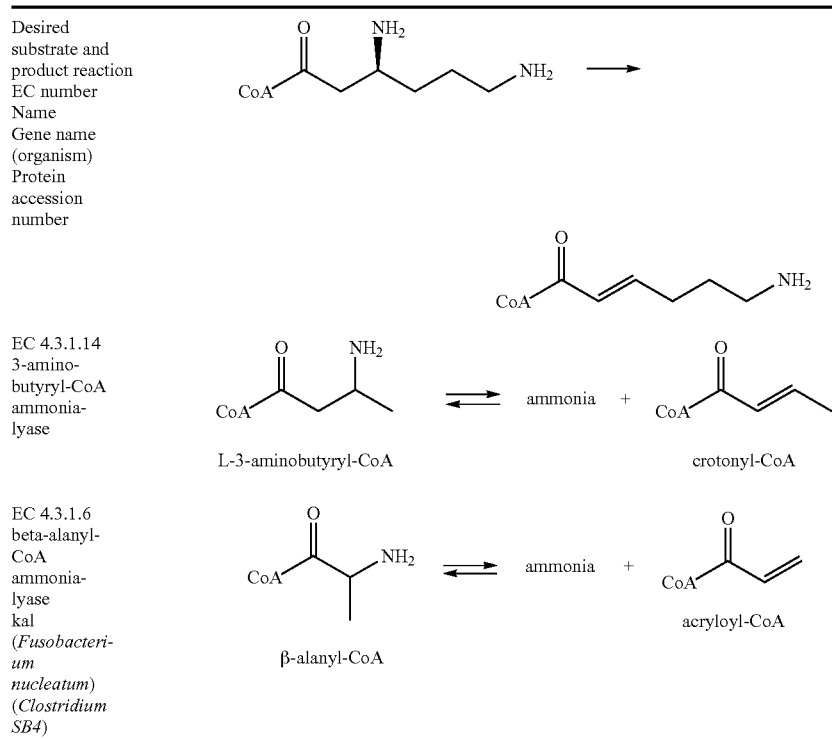

| | |
|---|---|
| Desired substrate and product reaction EC number Name Gene name (organism) Protein accession number | |
| EC 4.3.1.14 3-amino-butyryl-CoA ammonia-lyase | L-3-aminobutyryl-CoA ⇌ ammonia + crotonyl-CoA |
| EC 4.3.1.6 beta-alanyl-CoA ammonia-lyase kal (*Fusobacterium nucleatum*) (*Clostridium SB4*) | β-alanyl-CoA ⇌ ammonia + acryloyl-CoA | m) Conversion of (S)-3,6-diaminohexanoic acid into 6-aminohex-2-enoic acid

In some embodiments, (S)-3,6-diaminohexanoic acid is directly converted to 6-aminohex-2-enoic acid (enzymatic step B', Pathway VI) by a polypeptide having a deaminase activity. Although enzymes that catalyze the substrate to product conversion of 3,6-diaminohexanoate to 6-aminohex-2-enoyl have not been described, one skilled in the art will appreciate that the 3,6-diaminohexanoate substrate is similar to L-aspartate or (2S,3S)-3-methylaspartate. Therefore, 3,6-diaminohexanoate is likely to be an acceptable substrate for Methylaspartate ammonia-lyase isolated for example from *Citrobacter amalonaticus, Citrobacter freundii, Clostridium tetanomorphum*, or *Morganella morganiithat* which catalyzes the following reaction:

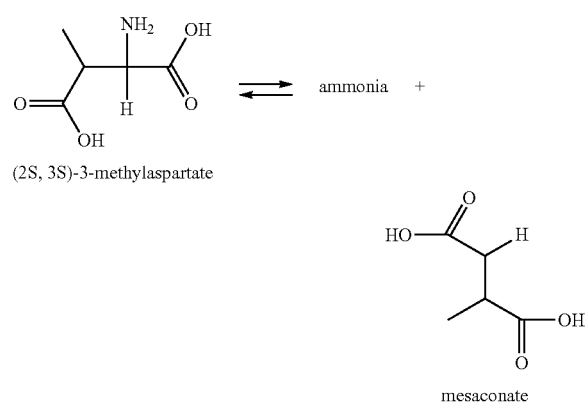

n) Conversion of lysine into 6-amino-2-oxohexanoic acid

Aspects of the invention provide metabolic pathways for the production of aminocaproic acid from lysine via a 6-amino-2-hydroxyhexanoic acid intermediate (Pathways VII, VIII and IX). As depicted in FIG. 2, lysine can be first converted to 6-amino-2-oxohexanoic acid (enzymatic step C1) and the resulting 6-amino-2-oxohexanoic acid is then converted to 6-amino-2-hydroxyhexanoic acid (enzymatic step C2). In some embodiments, the resulting 6-amino-2-hydroxyhexanoic acid can be then converted to (E)-6-amino-hex-2-enoic acid (enzymatic step C3) and finally the resulting ((E)-6-aminohex-2-enoic acid is converted to aminocaproic acid (as described in enzymatic step A5). In other embodiments, 6-amino-2-hydroxyhexanoic acid is first converted to 6-amino-2-hydroxyhexanoyl-CoA (enzymatic step C4), then into 6-aminohex-2-enoyl-CoA (enzymatic step C5) and subsequently to 6-aminohexanoic acid as described above (enzymatic steps B5 followed by B6 or enzymatic steps B4 followed by A5).

In some embodiments (enzymatic step C1), lysine is first converted to 6-amino-2-oxohexanoic acid (c1) by an aminotransferase enzyme (EC 2.6.1.x) or a dehydrogenase (EC 1.4.1.x or EC 1.4.3.x). In some embodiments, the pathway involves a lysine racemase that converts L-lysine to D-lysine, which is then converted to cyclic $\Delta^1$-piperideine-2-carboxylate intermediate which is then spontaneously converted to 6-amino-2-oxohexanoic acid in the presence of water (see FIG. 4). Lysine racemase enzymes include enzymes of the EC 5.1.1.5 class. In other embodiments, L-lysine is directly converted to cyclic $\Delta^1$-piperideine-2-carboxylate by a lysine dehydrogenase (EC 1.4.1.15, isolated from, for example, *Agrobacterium tumefaciens* or *Candida albicans*). In another embodiment, L-lysine is converted to 6-amino-2-oxohexanoic acid by a lysine-α-oxidase (EC 1.4.3.14, *Trichoderma viride* i4). Yet in other embodiments, enzymes listed in Table 7 may be used or engineered to catalyze the conversion of L-lysine to 6-amino-2-oxohexanoic acid.

TABLE 7

Desired substrate-product reaction
EC number
Name
Gene name
(organism)
Protein accession
number

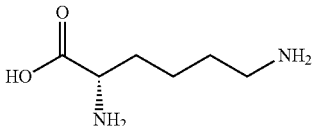

(S)-2,6-diaminohexanoic acid

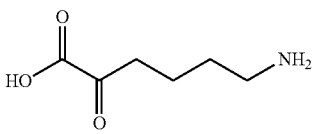

6-amino-2-oxohexanoic acid

EC 2.6.1.35
glycine-oxaloacetate
transaminase
*Micrococcus denitrificans,*
*Rhodobacter capsulatus* strain
E1F1, *Rhodopseudomonas*
*acidophila*

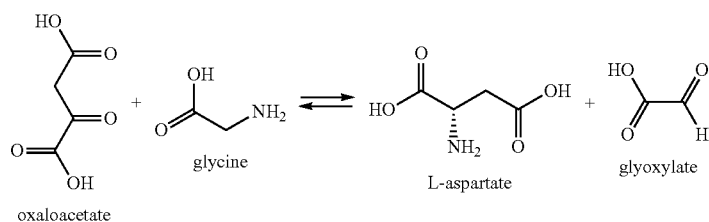

oxaloacetate    glycine    L-aspartate    glyoxylate

EC 2.6.1.42
Branched-chain amino acid
aminotransferase (transaminase B)
ilvE (*Escherichia coli* K12); ilvE
(*Methanothermobacter*
*thermautotrophics*); ilvE
(*Methanococcus aeolicus*);
BAT1 (*Saccharomyces*
*cerevisiae S288C*);
ilvE (*Pseudomonas aeruginosa*)
UniProt: O14370,
UniProt: O32954,
UniProt: O86505,
UniProt: P0AB80,
UniProt: P38891,
UniProt: P47176,
UniProt: Q9PIM6

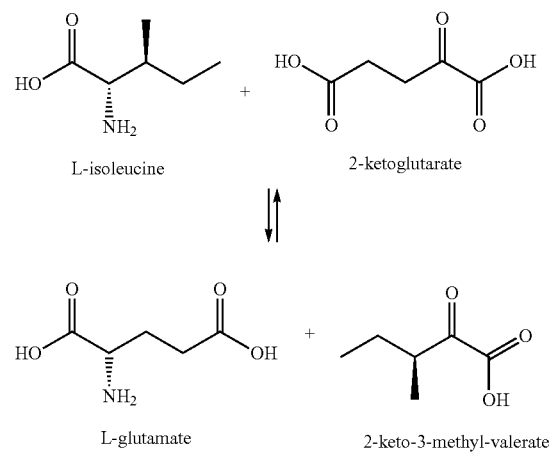

L-isoleucine    2-ketoglutarate

L-glutamate    2-keto-3-methyl-valerate

EC 2.6.1.21
D-alanine
aminotransferase
*Bacillus* sp.,*Bacillus subtilis,*
*Pisum sativum*
*Rhizobium japonicum*

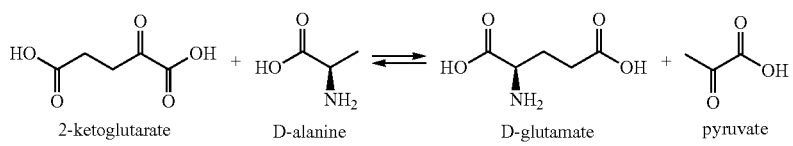

2-ketoglutarate    D-alanine    D-glutamate    pyruvate

TABLE 7-continued
EC 2.6.1.8
Diamino-acid aminotransferase
*Aspergillus fumigatus, Escherichia coli, Mus musculus*
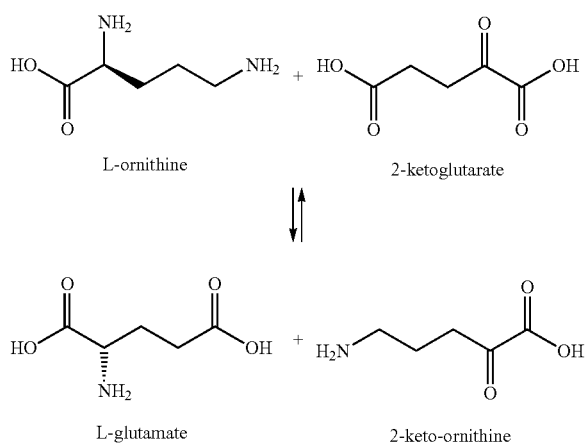
EC 2.6.1.19
β-alanine aminotransferase
*Rattus norvegicus*
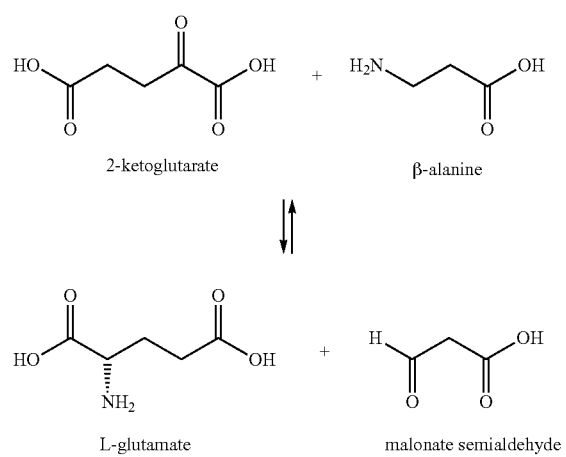
EC 2.6.1.67
2-aminohexanoate aminotransferase
*Candida guilliermondii* var. *membranaefaciens*
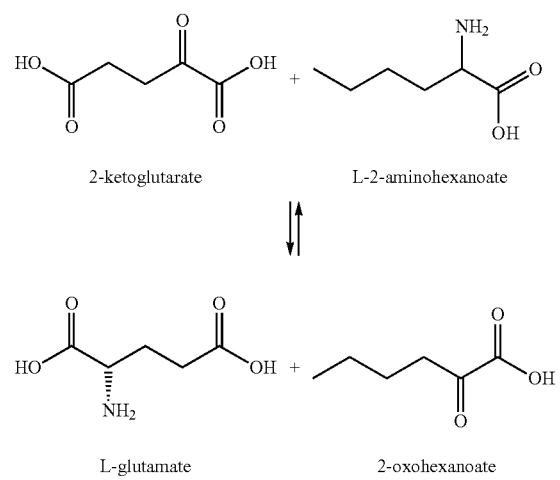

TABLE 7-continued

EC 2.6.1.22
L-3-aminoisobutyrate
aminotransferase
*Rattus norvegicus; Sus scrofa*

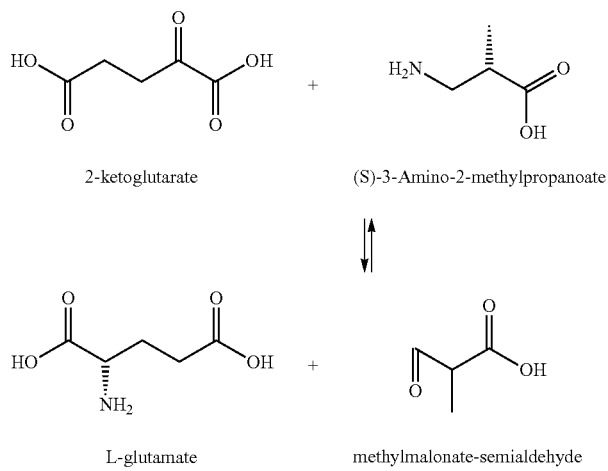

2-ketoglutarate + (S)-3-Amino-2-methylpropanoate ⇌ L-glutamate + methylmalonate-semialdehyde EC 2.6.1.12
Alanine-oxo-acid
aminotransferase
*Pseudomonas* sp.;
*Brucella abortus*

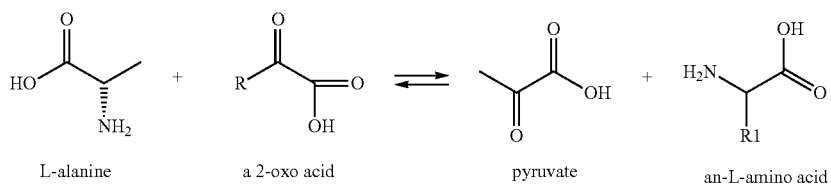

L-alanine + a 2-oxo acid ⇌ pyruvate + an-L-amino acid

EC 2.6.1.40
β-aminoisobutyrate-
pyruvate
transaminase
*Cavia porcellus, Homo sapiens,
Rattus norvegicus, Sus scrofa*

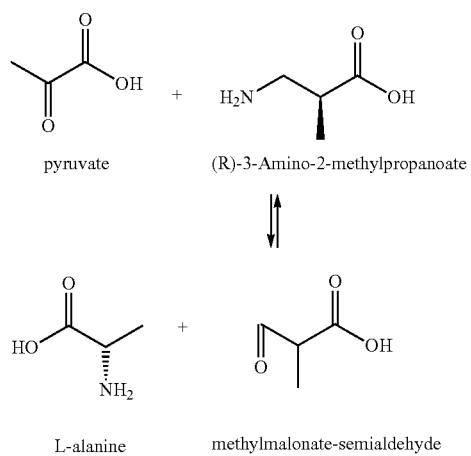

pyruvate + (R)-3-Amino-2-methylpropanoate ⇌ L-alanine + methylmalonate-semialdehyde

TABLE 7-continued

| | |
|---|---|
| EC 1.4.1.15<br>Lysine dehydrogenase<br>Piperidine-2-carboxylate is spontaneously converted to 6-amino-2-oxohexanoic acid. | 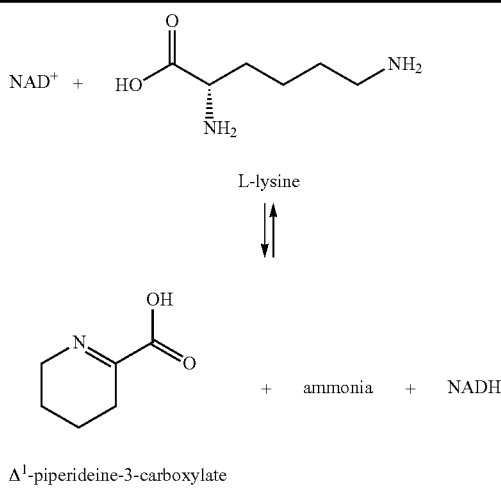 |
| EC 1.4.1.2<br>Glutamate dehydrogenase<br>GDH2, GDH1<br>(*Arabidopsis thaliana col*), gdhA<br>(*Peptoniphilus asaccharolyticus,*<br>*Halobacterium salinarum*), gdh<br>(*Thermotoga maritima*), GLUD1,<br>GLUD2 (*Homo sapiens*),<br>*Clostridium propionicum,*<br>*Bacillus subtilis* | 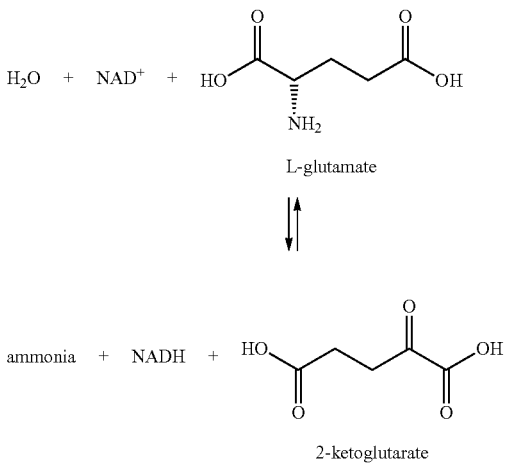 |
| EC 1.4.1.16<br>meso-diaminopimelate<br>D-dehydrogenase<br>ddh<br>(*Corynebacterium glutamicum*),<br>dapdh<br>(*Lysinibacillus sphaericus*) | 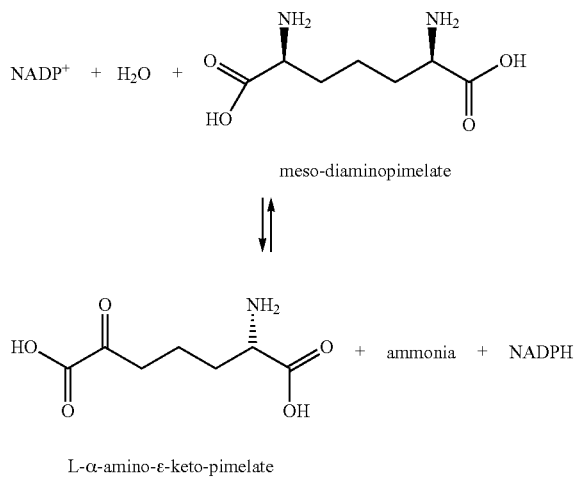 | o) Conversion of 6-amino-2-oxohexanoic acid is converted to 6-amino-2-hydroxyhexanoic acid According to enzymatic step C2, 6-amino-2-oxohexanoic acid (c1) is converted to 6-amino-2-hydroxyhexanoic acid (c2, Pathways VII, VIII and IX). In some embodiments, this reaction is catalyzed by a reductase or dehydrogenase enzyme. Although there are no known enzymes that catalyze this specific reaction, dehydrogenase enzymes capable of reducing the carboxylic group on c2 to a secondary alcohol may be considered. Examples of enzymes having, or which can be engineered to have, a 6-amino-2-oxohexanoic acid dehydrogenase activity can be isolated from a variety of sources and include, but are not limited to, the enzymes listed in Table 8.

TABLE 8

Desired substrate-product reaction
EC number
Name
Gene name (organism)
Protein accession number

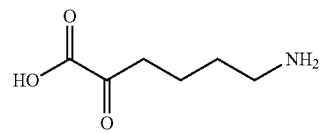

6-amino-2-oxohexanoic acid

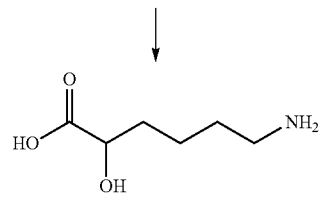

6-amino-2-hydroxyhexanoic acid

EC 1.1.1.5
diacetyl reductase
budC (*Enterobacter aerogenes*); budC (*Klebsiella pneumoniae*); butA (*Corynebacterium glutamicum*)

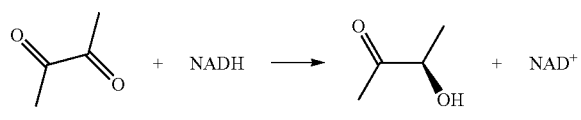

diacetyl          acetoin

EC 1.1.1.26
Glycolate reductase

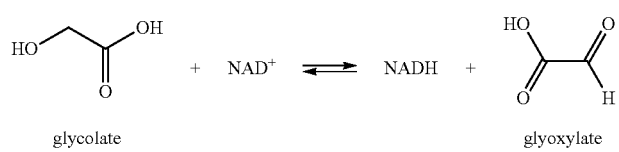 [SMILES: O=C(O)CO ; "NAD+" ; "NADH" ; O=CC(=O)O]

glycolate          glyoxylate

EC 1.1.1.27
L-lactate dehydrogenase
ldh (*Streptococcus mutans*); ldh2 (*Bifidobacterium longum*); Ldha (*Rattus norvegicus*), ldh (*Lactobacillus casei*); ldh (*Mycoplasma pneumoniae M129*); ldh (*Thermotoga maritima*)
UniProt: O23569, O81272, P00336, P00337, P00338, P00339, P00340, P00341, P00342, P00343, P00344, P00345, P04034, P04642, P06150, P06151, P07195, P07864, P0C0J3, P10655, P13490, P13491, P13714, P13715, P13743, P14561, P16115, P16125, P19629, P19858, P19869, P20373, P20619, P22988, P22989, P26283, P29038, P33232, P33571, P42119, P42120, P42121, P42123, P46454, P47698, P50933, P56511, P56512, Q7M1E1, Q96570, Q9CGG8, Q9CII4, Q9PNC8, Q01462, Q06176, Q07251, Q27888, Q48662, Q59244, Q60009, Q60176, Q62545, Q96569, Q9SBE4, Q9ZRJ5

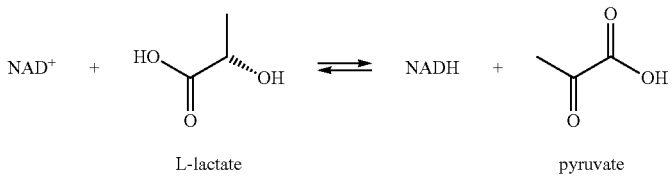

L-lactate          pyruvate

TABLE 8-continued

EC 1.1.1.37
malate dehydrogenase
mdh (*Escherichia coli K12*); MDH1 (*Homo sapiens*), MDH2 (*Homo sapiens*), malate dehydrogenase (*Propionibacterium freudenreichii* subsp. *shermanii*); malate dehydrogenase 1 MDH1 (*Homo sapiens*); MDH1(*Sus scrofa*); mdh *Mycobacterium tubercolosis*); malate dehydrogenase (*Methanococcus maripaludis*), malate dehydrogenase (*Aquifex pyrophilus*); mdh (NAD-linked) (*Methylobacterium extorquens* AM1)
UniProt O24047, O48903, O48904, O48905, :O48906, O65363, O65364, O81278, O81279, O81609, P04636, P10887, P11386, P11708, P14152, P16142, P17505, P17783, P19446, P19977, P19978, P19979, P19980, P19981, P19982, P19983, P22133, P25077, P32419, P33163, P44427, P46487, P46488, P49814, P50917, P58408, P93106, Q7M4Y9, Q7M4Z0, Q8R1P0, Q93ZA7, Q9PHY2, Q9SN86, Q9XTB4, Q9ZP05, Q9ZP06, Q04820, Q07841, Q42686, Q42972, Q43743, Q43744, Q49981, Q55383, Q58820, Q59202

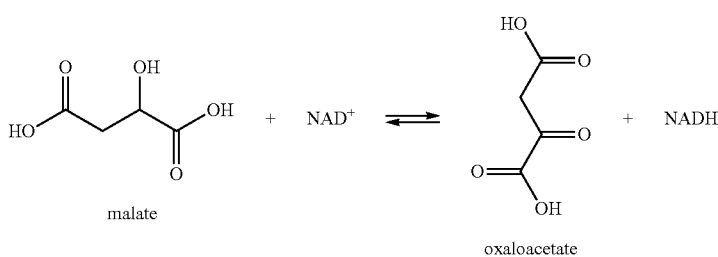

EC 1.1.1.93
tartrate dehydrogenase
*Pseudomonas putida*

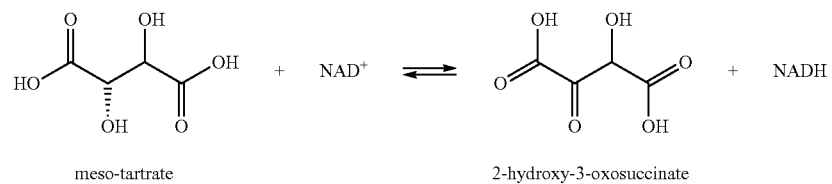

EC 1.1.1.110
Indole-3-lactate dehydrogenase
*Clostridium sporogenes*;
*Lactobacillus casei*

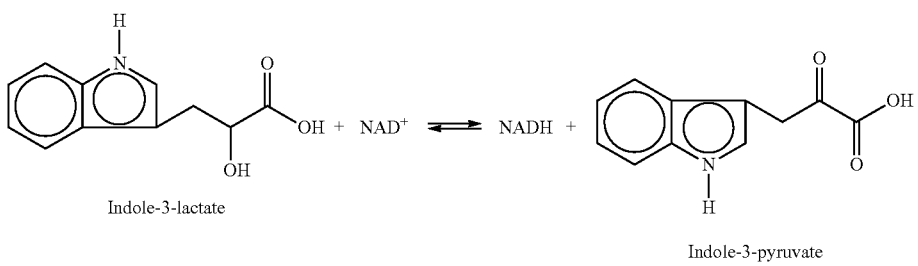

TABLE 8-continued

EC 1.1.1.111
3-(imidazol-5-yl)lactate
dehydrogenase
imidazole-lactate
oxidase (*Comamonas
testosteroni*); imidazol-
pyruvate reductase
(*Escherichia coli* B)

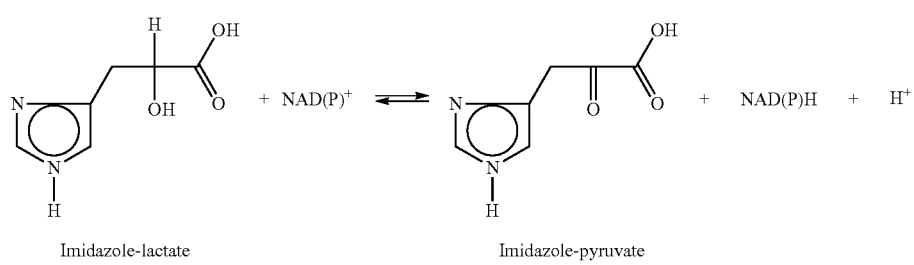

Imidazole-lactate            Imidazole-pyruvate

EC 1.1.1.125
2-deoxy-D-gluconate
3-dehydrogenase
kduD (*Escherichia
coli*)
UniProt P37769
(*Escherichia coli*)

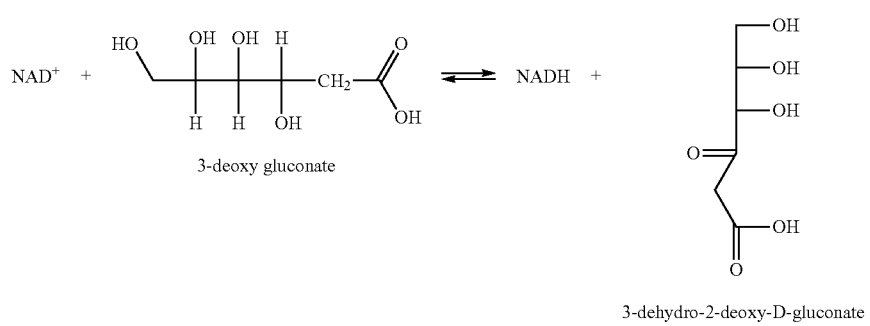 [SMILES: "NAD+" ; O=C(O)CC(O)C(O)C(O)CO ; "NADH" ; O=C(O)CC(=O)C(O)C(O)CO]

3-deoxy gluconate          3-dehydro-2-deoxy-D-gluconate

EC 1.1.1.167
Hydroxymalonate
dehydrogenase

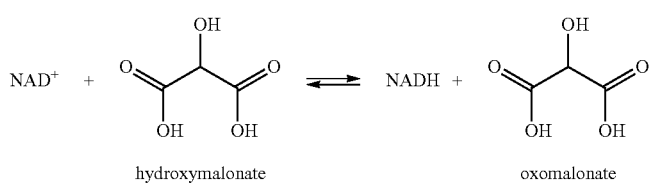 [SMILES: "NAD+" ; O=C(O)C(O)C(=O)O ; "NADH" ; O=C(O)C(O)C(=O)O]

hydroxymalonate        oxomalonate

EC 1.1.1.169
2-dehydropantoate 2-
reductase
panE (*Escherichia coli
K12*)
UniProt: Q9CFY8
(*Streptococcus lactis*),
Q9V0N0 (*Pyrococcus
abyssi*)

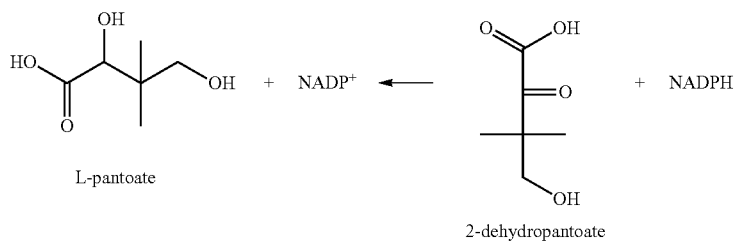

L-pantoate          2-dehydropantoate

EC 1.1.1.172
2-oxoadipate reductase

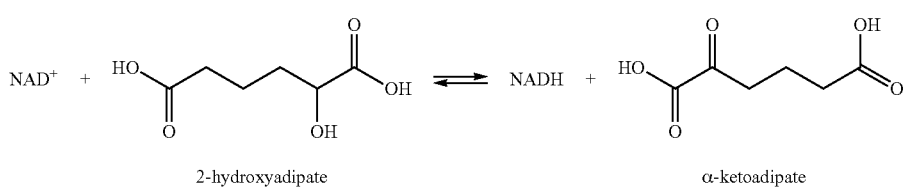 [SMILES: "NAD+" ; O=C(O)CCCC(O)C(=O)O ; "NADH" ; O=C(O)CCCC(=O)C(=O)O]

2-hydroxyadipate         α-ketoadipate

EC 1.1.1.215
Gluconate 2-
dehydrogenase
ghrB (*Escherichia coli
K12*)

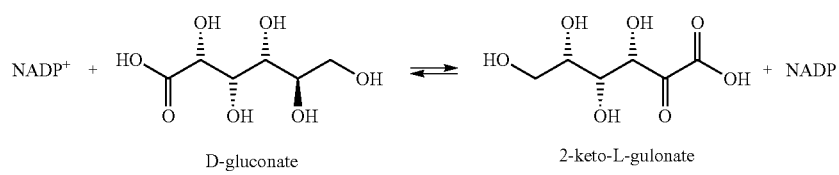

D-gluconate         2-keto-L-gulonate

TABLE 8-continued

| EC 1.1.1.222 (R)-4-(hydroxyphenyl)lactate dehydrogenase | 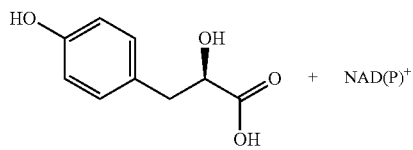 |

(R+)-3-(4-hydroxyphenyl)lactate

⇅

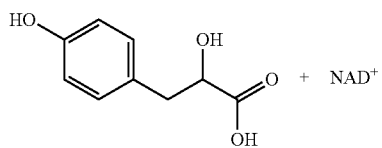

4-hydroxyphenylpyruvate

| EC 1.1.1.237 hydroxyphenylpyruvate reductase HPPR (*Solenostemon scutellarioides*) | |

4-hydroxyphenyllactate

⇅

4-hydroxyphenylpyruvate

| EC 1.1.1.272 (R)-2-hydroxyacid dehydrogenase | 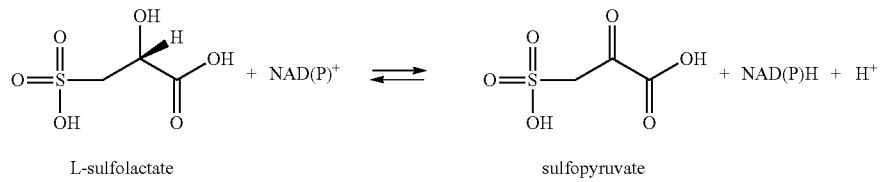 |

L-sulfolactate         sulfopyruvate

| EC 1.1.1.285 3"-deamino-3"-oxonicotianamine reductase or deoxymugineic acid synthase ZmDMAS1 (*Zea mays*), TaDMAS1 (*Triticum aestivum*) hvDMAS1 (*Hordeum vulgare*), OsDMAS1 (*Oryza*), 3"-deamino-3"-oxonicotianamine reductase (*Hordeum vulgare*) | 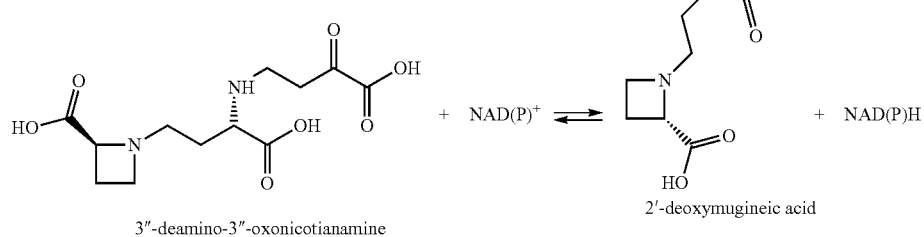 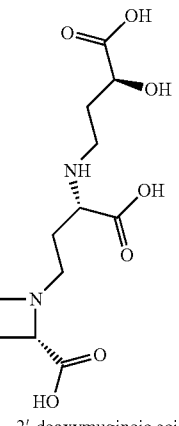 |

3"-deamino-3"-oxonicotianamine         2'-deoxymugineic acid

TABLE 8-continued

| | |
|---|---|
| EC 1.1.1.- oxalosuccinate reductase icd (*Hydrogenobacter thermophilus*) | 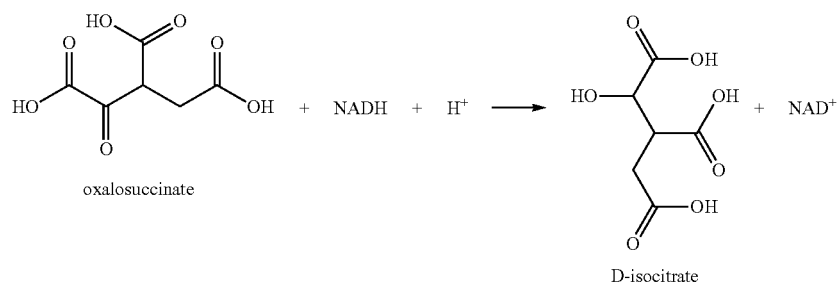 |
| EC 1.1.99.2 α-ketoglutarate reductase serA (*Escherichia coli* K12) | 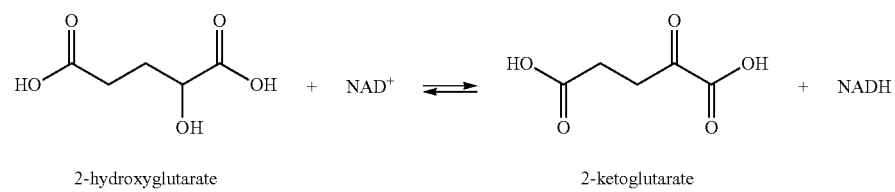 |
| EC 1.1.99.3 D-gluconate dehydrogenase (*Pseudomonas fluorescens*) UniProt: O34213, O34214, O34215, Q9PI91 | 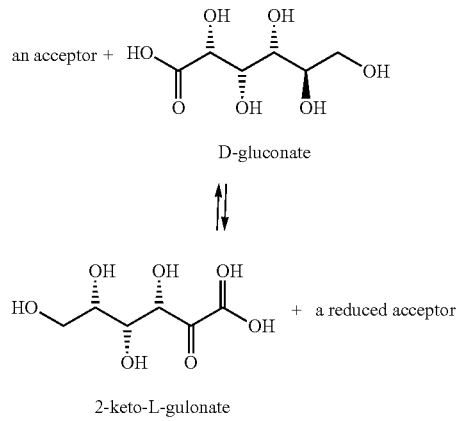 |
| EC 1.1.99.6 D-2-hydroxy-acid dehydrogenase Ddh (*Zymomonas mobilis*), ddh (*Haemophilus influenzae*); *Synechocystis sp.*, GRHPR (*Homo sapiens*) UniProt: P30799, P44501, P74586, Q9UBQ7 | 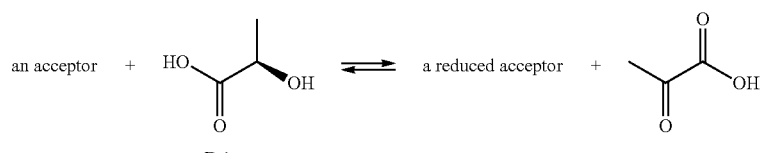 | p) Conversion of 6-amino-2-hydroxyhexanoic acid to (E)-6-amino-hex-2-enoic acid

In enzymatic step C3 (Pathway VIII), 6-amino-2-hydroxyhexanoic acid is converted to (E)-6-amino-hex-2-enoic acid by an enzyme having a dehydratase activity. Enzymatic reactions that produce enzymes having a dehydratase activity are part of the lyase class that catalyzes the removal of $H_2O$, leaving a double bond as depicted in FIG. 2. Polypeptides having dehydratase activity as well as nucleic acid encoding such polypeptides can be obtained from various species including, without limitation, *Escherichia coli* K12; *Bacillus subtilis*, *Eubacterium barkeri*, *Glycine max*, *Anthracobia melaloma*, *Plicaria anthracina* and *Plicaria leiocarpa*. Polypeptides having a dehydratase activity as well as nucleic acid encoding such polypeptides include, but are not limited to, enzymes listed in Table 3, and to enzymes EC 4.2.1.x, for example, EC 4.2.1.67 (D-fuconate hydratase), EC 4.2.1.68 (L-fuconate hydratase), EC 4.2.1.85 (dimethylmaleate hydratase), EC 4.2.1.-(crotonobetainyl-CoA hydratase) and EC 4.2.1.2 (Fumarate hydratase).

q) Conversion of 6-amino-2-hydroxyhexanoic acid is first converted to 6-amino-2-hydroxyhexanoyl-CoA In some embodiments, 6-amino-2-hydroxyhexanoic acid is first converted to 6-amino-2-hydroxyhexanoyl-CoA by a CoA transferase or a CoA ligase (enzymatic step C4, Pathways VIII and IX). Enzymes capable of catalyzing this reaction can be any suitable enzyme having a CoA transferase activity or a CoA ligase activity and include, but are not limited to, the enzymes listed in Table 5.

r) Conversion of 6-amino-2-hydroxyhexanoyl-CoA to (E)-6-aminohex-2-enoyl-CoA Subsequently, 6-amino-2-hydroxyhexanoyl-CoA can be converted to (E)-6-aminohex-2-enoyl-CoA by an enzyme having a dehydratase activity (enzymatic step C5, Pathways VIII and IX). Polypeptides having a dehydratase activity as well as nucleic acids encoding such polypeptides include, but are not limited to, the enzymes listed in Table 3 and the following enzymes: EC 4.2.1.17 (enoyl-CoA hydratase or (3S)-3-hydroxyacyl-CoA hydro-lyase), EC 4.2.1.18 (methylglutaconyl-CoA hydratase or (S)-3-hydroxy-3-methylglutaryl-CoA hydro-lyase), EC 4.2.1.55 (Crotonase or 3-hydroxybutyryl-CoA dehydratase), EC 4.2.1.54 (lactyl-CoA dehydratase isolated in *Clostridium propionicum*), EC 4.2.1.56 (itaconyl-CoA hydratase isolated in *Pseudomonas* sp.), and to EC 4.2.1.-(2-Hydroxyglutaryl-CoA dehydratase). For example, the 2-Hydroxyglutaryl-CoA dehydratase (HgdAB, CompD) catalyzes the syn-elimination of water from (R)-2-hydroxyglutaryl-CoA to (E)-glutaconyl-CoA as shown below:

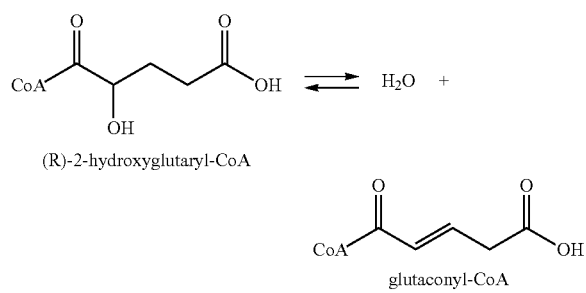

(R)-2-hydroxyglutaryl-CoA glutaconyl-CoA

Figure 4:
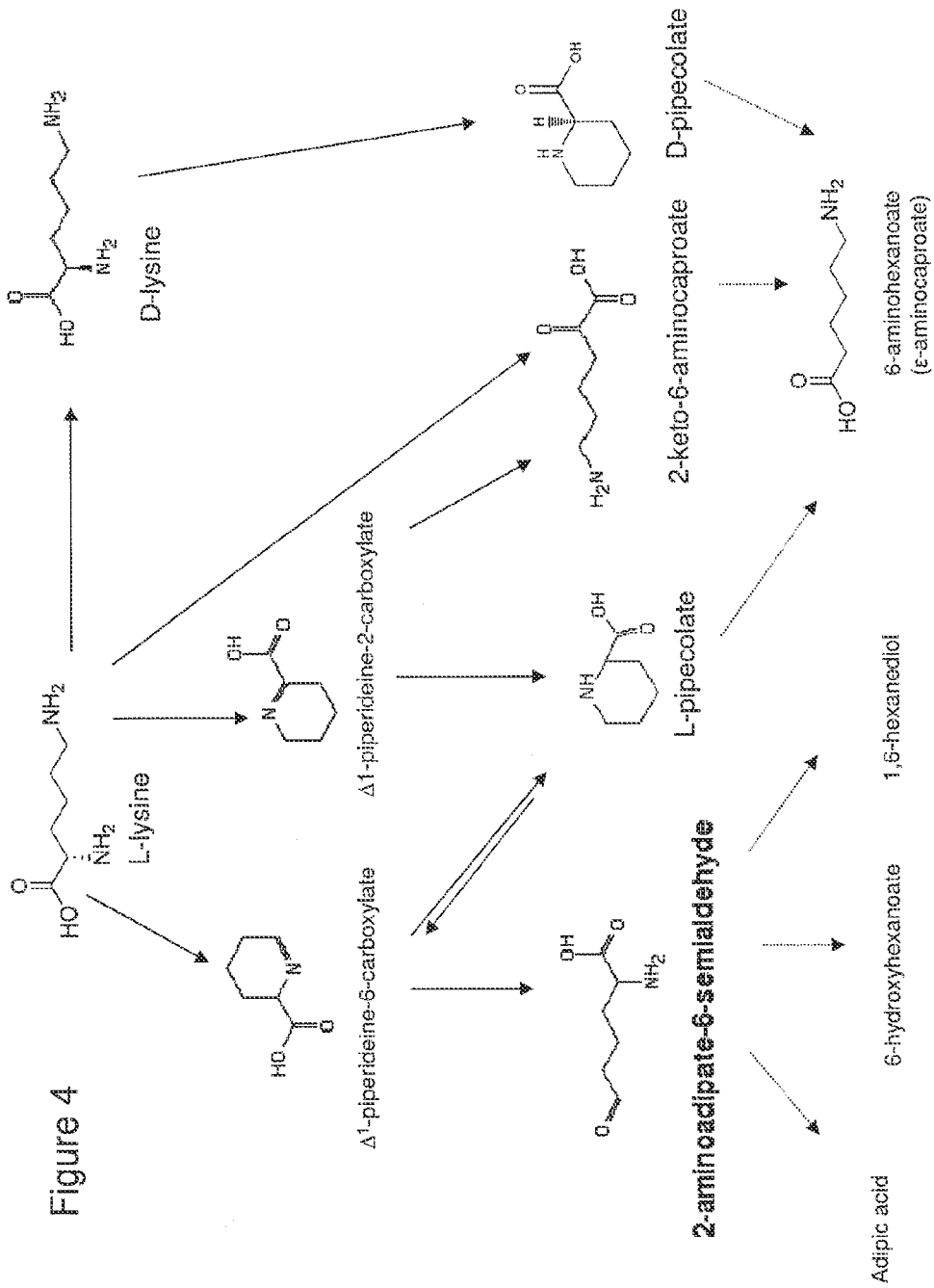
FIG. 4 represents a flow diagram of C6 difunctional hexanes from lysine via an N-heterocyclic ring intermediate.

C. Engineered Pathways for the Production of Aminocaproic Acid from a Nitrogen-Containing Heterocyclic Ring Aspects of the invention relate to the bioproduction of C6 and C5 difunctional alkanes from nitrogen containing heterocyclic rings. A nitrogen-containing heterocyclic ring includes but is not limited to piperidine, pyridine, picolinate and pipecolate. A preferable nitrogen-containing heterocyclic ring is L-2,3-dihydropicolinate (also known as (S)-2,3-dihydropyridine-2,6-dicarboxylic acid), L-2,3,4,5,-terahydrodipicolinate (also know as Δ¹-piperideine-2,6-dicarboxylate or (S)-2,3,4,5-terahydropyridin-2,6-dicarboxylic acid), Δ¹-piperideine-2-dicarboxylate, Δ¹-piperideine-6-dicarboxylate, 5,6-dihydropyridine-2-carboxylic acid, L-pipecolate and D-pipecolate. On skilled in art will understand that some of these nitrogen-containing heterocyclic rings are intermediates metabolites in the L-lysine biosynthesis pathway or in the L-lysine or D-lysine degradation pathways. For example, L-2,3-dihydropicolinate and Δ¹-piperideine-2,6-dicarboxylate are intermediate metabolites in the lysine biosynthesis pathways I, II, III, and VI. L-pipecolate, Δ¹-piperideine-6-carboxylate, and Δ¹-piperideine-2-carboxylate are intermediate metabolites in the L-lysine or D-lysine degradation pathway. In some embodiments, the bioconversion of lysine to Δ¹-piperideine-2-carboxylate is catalyzed by a lysine dehydrogenase (FIG. 4, EC 1.4.1.15).

Some aspects of the invention provide engineered metabolic pathways for the production of 6-amino-2-oxohexanoic acid from L-2-3-dihydrodipicolinate, an intermediate metabolite of the lysine biosynthetic pathway. Six lysine biosynthetic pathways have been described in bacteria, most algae, fungi and higher plants. These pathways are divided into the diaminopimelate pathways, and the α-aminoadipate pathways. In the pathways that belong to the diaminopimelate group, lysine is produced from aspartate (along with methionine, threonine and isoleucine). All of these pathways share the first enzymatic steps, and in particular the three steps required for conversion of L-aspartate to L-2,3-dihydrodipicolinate (and to tetrahydrodipicolinate). In the diaminopimelate pathway, L-aspartate is first converted to L-aspartyl-4-phosphate by an aspartate kinase (or aspartokinase), and then to L-aspartate semialdehyde (aspartate semialdehyde dehydrogenase) and finally to L-2,3-dihydrodipicolinate (dihydrodipicolinate synthase). Polypeptides having an aspartate kinase activity may be isolated from a variety of sources. Some example of suitable aspartate kinases and genes encoding for aspartate kinases are available from a variety of sources including, but not limited to, lysC (*Escherichia coli* K12), thrA (*Escherichia coli* K12), metL (*Escherichia coli* K12), AT3G02020 (*Arabidopsis thaliana* col), yclM (*Bacillus subtilis*), lysCβ, lysCα (*Bacillus subtilis*), lysCβ, lysCα (*Corynebacterium glutamicum*) and aspartokinase (*Chromohalobacter salexigens*). Polypeptides having an aspartate semialdehyde dehydrogenase activity, and genes encoding enzymes having an aspartate semialdehyde dehydrogenase activity, may be isolated from a variety of sources such as asd from *Escherichia coli* K12. Polypeptides having a dihydropicolinate synthase activity, and genes encoding enzymes having a dihydropicolinate synthase activity, may be isolated from a variety of sources. Some example of suitable dihydrodipicolinate synthase, and genes encoding for dihydrodipicolinate, are available from a variety of sources and include, but are not limited to, dapA (*Escherichia coli* K12), dapA (*Glycine max*), dapA (*Bacillus licheniformis*) and dapA (*Corynebacterium glutamicum*).

One should appreciate that, according to some aspects of the invention, at least one of the genes for the lysine biosynthetic pathway or the lysine degradation pathway is functionally inactivated in the host cell. In a preferred embodiment, host cells may be microorganisms synthesizing less than 50%, less 40%, less than 30%, less than 20%, and preferably less than 10% of the amount of lysine naturally formed under the same conditions (e.g., in a host cell having an unmodified lysine biosynthetic and/or degradation pathway). In some embodiments, C6 and C5 difunctional alkanes are produced from L-2,3-dihydropicolinate and 5,6-dihydropyridine-2-carboxylic acid. Preferably, at least one of the following enzymes is inactivated at the genetic level: Dihydrodipicolinate reductase (EC 1.3.1.26, dapB gene), 2,3,4,5-tetrahydropyridine-2-carboxylate N-succinyltransferase (also known as Tetrahydrodipicolinate succinylase, EC 2.3.1.117, dapD gene), L,L-diaminopimelate aminotransferase (E.C. 2.6.1.83, AT4G33680 gene, Hudson et al, 2006, Plant Physiol. 140(1):292-301; the enzyme was shown to be involved in lysine biosynthesis under physiological conditions by functional complementation of the *E. coli* lysine biosynthesis double mutant of dapD and dapE), or Tetrahydrodipicolinate N-acetyltransferase (EC 2.3.1.89, ykuQ (*Bacillus subtilis*)). In other embodiments, C6 and C5 difunctional alkanes are produced from $\Delta^1$-piperideine-2,6-dicarboxylate and preferably at least one of the following enzymes is inactivated at the genetic level: 2,3,4,5-tetrahydropyridine-2-carboxylate N-succinyltransferase, L,L-diaminopimelate aminotransferase, Tetrahydrodipicolinate N-acetyltransferase, or Diaminopimelate dehydrogenase (EC 1.4.1.16, ddh (*Corynebacterium glutamicum*), dapdh (*Lysinibacillus sphaericus*)). Accordingly, aspects of the invention provide a recombinant microorganism having an engineered metabolic pathway for the production of C6 and C5 difunctional alkanes from L-2,3 dihydropicolinate.

Figure 3A:
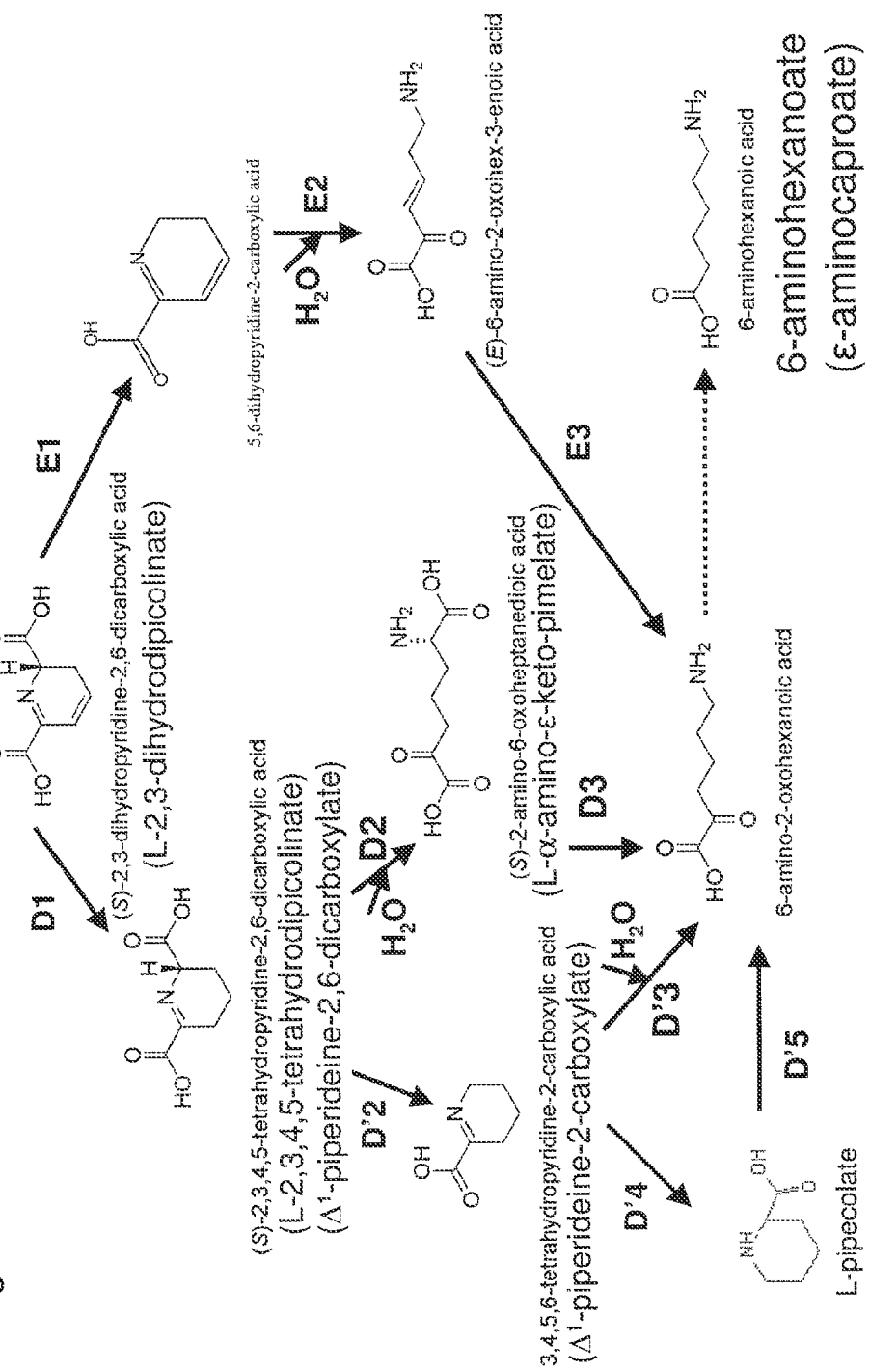
FIG. 3A represents a flow diagram for the bioproduction of aminocaproic acid from L-2,3-dihydrodipicolinate.
Figure 3B:
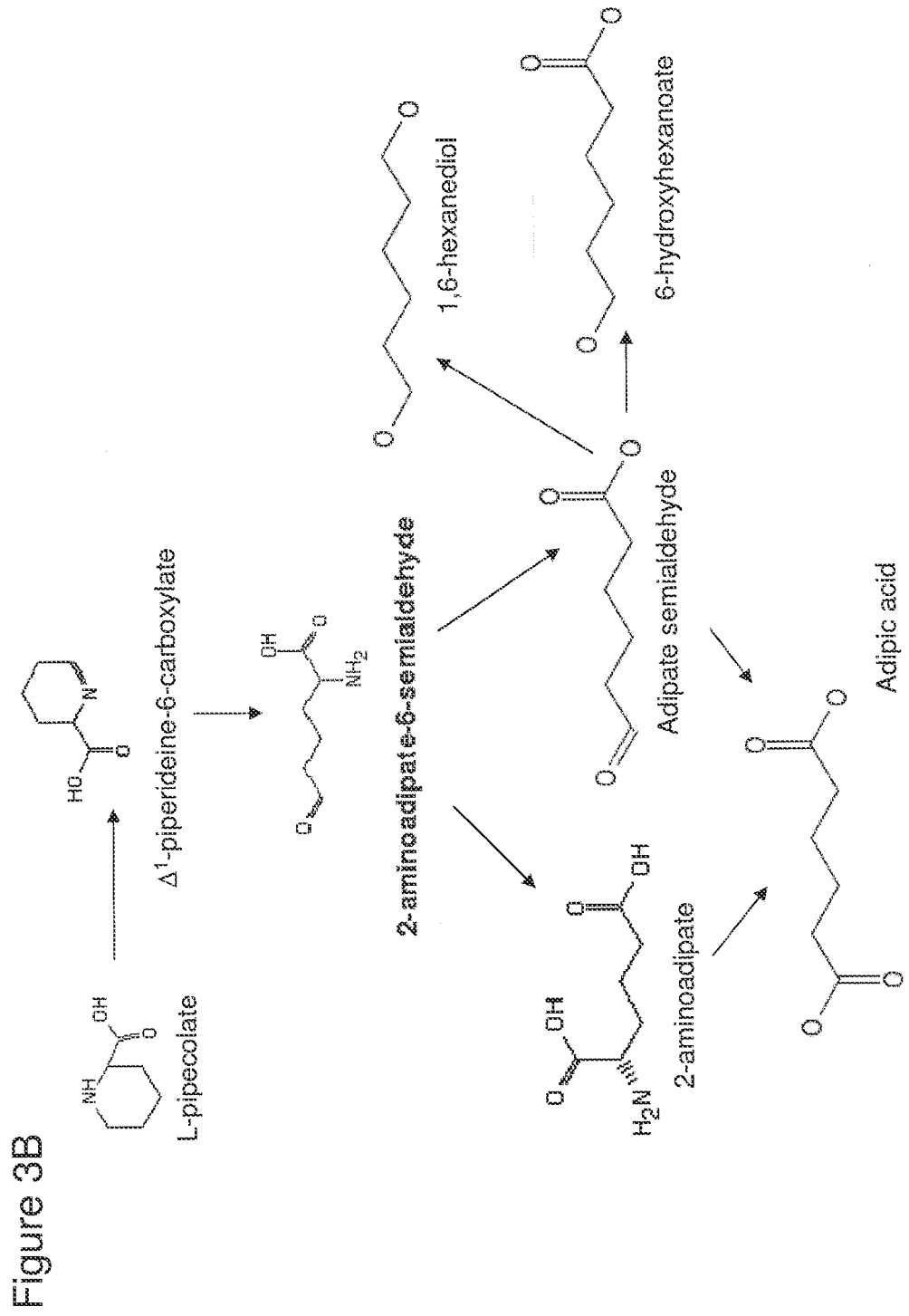
FIG. 3B represents a flow diagram for the bioproduction of adipic acid, 1,6-hexanediol, and 6-hydroxyhexanoate from L-pipecolate.

In some aspects of the invention, C5 and C6 difunctional alkanes are produced from $\Delta^1$-piperideine-2,6-dicarboxylate. In a preferred embodiment, 6-aminocaproate, adipic acid, 1,6-hexanediol and 6-hydroxyhexanoate are produced (FIGS. 3A and 3B).

Some aspects of the invention provide engineered metabolic pathways (Pathway D, Pathway D' and Pathway E, FIG. 3A) for the production of 6-amino-2-oxohexanoic acid from L-2,3-dihydrodipicolinate.
  a) As depicted in Pathway D (FIG. 3A) L-2,3,dihydrodipicolinate is first converted to $\Delta^1$-piperidine-2,6-dicarboxylate (also known as L-2,3,4,5-tetrahydrodipicolinate, enzymatic step D1), the resulting $\Delta^1$-piperidine-2,6-dicarboxylate is converted to L-α-amino-ε-ketopimelate (step D2), and the resulting L-α-amino-ε-ketopimelate is converted to 6-amino-2-oxohexanoic acid (enzymatic step D3). One should appreciate that 6-amino-2-oxohexanoic acid can be produced directly from lysine by a L-lysine α-oxidase (FIG. 4, EC 1.4.3.14, *Trichoderma viride* i4).
  b) As depicted in Pathway D' (FIG. 3A): L-2,3-dihydrodipicolinate is first converted to Δ1-piperidine-2,6-dicarboxylate (also known as L-2,3,4,5-tetrahydrodipicolinate, enzymatic step D1), the resulting $\Delta^1$-piperidine-2,6-dicarboxylate is then converted to $\Delta^1$-piperidine-2-carboxylate (enzymatic step D'2), and the resulting $\Delta^1$-piperidine-2-carboxylate is converted to 6-amino-2-oxohexanoic acid (step D'3). In an alternative pathway, $\Delta^1$-piperidine-2-carboxylate may be first converted to L-pipecolate (enzymatic step D'4) and then to 6-amino-2-oxohexanoic acid (enzymatic step D'5).
  c) As depicted in Pathway E (FIG. 3A): L-2,3-dihydrodipicolinate is first converted to 5,6-dihydropyridine-2-carboxylic acid (enzymatic step E1); the resulting 5,6-dihydropyridine-2-carboxylic acid is then converted to (E)-6-amino-2-oxohex-3-enoic acid (step E2) and the resulting (E)-6-amino-2-oxohex-3-enoic acid is converted to 6-amino-2-oxohexanoic acid (enzymatic step E3).

One will appreciate that the final steps of all pathways D, D' and E may be identical to the conversion of 6-amino-2-oxohexanoic acid to aminocaproic acid as described above (enzymatic step C2→C3→A5 or C2→C4→C5→B5→B6, or C2-4→C5→134→A5).

a) Conversion of L-2,3-dihydrodipicolinate to $\Delta^1$-piperidine-2,6-dicarboxylate (enzymatic step D1)

In some embodiments, L-2,3-dihydrodipicolinate may be converted to A1-piperidine-2,6-dicarboxylate (or tetrahydropicolinate) by action of an enzyme such as a dihydrodipicolinate reductase (belonging to EC 1.3.1.26, enzymatic step D1) that catalyzes the following chemical reaction in the lysine biosynthesis pathway:

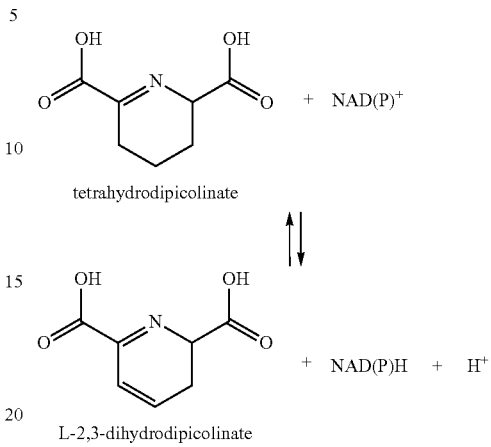

Polypeptides having a dihydrodipicolinate reductase activity, and genes encoding enzymes having a dihydrodipicolinate reductase activity, may be isolated from a variety of sources and include, but are not limited to, dapB from *Escherichia coli* K12, dapB from *Bacillus subtilis*, dapB from *Corynebacterium glutamicum*, dapB from *Mycobacterium tuberculosis* and dihydrodipicolinate reductase from *Zea mays*.

b) Conversion of $\Delta^1$-piperidine-2,6-dicarboxylate to 6-amino-2-oxohexanoic acid via a $\Delta^1$-piperidine-2-carboxylate intermediate (enzymatic steps D'2→D'3)

In some embodiments, $\Delta^1$-piperidine-2,6-dicarboxylate (or tetrahydropicolinate) is then converted to $\Delta^1$-piperidine-2-carboxylate (or 3,4,5,6-tetrahydropyridine-2-carboxylic acid) by action of a decarboxylase. Although there are no known enzymes having a $\Delta^1$-piperidine-2,6-dicarboxylate decarboxylase activity, polypeptides capable of removing carboxyl groups from aromatic rings may be used. The $\Delta^1$-piperidine-2-carboxylate ring can then spontaneously open in the presence of water to produce 6-amino-2-oxohexanoic acid as depicted below in the lysine degradation pathways V and VII.

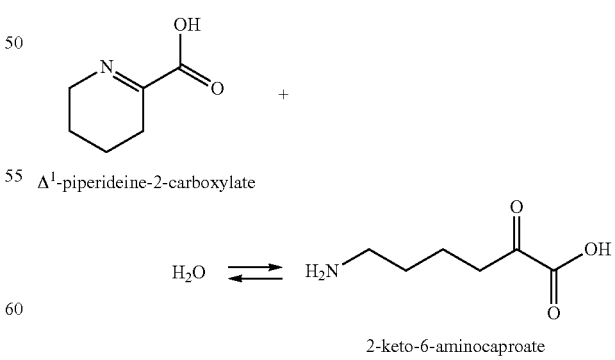

Examples of enzymes having a decarboxylase activity include, but are not limited to, 3-hydroxy-2-methylpyridine-4,5-dicarboxylate 4-decarboxylase (EC 4.1.1.51), benzoylformate decarboxylase (EC 4.1.1.7) and 2,3-dihydrobenzoic acid decarboxylase (See U.S. Pat. No. 6,440,704). 3-hydroxy-2-methylpyridine-4,5-dicarboxylate 4-decarboxylase has been identified in *Mesorhizobium loti* and in *Pseudomonas* sp. MA-1.

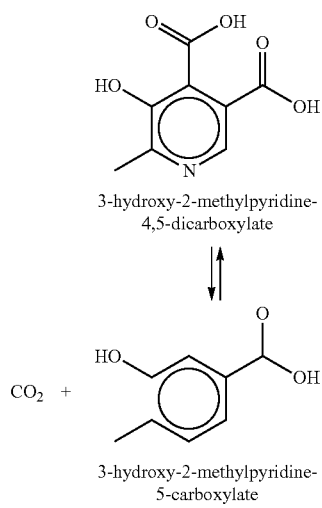

3-hydroxy-2-methylpyridine-4,5-dicarboxylate $CO_2$ +

3-hydroxy-2-methylpyridine-5-carboxylate

Benzoylformate decarboxylase (catalyzing the reaction as shown below) and the genes encoding such polypeptides may be found in a variety of species including, but not limited to, *Pseudomonas fluorescens* and *Pseudomonas putida* (gene mdlC, UniProt:P20906).

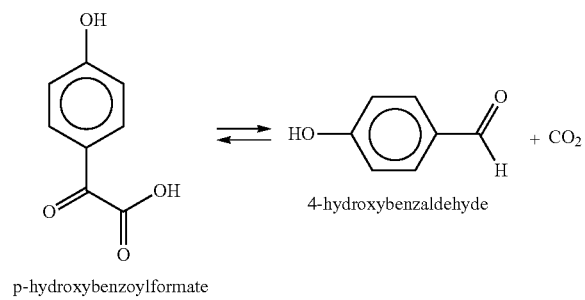

p-hydroxybenzoylformate 4-hydroxybenzaldehyde c) Conversion of $\Delta^1$-piperidine-2,6-dicarboxylate to 6-amino-2-oxohexanoic acid (enzymatic steps D2→D3)

In other embodiments, $\Delta^1$-piperidine-2,6-dicarboxylate undergoes spontaneous dehydration to produce L-α-amino-ε-ketopimelate as in the lysine biosynthesis pathway III.

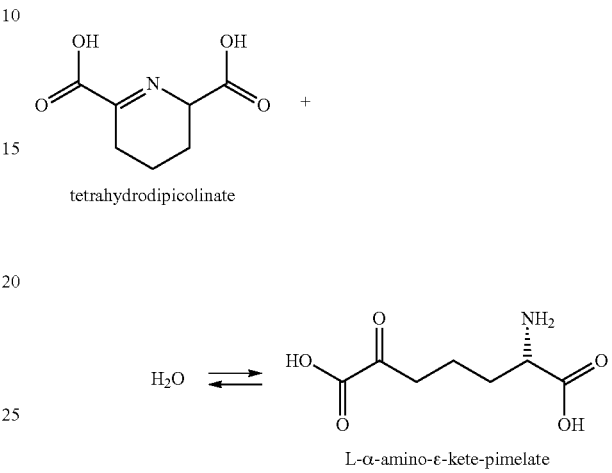

tetrahydrodipicolinate $H_2O$

L-α-amino-ε-kete-pimelate

In one embodiment, L-α-amino-ε-ketopimelate is converted to 6-amino-2-hexanoic acid by action of a decarboxylase, for example, diaminopimelate decarboxylase (EC 4.1.1.20), an enzyme shown to catalyze the last reaction step in the lysine biosynthesis pathway:

Although enzymes that catalyze the substrate to product conversion of (S)-2-amino-6-oxoheptanedioic acid to 6-amino-2-oxohexanoic have not been described, one skilled in the art will appreciate that the substrate (S)-2-amino-6-oxoheptanedioic acid is similar to the substrates listed in Table 9. Therefore, (S)-2-amino-6-oxoheptanedioic acid is likely to be an acceptable substrate for enzymes having a decarboxylase activity, such as the enzymes listed in Table 9.

TABLE 9

Desired substrate-product reaction
EC number
Name
Gene name (organism)
Protein accession number

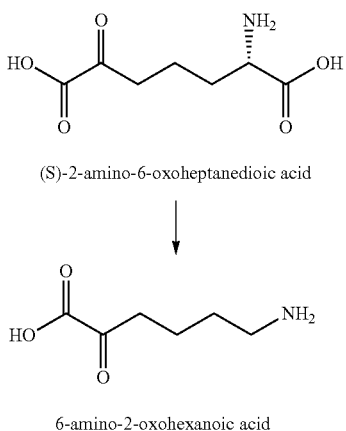 [SMILES: N[C@@H](CCCC(=O)C(=O)O)C(=O)O ; NCCCCC(=O)C(=O)O]

(S)-2-amino-6-oxoheptanedioic acid

↓

6-amino-2-oxohexanoic acid

TABLE 9-continued

EC 4.1.1.20
diaminopimelate
decarboxylase
lysA (*Escherichia coli
K12, Bacillus, subtilis*),
*Arabidopsis thaliana
col*
UniProt: O05321,
UniProt: O27390,
UniProt: O29458,
UniProt: O67262,
UniProt: P00861,
UniProt: P09890,
UniProt: P0A5M4,
UniProt: P19572,
UniProt: P23630,
UniProt: P41023,
UniProt: P44316,
UniProt: P56129,
UniProt: Q9CG26,
UniProt: Q9JWA6,
UniProt: Q9JWA6,
UniProt: Q9PII5,
UniProt: Q55484,
UniProt: Q58497.

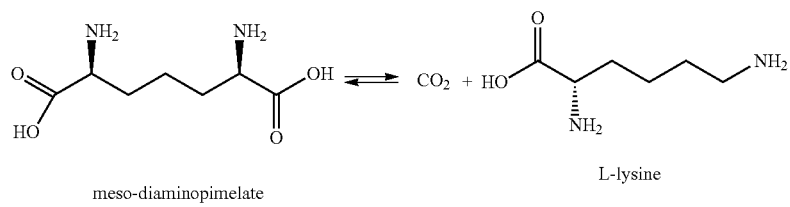 [SMILES: N[C@H](CCC[C@H](N)C(=O)O)C(=O)O ; "CO2" ; NCCCC[C@H](N)C(=O)O]

meso-diaminopimelate ⇌ $CO_2$ + L-lysine

EC 4.1.1.11
Aspartate 1-
decarboxylase
panD: *Escherichia
coli K12; Aquifex
aeolicus;
Helicobacter pylori;
Mycobacterium
tuberculosis;
Neisseria
meningitidis
serogroup A;
Neisseria
meningitidis
serogroup B;
Campylobacter
jejuni; Deinococcus
radiodurans;
Thermotoga
maritime;
Helicobacter pylori
J99; Synechocystis
sp.*
UniProt: O66773,
UniProt: P0A790,
UniProt: P52999,
UniProt: P56065,
UniProt: P65660,
UniProt: Q9JU49,
UniProt: Q9JZ56,
UniProt: Q9PIK3,
UniProt: Q9RWF1,
UniProt: Q9X037,
UniProt: Q9ZN30,
UniProt: Q55382

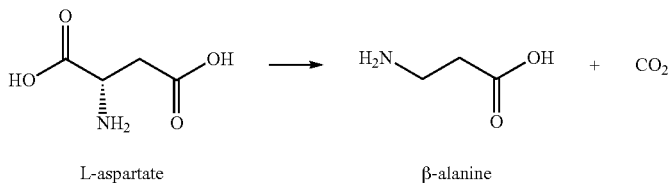 [SMILES: N[C@@H](CC(=O)O)C(=O)O ; NCCC(=O)O ; "CO2"]

L-aspartate → β-alanine + $CO_2$

EC 4.1.1.17
Ornithine
decarboxylase
ornithine
decarboxylase,
biosynthetic: speC
(*Escherichia coli
K12*); ornithine
decarboxylase,
degradative: speF
(*Escherichia coli
K12*); ODC1 (*Homo
sapiens*); speC
(*Pseudomonas
aeruginosa*)
UniProt: O15696,
UniProt: O66940,

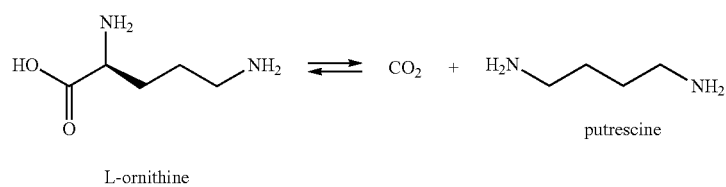

L-ornithine ⇌ $CO_2$ + putrescine

TABLE 9-continued

UniProt: O69865,
UniProt: P00860,
UniProt: P08432,
UniProt: P09057,
UniProt: P11926,
UniProt: P14019,
UniProt: P24169,
UniProt: P27116,
UniProt: P27118,
UniProt: P27119,
UniProt: P27120,
UniProt: P27121,
UniProt: P41931,
UniProt: P43099,
UniProt: P44317,
UniProt: P49725,
UniProt: P50134,
UniProt: P93351,
UniProt: P93357,
UniProt: Q9TZZ6,
UniProt: Q9UQW9,
UniProt: Q9X216,
UniProt: Q84527

EC 4.1.1.5
Glutamate
decarboxylase
gadA (*Escherichia coli K12*); gadB
(*Escherichia coli K12*); GAD1
(*Saccharomyces cerevisiae S2988C*);
GAD2 (*Homo sapiens*); GAD1
(*Homo sapiens*);
GAD2 (*Arabidopsis thaliana col*); GAD1
(*Arabidopsis thaliana col*)
UniProt: O81101,
UniProt: P14748,
UniProt: P18088,
UniProt: P20228,
UniProt: P48318,
UniProt: P48319,
UniProt: P48320,
UniProt: P48321,
UniProt: P69908,
UniProt: P69910,
UniProt: Q9CG20,
UniProt: Q05329,
UniProt: Q05683,
UniProt: Q07346,
UniProt: Q24062,
UniProt: Q49854,
UniProt: Q49855,
UniProt: Q49863,
UniProt: Q59956,
UniProt: Q99259

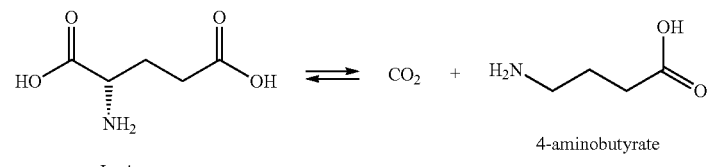

EC 4.1.1.19
Arginine
decarboxylase
arginine
decarboxylase,
biosynthetic: specA
(*Escherichia coli K12*); arginine
decarboxylase,
degradative: adiA
(*Escherichia coli K12*); speA
(*Pseudomonas aeruginosa; Bacillus subtilis*)
UniProt: O04429,
UniProt: O23141,
UniProt: O24128,
UniProt: O64453,

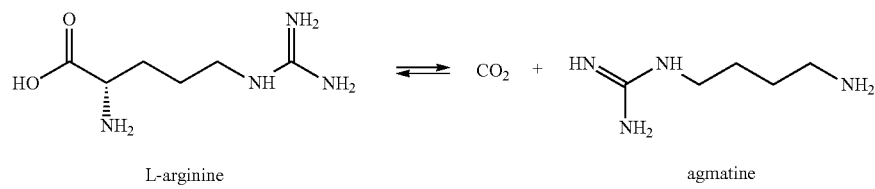 [SMILES: N=C(N)NCCC[C@H](N)C(=O)O ; "CO2" ; N=C(N)NCCCCN]

UniProt: O81161,
UniProt: O81177,
UniProt: P21170,
UniProt: P22220,
UniProt: P28629,
UniProt: P49726,
UniProt: P72587,
UniProt: P74576,
UniProt: Q96412,
UniProt: Q9JT25,
UniProt: Q9PPF5,
UniProt: Q9SI64,
UniProt: Q39827,
UniProt: Q43075

EC 4.1.1.14
Valine decarboxylase
panD

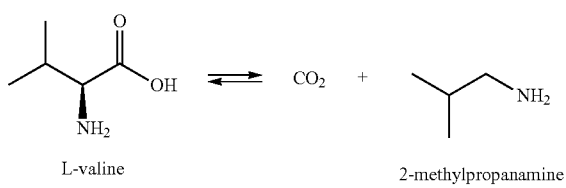

L-valine            2-methylpropanamine d) Conversion of L-2,3-dihydropicolinate to 5,6-dihydropyridine-2-carboxylate In an alternative pathway, 6-amino-2-oxohexanoic acid is produced by decarboxylation of L-2,3-dihydropicolinate to 5,6-dihydropyridine-2-carboxylate (enzymatic step E1), followed by a spontaneous hydration of 5,6-dihydropyridine-2-carboxylate to (E)-6-amino-2-oxohex-3-enoic acid (Step E2), and a subsequent dehydrogenation of (E)-6-amino-2-oxohex-3-enoic acid to 6-amino-2-oxohexanoic acid (enzymatic step E3) as depicted in FIG. 3A.

In some embodiments, L-2,3-dihydropicolinate is first converted to 5,6-dihydropyridine-2-carboxylate as depicted below:

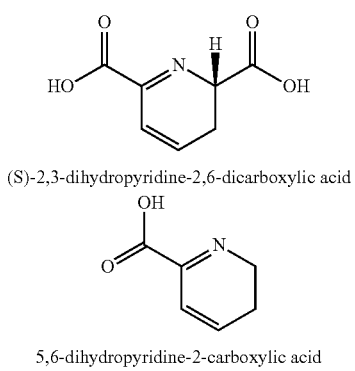

(S)-2,3-dihydropyridine-2,6-dicarboxylic acid 5,6-dihydropyridine-2-carboxylic acid There are no enzymes known in the art that catalyze the substrate L-2,3-dihydropicolinate to produce 5,6-dihydropyridine-2-carboxylate. However, there are a few decarboxylases that are able to decarboxylate ring mounted carboxylic acids. One skilled in the art would appreciate that it is likely that these enzymes may have, or could be engineered to have, activity towards L-2,3-dihydropicolinate. Examples of such decarboxylases include, but are not limited to, benzoylformate decarboxylase (EC 4.1.1.7), 3-hydroxy-2-methyl pyridine-4,5-dicarboxylate decarboxylase (EC 4.1.1.51), pyrrole-2-carboxylase (EC 4.1.1.-), gallate decarboxylase (4.1.1.59), Dopa decarboxylase (EC 4.1.1.28), Phenylpyruvate decarboxylase (EC 4.1.1.43), 4,5-dihydroxyphthalate decarboxylase (EC 4.1.1.55), 5-dihydroxybenzoate decarboxylase (EC 4.1.1.62), Uracil-5-carboxylate decarboxylase (EC 4.1.1.66), and Cis-1,2-dihydroxycyclohexa-3,5-diene-1-carboxylate dehydrogenase (EC 1.3.1.25). In a subsequent step, the 5,6-dihydropyridine-2-carboxylic acid ring is opened in the presence of water to produce (E)-6-amino-2-oxohex-3-enoic acid. This reaction is similar to the hydration of 2,3,4,5-terahydropyridine-2-carboxylic acid (in the lysine degradation pathway) and is likely to be spontaneous in the presence of water.

e) Conversion of (E)-6-amino-2-oxohex-3-enoic acid is converted to 6-amino-2-oxohexanoic acid In a subsequent step (E3), the (E)-6-amino-2-oxohex-3-enoic acid is converted to 6-amino-2-oxohexanoic acid. Although there are no enzymes known in the art that catalyze the substrate to product conversion, the enzymes listed in Table 4 may also have an activity towards (E)-6-amino-2-oxohex-3-enoic acid or could be engineered to catalyze the reaction. Theses enzymes include, but are not limited to, 2-enoate reductase (EC 1.3.1.31), NADH-dependent fumarate reductase (EC 1.3.1.6), coumarate reductase (EC 1.3.1.11), β-nitroacrylate reductase (EC 1.3.1.16), Maleylacetate reductase (EC 1.3.1.32), N-ethylmaleimide reductase (EC 1.-.-.-) and EC 1.3.99.-. One should appreciate that (E)-6-amino-2-oxohex-3-enoic acid could first be converted to (E)-6-amino-2-oxohex-3-enoyl-CoA, then to (E)-6-amino-2-oxohexanoyl-CoA, and then to (E)-6-amino-2-hydroxyl-hexanoyl-CoA. The final steps may be identical to the ones detailed in Pathways VIII and IX.

f) Conversion of lysine to 6-amino-2-oxohexanoic acid

One should appreciate that lysine may be directly converted to 6-amino-2-oxohexanoic acid by action of L-lysine oxidase as described in the lysine degradation pathway VII (EC 1.4.1.3.14) (FIG. 4). The L-lysine oxidase has been described in strains of the ascomycetes *Trichoderma viride* and *Trichoderma harzianum*.

D. Engineered pathway for the bioproduction of adipic acid, 6-hydroxyhexanoate and 1,6-hexanediol from nitrogen-containing heterocyclic rings Aspects of the invention relate to engineered metabolic pathways for the bioproduction of adipic acid, 1,6-hexanediol and 6-hydroxyhexanoate from nitrogen-containing heterocyclic rings. One aspect of the invention provides engineered metabolic pathways for the bioproduction of adipic acid, 6-hydroxyhexanoate (6HH) and 1,6-hexanediol from nitrogen-containing heterocyclic rings. In some aspects of the invention, engineered metabolic pathways for the production of 2-oxoadipate semialdehyde as a metabolite intermediate for the production of adipic acid, 6-hydroxyhexanoate and/or 1,6-hexanediol are provided. Accordingly, aspects of the invention provide recombinant microorganisms having an engineered pathway for the production of adipic acid. Other aspects of the invention provide a recombinant microorganism having an engineered pathway for the production of 6-hydroxyhexanoate. Yet other aspects of the invention provide a recombinant microorganism having an engineered pathway for the production of 1,6-hexanediol.

In a preferred embodiment, the C6 difunctional alkanes are produced from L-pipecolate. L-pipecolate is an intermediate of the L-lysine and D-lysine degradation pathway. L-pipecolate may also be bioproduced according to Pathway D' as describe herein. According to some aspects of the invention, L-pipecolate is converted to $\Delta^1$-piperideine-6-L-carboxylate, and then $\Delta^1$-piperideine-6-L-carboxylate is converted to L-2-aminoadipate-6-semialdehyde; L-2-aminoadipate-6-semialdehyde is optionally converted to L-2-aminoadipate. One skilled in the art would appreciate that this set of reactions is part of the lysine degradation pathway. In some embodiments, L-pipecolate is converted to $\Delta^1$-piperideine-6-L-carboxylate by action of L-pipecolate dehydrogenase or L-pipecolate oxidase. L-pipecolate dehydrogenases and L-pipecolate oxidase are known in the art and are part of the lysine degradation pathway. Examples of L-pipecolate oxidases include, but are not limited to, EC 1.5.99.3 (*Pseudomonas putida*) and EC 1.5.3.7. (*Schizosaccharomyces pombe, Arabidopsis thaliana, Homo sapiens*). In a preferred embodiment, the enzyme is L-pipecolate dehydrogenase with EC number 1.5.99.3.

The reactions catalyzed by L-pipecolate oxidase or dehydrogenase are shown below:

EC 1.5.99.3:

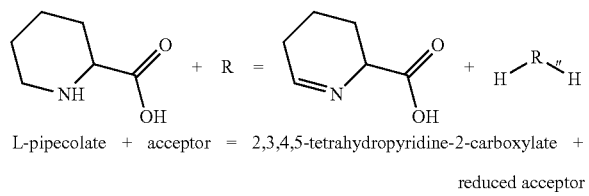

L-pipecolate + acceptor = 2,3,4,5-tetrahydropyridine-2-carboxylate + reduced acceptor

EC 1.5.3.7:

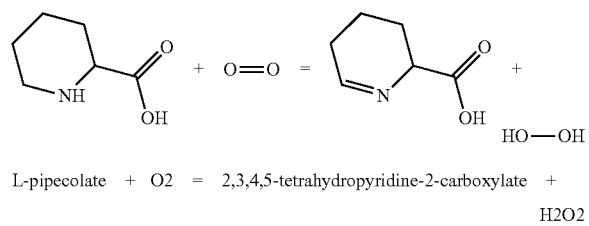

L-pipecolate + O2 = 2,3,4,5-tetrahydropyridine-2-carboxylate + H2O2

$\Delta^1$-piperideine-6-L-carboxylate reacts with water to form spontaneously L-2-aminoadipate-6-semialdehyde. $\Delta^1$-piperideine-6-L-carboxylate and L-2-aminoadipate-6-semialdehyde can then be converted to 2-aminoadipate by an L-aminoadipate-semialdehyde dehydrogenase or an oxidoreductase (EC 1.2.1.31), the oxidizing equivalent being supplied in the form of an oxidized nicotinamide cofactor NAD or NADH as detailed below:

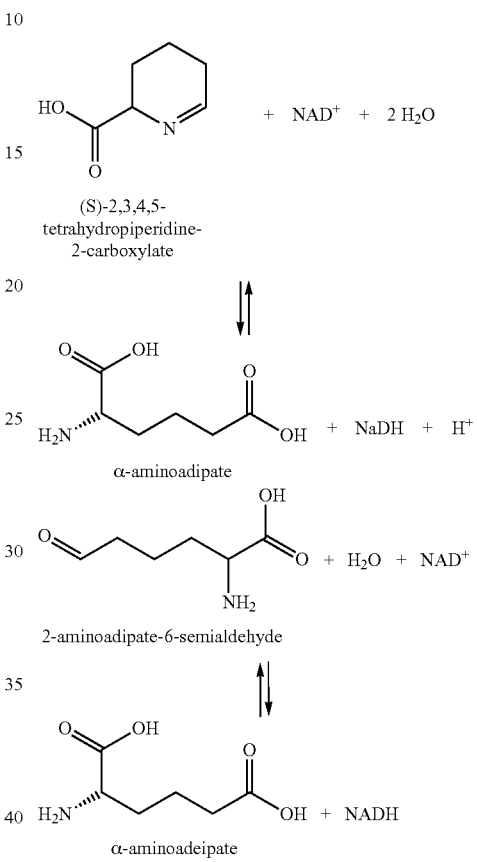

L-aminoadipate-semialdehyde dehydrogenase or oxidoreductase have been described in a variety of species including *Pseudomonas putida* (encoded by amaA), *Streptomyces clavuligerus* (encoded by pcd), *Flavobacterium lutescens* (encoded by pcd), *Homo sapiens, Mus musculus, Rattus norvegicus, Schizosaccharomyces pombe, Acremonium chrysogenum, Penicillium chrysogenum* and *Candida albicans*.

One should appreciate that 2-aminoadipate can be converted to adipic acid by removal of the α-amino group as described for the deamination of lysine in Pathways I through IX. Alternatively, 2-aminoadipate may be converted to α-ketoadipate by a α-aminoadipate aminotransferase (EC 2.6.1.39, gene aadat, lysN) or a diaminopimelate dehydrogenase (EC 1.4.116, gene ddb or Dapdh) and subsequently to adipic acid as described in pathway VII through IX.

Yet in another embodiment, L-2-aminoadipate-6-semialdehyde is converted to adipate semialdehyde by removal of the α-amino group as described in Pathways I through IX. Adipate semialdehyde can then finally be converted to 1,6-hexanediol or 6-hydroxyhexanoate by an aldehyde dehydrogenase and/or an alcohol dehydrogenase.

Aldehyde dehydrogenases catalyze the conversion of the aldehyde functional group into an alcohol functional group.

Alcohol dehydrogenases (ADHs) (EC 1.1.1.1 and EC 1.1.1.2) catalyze the reversible reduction of ketones and aldehydes to alcohols with the reduction of NAD+ to NADH. In some embodiments, the alcohol dehydrogenase includes, but is not limited, to adhA or adhB (from *Z. mobilis*), butanol dehydrogenase (from *Clostridium acetobutylicum*), propanediol oxidoreductase (from *E. coli*), and ADHIV alcohol dehydrogenase (from *Saccharomyces*), ADH6 (from *S. cerevisiae*). In some embodiments, the hydro-carboxylic acid is subjected to dehydrogenation using an alcohol dehydrogenase or an aldehyde dehydrogenase to produce 1,6-hexane diol. Aldehyde NAD(+) dehydrogenase activity and alcohol NAD(+) dehydrogenase activities can be carried out by two different polypeptides, or carried out by a single polypeptide, such as a multi-functional aldehyde-alcohol dehydrogenase (EC 1.2.1.10) from *E. coli* (Goodlove et al. Gene 85:209-14, 1989; GenBank Accession No. M33504). Polypeptides having aldehyde dehydrogenase (NAD(P)+) (EC 1.2.1.-) or aldehyde dehydrogenase (NAD(+)) (EC 1.2.1.3) activity can be used in combination with an alcohol dehydrogenase to reduce the remaining carboxylic acid to an alcohol, yielding a diol. Nucleic acids encoding such polypeptides can be obtained from various species including, without limitation, *S. cerevisiae*.

E. Engineered pathways for the production C6 difunctional from L-lysine

1. Bioproduction of adipic acid, 6-hydroxyhexanoate and 1,6-hexanediol

Some aspects of the invention provide biosynthetic pathways for the production of adipic acid, 6-hydroxyhexanoate, 1,6-hexanediol from lysine and from 2-oxoadipate semialdehyde. All these pathways share the first enzymatic step in which lysine is first converted to 2-amino-adipate-6-semialdehyde (see FIG. 5).

In one embodiment, in enzymatic step 5a or 5m, lysine is first converted to α-aminoadipate semialdehyde (also known as 2-aminoadipate-6-semialdehyde), the resulting α-aminoadipate semialdehyde is then converted to 2-oxoadipate semialdehyde (enzymatic step 5b). In the initial step 5a, lysine is converted to α-aminoadipate semialdehyde by action of an enzyme having a lysine amino-transferase activity. There are at least two known types of biochemical reactions that can catalyze the substrate to product conversion of lysine to α-aminoadipate semialdehyde. The first enzyme is a lysine amino-transferase (enzymatic step 5a, EC 2.6.1.36).

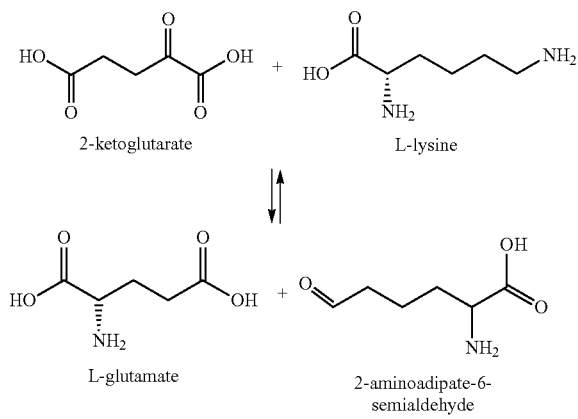

Enzymes catalyzing this substrate to product conversion are well known and participate in the lysine degradation pathway VI and employ pyridoxal phosphate as a cofactor. L-lysine 6-aminotransferase has been demonstrated in yeasts and bacteria. Examples of suitable L-aminotransferase enzymes are available from a variety of sources, for example, *Nocardia lactamdurans* (UniProt accession number Q05174), *Flavobacterium lutescens* (gene lat, Fujii et al., 2000, J. Biochem., 128(3); 391-7), *Candida utilis*, *Streptomyces clavuligerus* (UniProt: Q01767, gene lat), *Rhodococcus* sp., *Mycobacterium marinum*, *Mycobacterium ulcerans*, *Saccharopolyspora erythraea*, *Frankia alni* and *Frankia* sp.

The second known enzyme capable of catalyzing the substrate to product conversion of lysine to α-aminoadipate semialdehyde is L-lysine-ε-dehydrogenase (enzymatic step 5m). L-lysine ε-dehydrogenase catalyzes the oxidative deamination of the lysine epsilon amino group in an NAD+-dependent reaction (EC 1.4.18; Lysine degradation pathway VIII):

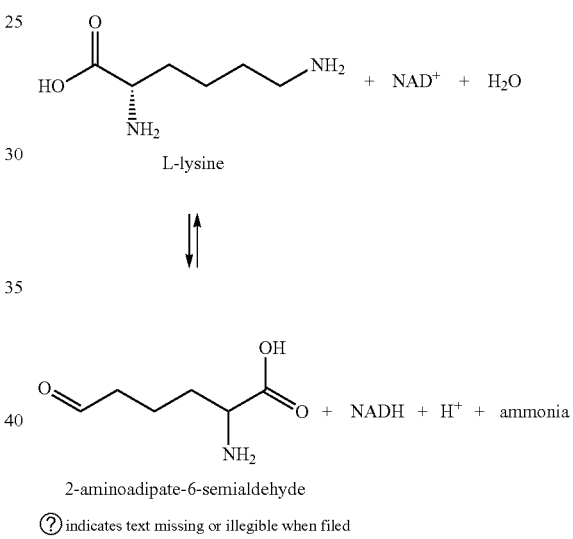

Examples of suitable L-lysine ε-dehydrogenase enzymes are available from a variety of sources, for example, *Agrobacterium tumefaciens* and *Geobacillus stearothermophilus* (gene: lysDH)

Figure 5:
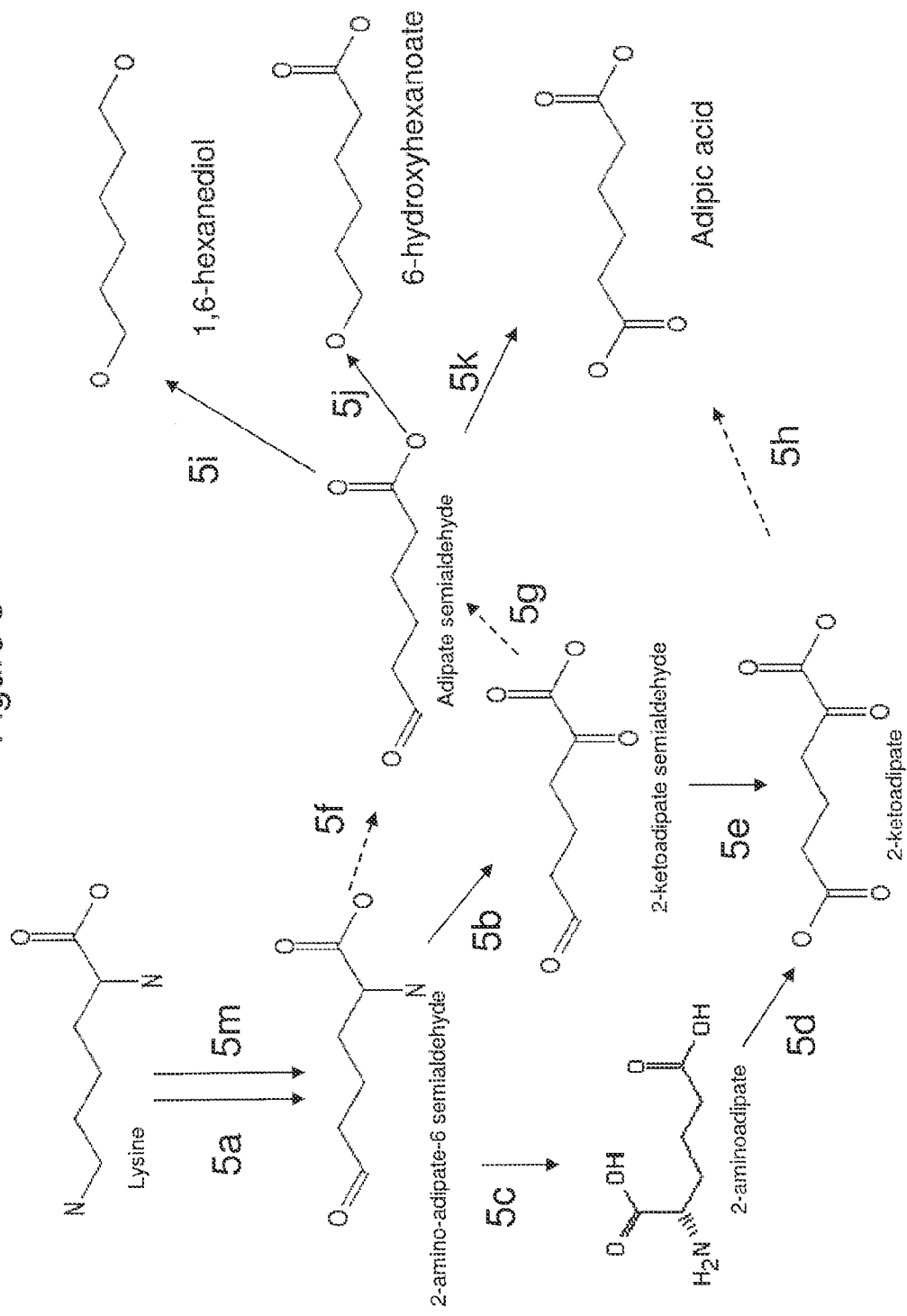
FIG. 5 represents a flow diagram for the bioproduction of adipic acid, 6-hydroxyhexanoate, and 1,6-hexanediol from lysine.
Figure 6:
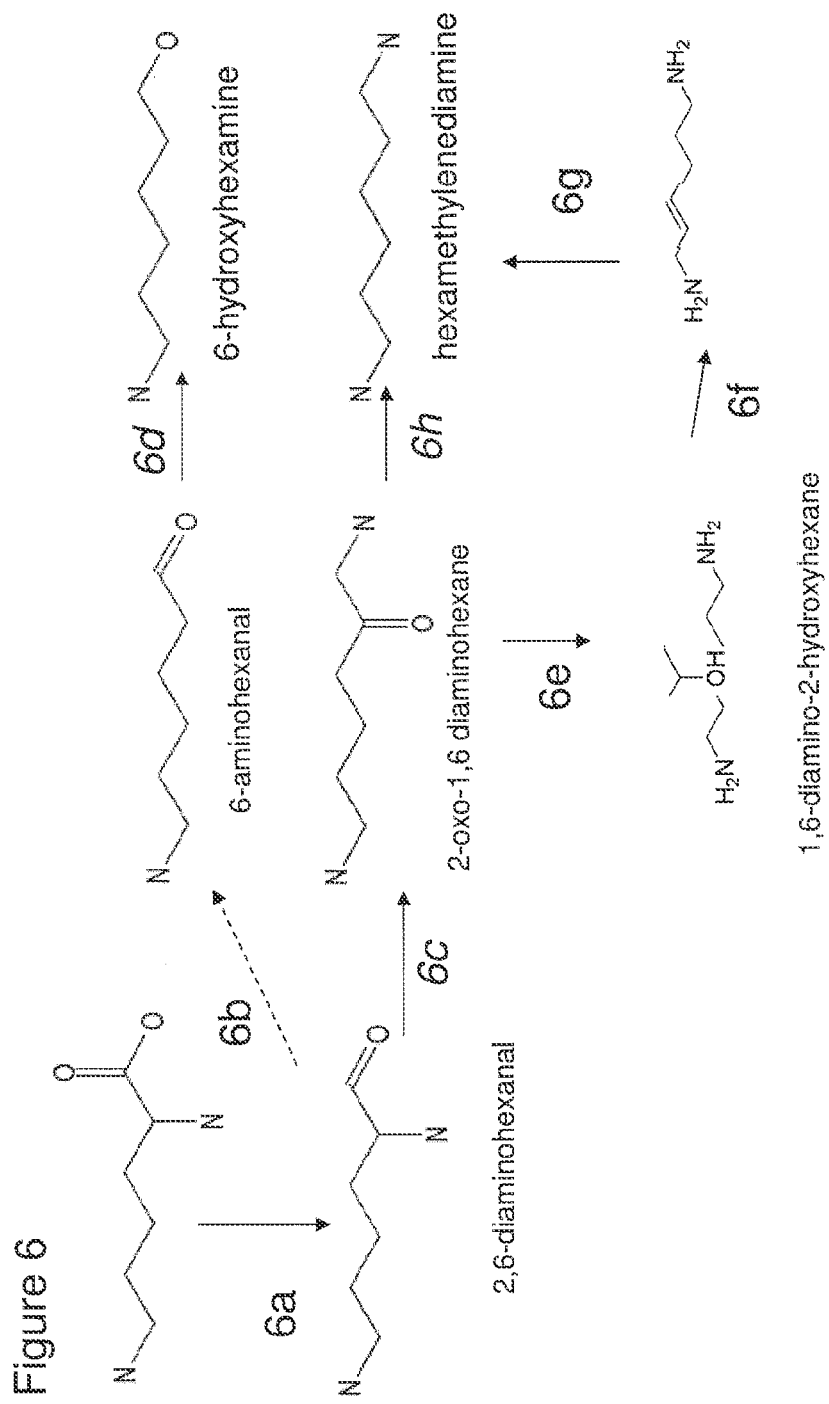
FIG. 6 represents a flow diagram for the bioproduction of 6-hydroxyhexamine and hexamethylenediamine from lysine.

As illustrated in FIG. 5, 2-aminoadipate-6-semialdehyde can then be converted to adipate semialdehyde (enzymatic step 5b followed by enzymatic step 5g or enzymatic step 5f) for the production of adipic acid, 6HH, or 1,6-hexanediol.

In a first embodiment, adipate semialdehyde is produced via an engineered pathway comprising enzymatic steps 5b and 5g. In the enzymatic step 5b (FIG. 5), 2-aminoadipate-6-semialdehyde is converted to 2-oxoadipate semialdehyde by action of an enzyme having a 2-aminoadipate activity. There are two known types of biochemical reactions that could affect the substrate to product conversion, namely the 2-aminoadipate aminotransferase (EC 2.6.1.39) and the Kynurenine aminotransferase II (EC 2.6.1.7) as depicted below.

EC 2.6.1.39

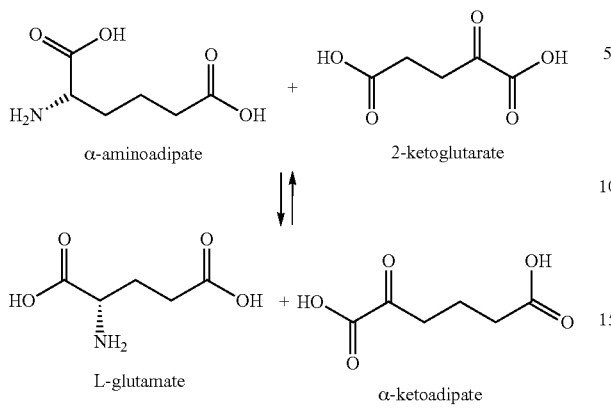

α-aminoadipate        2-ketoglutarate

L-glutamate        α-ketoadipate

Enzymes of the EC 2.6.1.39 class catalyze this substrate to product conversion and participate in the lysine degradation II, lysine degradation V, lysine biosynthesis IV and lysine biosynthesis V pathways. Examples of suitable α-aminoadipate aminotransferase enzymes are available from a variety of sources, for example, *Thermus thermophilus* (gene LysN, UniProt: Q5SL82, Q7X567, Q72LL6, Miyazaki et al., 2004, Microbiology 150; 2327-34), *Thermus aquaticus* (UniProt B4CM67), *Rattus Norvegicus* (Aadat, Kat2), and *Homo sapiens* (UniProt Q8N5Z0).

Kynurenine aminotransferase or Aspartate aminotransferase (Enzyme EC 2.6.1.7, AspC, *Escherichia coli* K12) is a multifunctional enzyme that catalyzes the synthesis of aspartate, phenylalanine and other compounds via a transamination reaction.

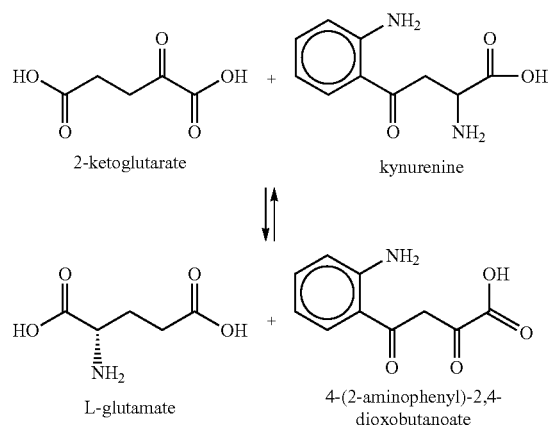

2-ketoglutarate        kynurenine

L-glutamate        4-(2-aminophenyl)-2,4-dioxobutanoate

In subsequent step 5g, 2-ketopadipate semialdehyde is converted to adipate semialdehyde by first action of a dehydrogenase (enzymatic step 5g1) to convert the ketone group to a secondary alcohol group (2-hydroxyadipate semialdehyde), followed by action of a dehydratase that catalyzes the conversion of the secondary alcohol group to an alkene (enzymatic step 5g2), and finally followed by the action of a dehydrogenase (enzymatic step 5g3) that catalyzes the conversion of the alkene to an alkane. In some embodiments, ketoadipate semialdehyde is first converted to the thiol ester by CoA transferase and then subjected to enzymatic steps 5g1 to 5g3. Enzymes capable of catalyzing enzymatic steps 5g include, but are not limited to, enzymes listed in enzymatic steps C2, C4, C5, C3, B4, B5, B6 and A5.

Yet in other embodiments, 2-ketopadipate semialdehyde is first converted to the corresponding acp-compound. In some embodiments, the dehydrogenase is a 3-oxoacyl-[acyl-carrier protein] reductase (EC 1.1.1.100) shown to catalyze the following reaction in the fatty acid biosynthesis superpathway:

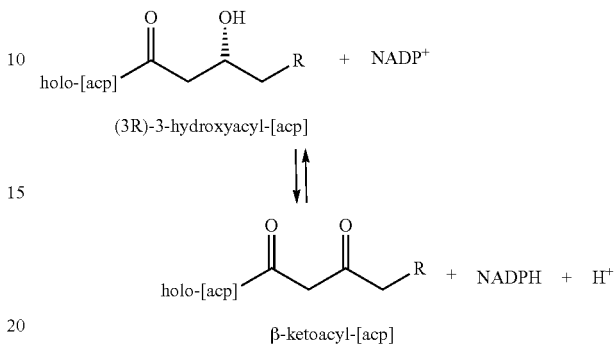

(3R)-3-hydroxyacyl-[acp]

β-ketoacyl-[acp]

In some embodiments, the dehydrogenase is a 3-ketoacyl-[acyl-carrier-protein] reductase (FabG gene from *E. Coli*), the fatty acid synthase (Fast gene from *Saccharomyces cerevisiae*) or the fatty acid synthase (FASN gene from *Homo sapiens*). In some embodiments, the dehydratase is a 3-hydroxyoctanoyl-[acyl-carrier-protein] dehydratase (EC 4.2.1.59) which catalyses the following reaction:

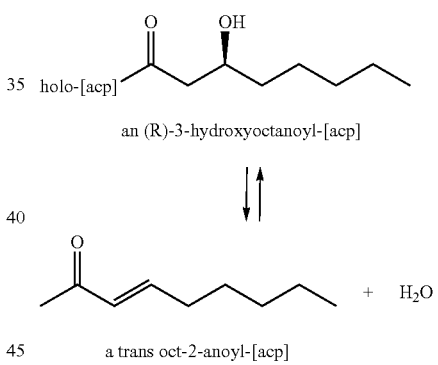

an (R)-3-hydroxyoctanoyl-[acp]

a trans oct-2-anoyl-[acp]

Examples of 3-hydroxyoctanoyl-[acyl-carrier-protein] dehydratases include, but are not limited to, 3-hydroxyacyl-ACP dehydrase from *Spinacia oleracea*, β-hydroxyacyl-ACP dehydrase (FabA gene from *E. Coli*), and β-hydroxyacyl-ACP dehydratase (FabZ gene from *E. Coli*).

In some embodiments, the second dehydrogenase is an enoyl acyl carrier protein reductase (EC 1.3.1.9) such as enoyl-ACP reductase (fabI gene form *E. Coli*) shown to catalyze the following reaction:

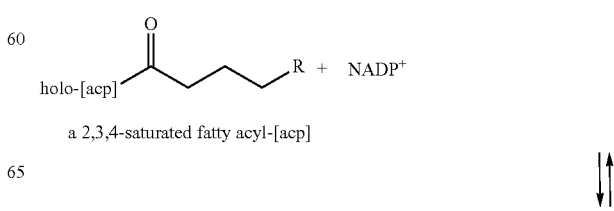

a 2,3,4-saturated fatty acyl-[acp]

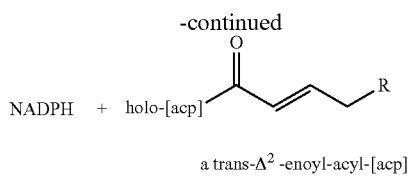

a trans-$\Delta^2$-enoyl-acyl-[acp]

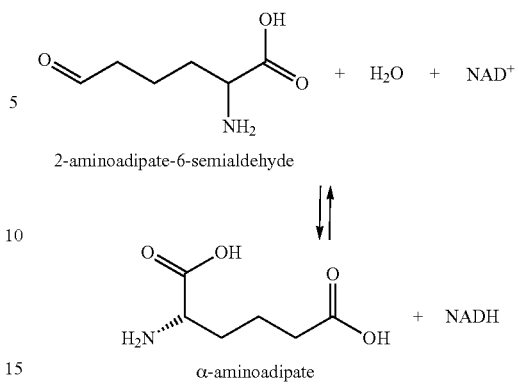

In some embodiments, the first and the second dehydrogenase are identical fatty acid synthases (Fas2 gene from *Saccharomyces cerevisiae* or FASN gene from *Homo sapiens*).

In some embodiments, adipate semialdehyde can be used to produce 1,6-hexanediol, 6HH, adipic acid, aminocaproic acid, hexamethylenediamine or 6-aminohexanol. In an exemplary embodiment, adipate semialdehyde is converted to 6HH by simple hydrogenation and the reaction is catalyzed by an alcohol dehydrogenase (EC 1.1.1.1). This enzyme belongs to the family of oxidoreductases, specifically those acting on the CH—OH group of donors with $NAD^+$ or $NADP^+$ as acceptors. In some embodiments, a 6-hydroxyhexanoate dehydrogenase (EC 1.1.1.258) that catalyzes the following chemical reaction is used:

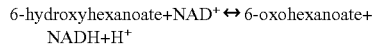

Other alcohol dehydrogenases include but are not limited to adhA or adhB (from *Z. mobilis*), butanol dehydrogenase (from *Clostridium acetobutylicum*), propanediol oxidoreductase (from *E. coli*), and ADHIV alcohol dehydrogenase (from *Saccharomyces*).

Yet in some embodiments, adipate semialdehyde is converted to 6-hydroxyhexanoate by an alcohol dehydrogenase and then to 1,6-hexanediol by action of an alcohol dehydrogenase or an aldehyde dehydrogenase (enzymatic step 5i). Alcohol dehydrogenases (ADHs) (EC 1.1.1.1 and EC 1.1.1.2) catalyze the reversible reduction of ketones and aldehydes to alcohols with the reduction of $NAD^+$ to NADH. In some embodiments, examples of alcohol dehydrogenases include but are not limited to adhA or adhB (from *Z. mobilis*), butanol dehydrogenase (from *Clostridium acetobutylicum*), propanediol oxidoreductase (from *E. coli*), ADHIV alcohol dehydrogenase (from *Saccharomyces*), and ADH6 (from *S. cerevisiae*). Aldehyde NAD(+) dehydrogenase activity and alcohol NAD(+) dehydrogenase activities can be carried out by two different polypeptides, or carried out by a single polypeptide, such as a multi-functional aldehyde-alcohol dehydrogenase (EC 1.2.1.10) from *E. coli* (Goodlove et al. Gene 85:209-14, 1989; GenBank Accession No. M33504). Polypeptides having aldehyde dehydrogenase (NAD(P)+) (EC 1.2.1.-) or aldehyde dehydrogenase (NAD(+)) (EC 1.2.1.3) activity, as well as nucleic acids encoding such polypeptides, can be obtained from various species including, without limitation, *S. cerevisiae*.

In a further alternative thereto, 2-aminoadipate-6-semialdehyde is first converted to 2-aminoadipate (enzymatic step 5c), the resulting 2-aminoadipate is converted to 2-ketoadipate (enzymatic step 5d), and finally to adipic acid (enzymatic step 5h). 2-aminoadipate-6-semialdehyde is converted to 2-aminoadipate by action of a L-aminoadipate-semialdehyde dehydrogenase (EC 1.2.1.31).

Examples of suitable L-aminoadipate-semialdehyde dehydrogenase enzymes are available form a number of sources, for example, *Streptomyces clavuligerus* (pcd), *Flavobacterium lutescens* (pcd), *Acremonium chrysogenum*, *Candida albicans*, *Candida maltosa*, *Homo sapiens*, *Kluyveromyces lactis*, *Mus musculus*, *Penicillium chrysogenum*, *Pichia guilliermondii*, *Pseudomonas putida*, *Pseudomonas* sp., *Rattus norvegicus*, *Saccharomyces cerevisiae* and *Schizosaccharomyces pombe*.

In enzymatic step 5d, the resulting 2-aminoadipate is converted to 2-ketoadipate by action of a 2-aminoadipate aminotransferase (EC 2.6.1.39) which participates in the amino-acid degradation pathway; L-lysine degradation via saccharopine pathway and in the glutaryl-CoA from L-lysine pathway. 2-ketoadipate is then converted to adipic acid (enzymatic steps 5h) by successive enzymatic steps described for the conversion of 2-ketoadipate semialdehyde to adipate semialdehyde.

In some embodiments, 2-amino adipate is converted to adipic acid by successive enzymatic steps as described above for the conversion of 1-aminoadipate-6-semialdehyde to adipate semialdehyde (enzymatic step 5f, see Pathways I through IX).

2. Engineered Pathways for the Production of 6-Hydroxyhexanamine and Hexamethylenediamine from Lysine Aspects of the invention relates to the production of 6-hydroxyhexanamine and/or hexamethylenediamine. Accordingly, aspects of the invention provide a recombinant microorganism having an engineered pathway for the production of 6-hydroxyhexanamine and hexamethylenediamine. In a preferred embodiment, lysine is converted to 2,6-diaminohexanal by action of an amino aldehyde dehydrogenase (enzymatic step 6a). 2,6-diaminohexanal can then be converted to 6-aminohexanal by deamination (enzymatic step 6b) and subsequently to 6-aminohexanol by an alcohol dehydrogenase (enzymatic step 6d). In some embodiments, 2,6-diaminohexanal is converted to 2-oxo-1,6-diaminohexane (enzymatic step 6c) by a semialdehyde aminomutase. Although enzymes that catalyze the 2,6-diaminohexanal to 2-oxo-1,6-diaminohexane conversion have not been described, one should appreciate that Glutamate-1-semialdehyde 2,1-aminomutase may catalyze this reaction. Glutamate-1-semialdehyde 2,1-aminomutase has been isolated in a variety of species including, but not limited to, *Escherichia coli*, *Synechococcus* sp, *Xanthomonas campestris*, and *Propionibacterium freudenreichii*. Glutamate-1-semialdehyde 2,1-aminomutase genes include, but are not limited to, hemL (*Escherichia coli* K12, *Salmonella typhimurium*) and GSA I (*Arabidopsis thaliana* col). In a subsequent step, 2-oxo-1,6-diaminohexane is then converted to 1,6-diaminohexane by removal of the ketone group (enzymatic step 6h). In another embodiment, 2-oxo-1,6-diaminohexane is first reduced to 2-hydroxy-1,6-diaminohexane (enzymatic step 6e) by an alcohol dehydrogenase, and then further reduced to 1,6-diamino-hexene (enzymatic step 6f) which can then be converted to hexamethylenediamine (enzymatic step 6e).

II. Engineered Pathways for the Production of C5 Difunctional Alkanes

Aspects of the invention relate to the bioproduction of C5 difunctional alkanes. C5 difunctional alkanes of interest include 5-hydroxypentanoate, glutarate, 1,5-pentanediol, 5-aminopentanoate, 5-aminopentanol and cadaverine. Accordingly, aspects of the invention provide a recombinant microorganism having an engineered pathway for the production 5-hydroxypentanoate, glutarate, 1,5-pentanediol, 5-aminopentanoate, 5-aminopentanol and cadaverine.

A. Engineered Pathways for the Production of C5 Difunctional Alkanes from Lysine.

Aspects of the invention relate to the bioproduction of C5 difunctional alkanes from a C6 difunctional alkane. In a preferred embodiment, C5 difunctional alkanes are produced from lysine as shown in FIG. 7.

Methods for producing cadaverine by introducing a lysine decarboxylation gene and/or a lysine-cadaverine antiporter gene into a lysine producing microorganism have been described (see for example JP 2002223770 and WO2008/092720). Lysine decarboxylase catalyzes the decarboxylation of L-lysine into cadaverine. The enzyme has been classified as EC 4.1.1.18. The enzymes isolated from *Escherichia coli* having lysine decarboxylase activity are the cadA gene product and the ldc gene product.

Figure 7:
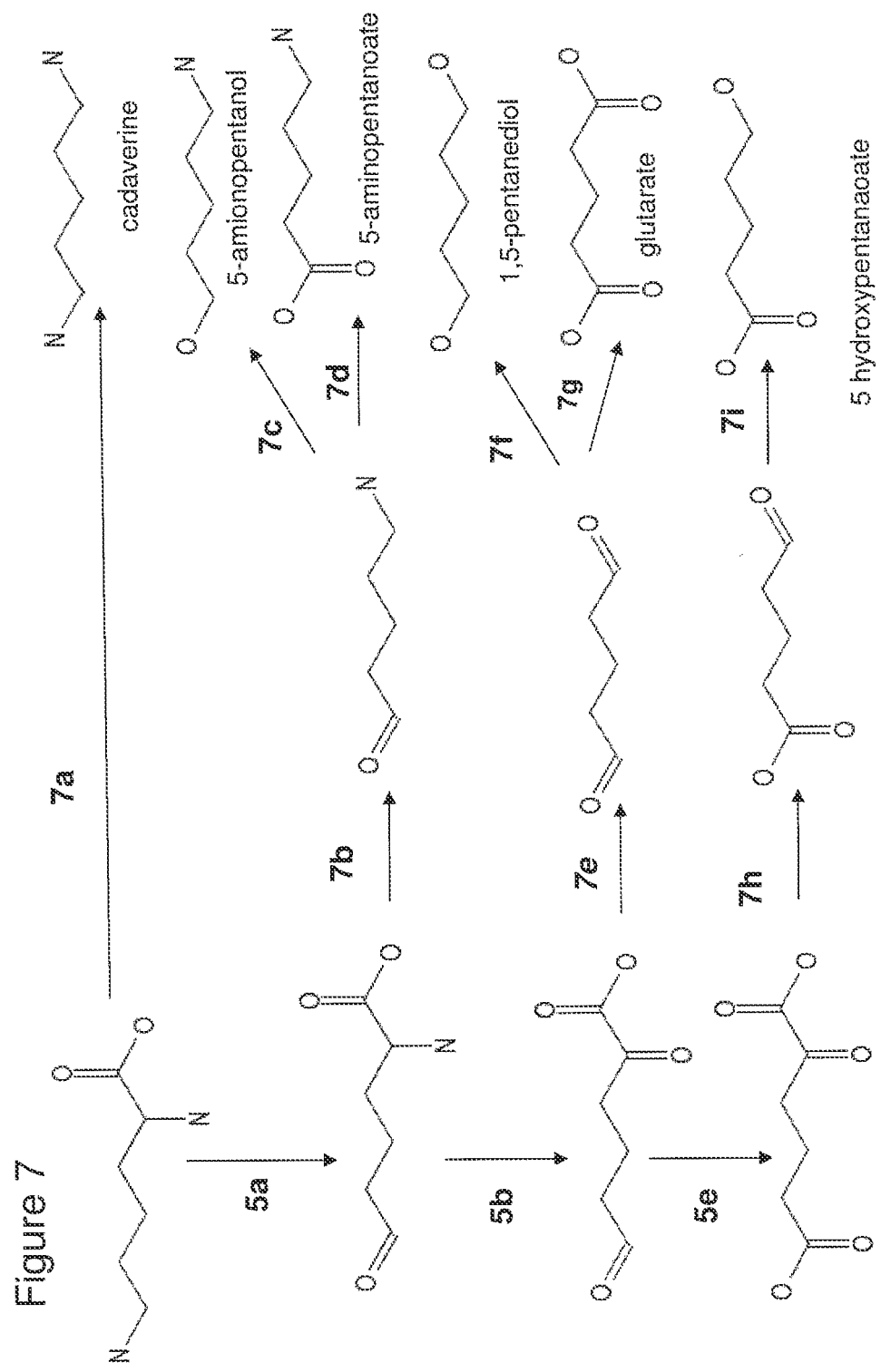
FIG. 7 represents a flow diagram for the bioproduction of C5 difunctional alkanes from lysine.

As illustrated in FIG. 7, the C5 difunctional alkanes engineered pathway begins with the conversion of lysine to 2-amino-5-oxo-hexanoate (or α-aminoadipate semialdehyde) by a L-lysine-6-aminotransferase (classified as EC 2.6.1.36 and EC 1.4.1.18) as described in the bioproduction of C6 difunctional alkanes (enzymatic step 5a). In some embodiments, α-aminoadipate semialdehyde is converted to 5-aminopentanal by a decarboxylase (enzymatic step 7b). Examples of decarboxylase include, but are not limited to, lysine decarboxylase, L-Ornithine carboxylyase (EC 4.1.1.17, odc gene product and spec speF gene product), Aspartate 4-decarboxylase (EC 4.1.1.12), and glutamate decarboxylase (gadA (*Escherichia coli* K12), gadB (*Escherichia coli* K12), GAD1 (*Saccharomyces cerevisiae* S288C), GAD2 and GAD 1 (*Homo sapiens, Arabidopsis thaliana* col). 5-aminopentanal can be converted to 5-aminopentanol by an alcohol dehydrogenase or to 5-aminopentanoate by an aldehyde dehydrogenase.

In some embodiments, α-aminoadipate semialdehyde is converted to α-ketoadipate semialdehyde by a α-aminoadipate aminotransferase (enzymatic step 5b, EC 2.6.1.39, lysine degradation pathway). The glutarate and the 1,5-pentanediol pathways involve a ketodecarboxylase to convert α-ketoadipate semialdehyde to 5-oxopentanal (enzymatic step 7e) and an alcohol dehydrogenase to convert 5-oxopentanal to 1,5-pentanediol (enzymatic step 7θ or an aldehyde dehydrogenase to convert 2-oxopentanal to glutarate (enzymatic step 7g).

Although there are no known enzymes shown to catalyze the decarboxylation of α-ketoadipate semialdehyde to 5-oxopentanal, a list of ketodecarboxylases was generated based on the following criteria: (i) demonstrated activity on a 2-ketocarboxylate, and (ii) availability of protein sequence information.

TABLE 10

4.1.1.71
2-ketoglutarate
decarboxylase
kgd from *M. tuberculosis*
UniProt: O50463

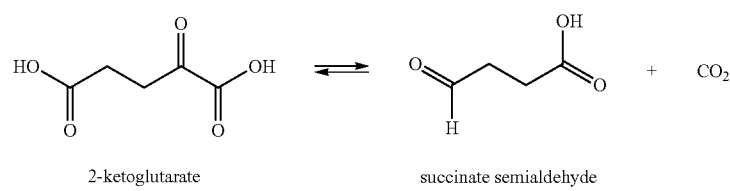 [SMILES: O=C(O)CCC(=O)C(=O)O ; O=CCCC(=O)O ; "CO2"]

2-ketoglutarate      succinate semialdehyde 4.1.1.1
2-ketoisovalerate
decarboxylase
kivD from *L. lactis*
UniProt: Q684J7

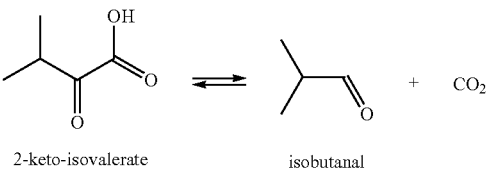

2-keto-isovalerate      isobutanal 4.1.1.43
Transaminated a.a.
decarboxylase
ARO10 from *S. cerevisiae*
UniProt: Q06408

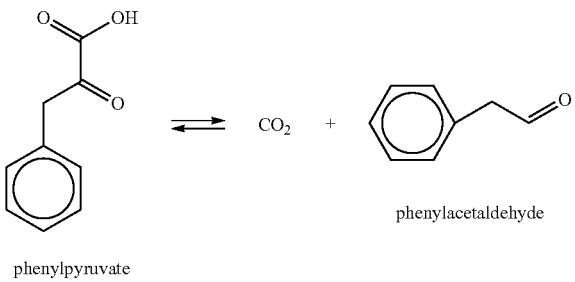

phenylpyruvate      phenylacetaldehyde

TABLE 10-continued 4.1.1.7
Benzoylformate
decarboxylase
mdlC from *P. putida*
crystal structure
available
UniProt: P20906

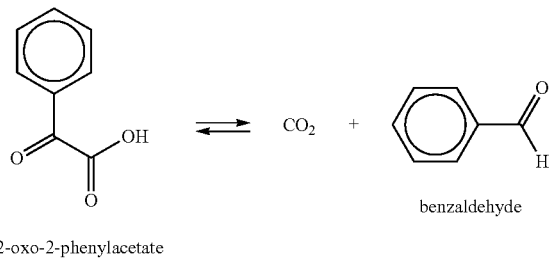

2-oxo-2-phenylacetate benzaldehyde 4.1.1.75
2-ketoarginine
decarboxylase
aruI; *P. aeruginosa*
NCBI AAG08362

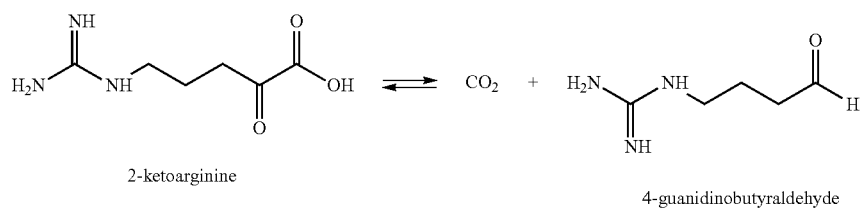 [SMILES: N=C(N)NCCCC(=O)C(=O)O ; "CO2" ; N=C(N)NCCCC=O]

2-ketoarginine 4-guanidinobutyraldehyde 4.1.1.82
Phosphonopyruvate
decarboxylase
fom2; *Streptomyces
wedmorensis*
UniProt: Q56190
NCBI AB016934

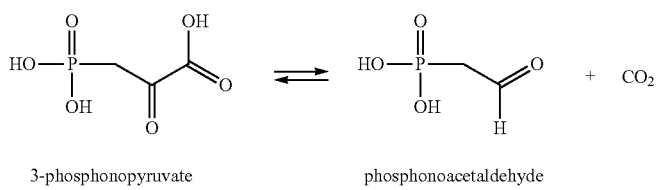

3-phosphonopyruvate phosphonoacetaldehyde 4.1.1.80
Pyruvate decarboxylase
isozyme
PDC6, PDC1; *S.
cerevisiae*
PDC1 crystal structure
available
PDC1 UniProt: P06169
PDC6 UniProt: P26263

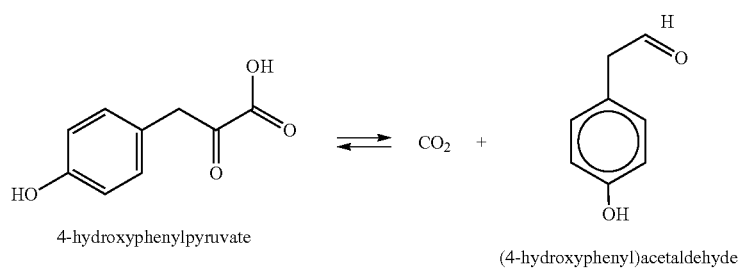

4-hydroxyphenylpyruvate (4-hydroxyphenyl)acetaldehyde 4.1.1.1
Pyruvate decarboxylase
isozyme 2
PDC5, *S. cerevisiae*
(also, PDC1, PDC6,
Aro10, KivD)
UniProt: P16467

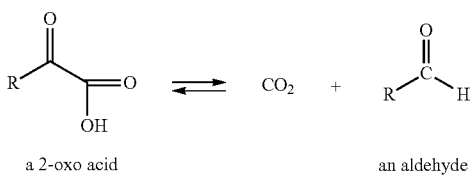

a 2-oxo acid an aldehyde 4.1.1.74
Indolepyruvate
decarboxylase
ipdC; *Pantoea
aggomerans*
ipdC; *Enterobacter
cloacae*
P.a. UniProt P71323
E.c. UniProt P23234

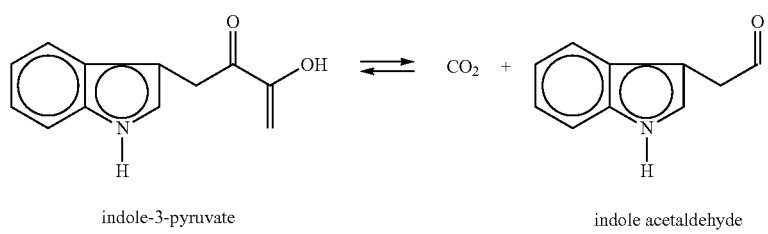

indole-3-pyruvate indole acetaldehyde 4.1.174
Indolepyruvate
decarboxylase
ipdC; *Pantoea
agglomerans*
ipdC; *Enterobacter
cloacae*
P.a. UniProt P71323
E.c. UniProt Q47305

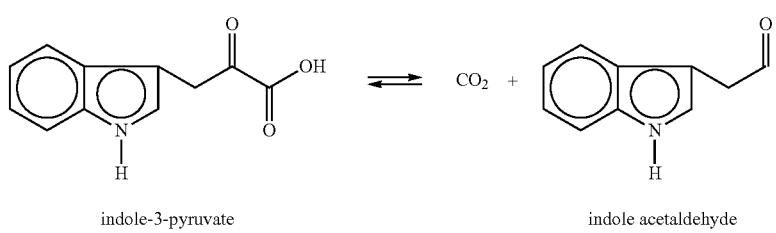

indole-3-pyruvate indole acetaldehyde

TABLE 10-continued

| | | | | |
|---|---|---|---|---|
| 4.1.1.40<br>hydroxypyruvate<br>decarboxylase<br>gene unknown | 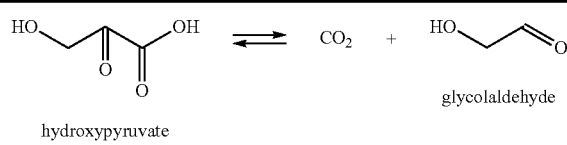<br>hydroxypyruvate | ⇌ | $CO_2$ + | HO⌒CHO<br>glycolaldehyde |

Alcohol dehydrogenases (ADHs) (EC 1.1.1.1 and 1.1.1.2) catalyze the reversible reduction of ketones and aldehydes to alcohols with the reduction of NAD+ to NADH. In some embodiments, examples of alcohol dehydrogenases include, but are not limited to, adhA or adhB (from *Z. mobilis*), butanol dehydrogenase (from *Clostridium acetobutylicum*), propanediol oxidoreductase (from *E. coli*), ADHIV alcohol dehydrogenase (from *Saccharomyces*), and ADH6 (from *S. cerevisiae*). Aldehyde NAD(+) dehydrogenase activity and alcohol NAD(+) dehydrogenase activities can be carried out by two different polypeptides, or carried out by a single polypeptide, such as a multi-functional aldehyde-alcohol dehydrogenase (EC 1.2.1.10) from *E. coli* (Goodlove et al. Gene 85:209-14, 1989; GenBank Accession No. M33504). Polypeptides having aldehyde dehydrogenase (NAD(P)+) (EC 1.2.1.-) or aldehyde dehydrogenase (NAD(+)) (EC 1.2.1.3) activity can be used in combination with an alcohol dehydrogenase to reduce the remaining carboxylic acid to an alcohol, yielding a diol. Nucleic acids encoding such polypeptides can be obtained from various species including, without limitation, *S. cerevisiae*.

In another embodiment, α-ketoadipate semialdehyde is converted to ketoadipate by an aldehyde dehydrogenase including, but not limited to, acetaldehyde dehydrogenase (EC 1.2.1.4 encoded by aldB (*Escherichia coli* K12), ALD6 (*Saccharomyces cerevisiae* S288C), aldehyde dehydrogenase (EC 1.2.1.3, ALD3 (*Saccharomyces cerevisiae* S288C), ALD2 (*Saccharomyces cerevisiae* S288C), ALD4 (*Saccharomyces cerevisiae* S288C), ALD5 (*Saccharomyces cerevisiae* S288C), ALDH2 (*Homo sapiens*), alkH (*Pseudomonas oleovorans*), Glycolaldehyde dehydrogenase (EC 1.2.1.21, aldA (*Escherichia coli* K12)), aldA (*Escherichia coli* K12)), L-lactaldehyde dehydrogenase (EC 1.2.1.22, MJ1411 (*Methanocaldococcus jannaschii*), alkH (*Pseudomonas oleovorans*), ALDH2 (*Homo sapiens*), ALD5 (*Saccharomyces cerevisiae* S288C), ALD4 (*Saccharomyces cerevisiae* S288C), ALD2 (*Saccharomyces cerevisiae* S288C), and ALD3 (*Saccharomyces cerevisiae* S288C)).

As illustrated in FIG. 7, enzymatic step 7h, 2-ketoadipate is then converted to glutarate semialdehyde by a keto-decarboxylase listed in Table 10 and then to 5-hydroxypentanoic acid by an alcohol dehydrogenase.

Figure 8:
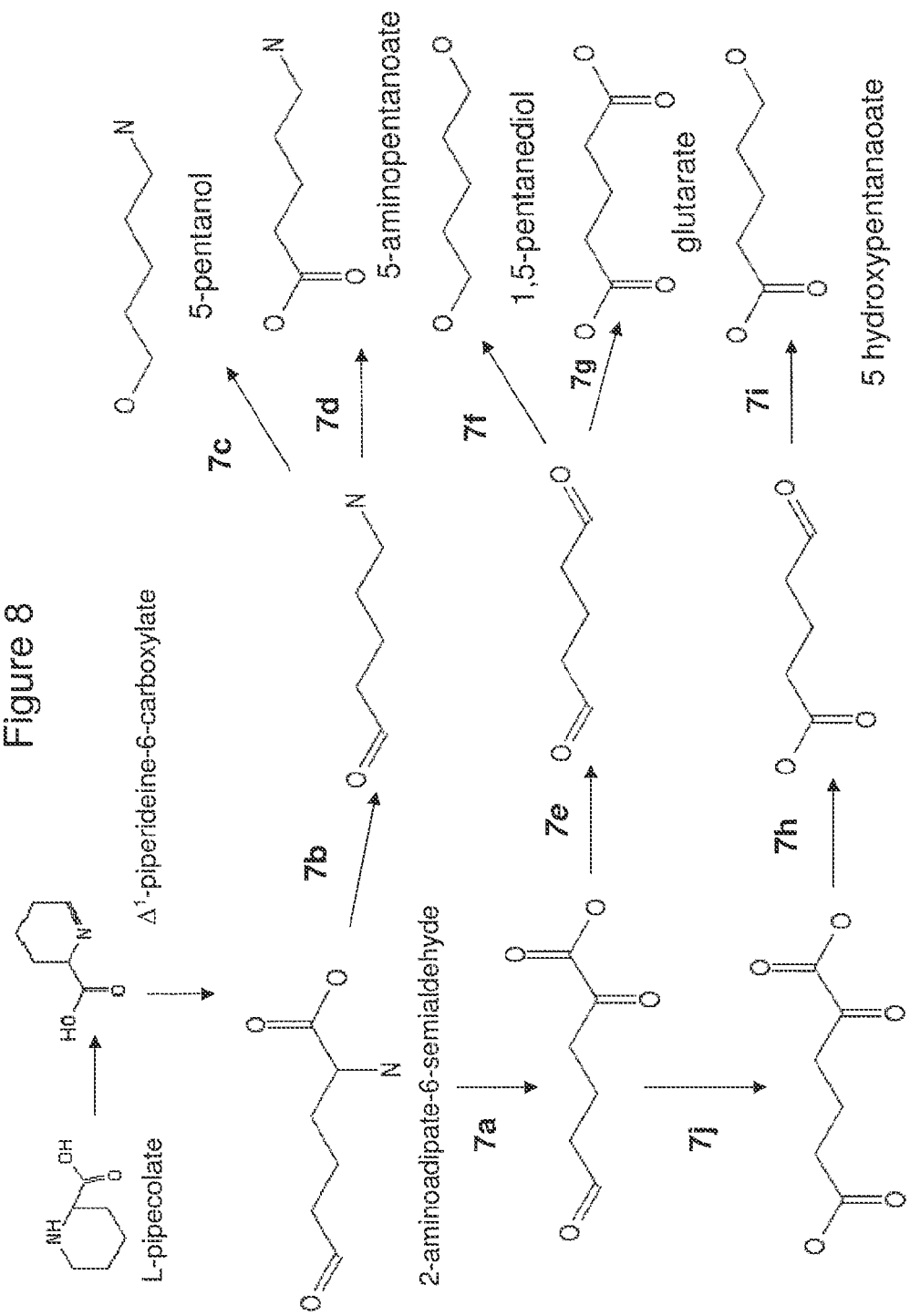
FIG. 8 represents a flow diagram for the bioproduction of C5 difunctional alkanes from L-pipecolate.

B. Engineered Pathways for the Bioproduction of C5 Difunctional Alkanes from Nitrogen-Containing Heterocyclic Ring Aspects of the invention relate to the bioproduction of C5 difunctional alkanes from nitrogen-containing heterocyclic ring (FIG. 8). One should appreciate that 2-aminoadipate semialdehyde can be generated from, for example, L-pipecolate as discussed in the bioproduction of C6 difunctional alkanes. 2-aminoadipate semialdehyde can then be converted to C5 difunctional alkane as disclosed above. One should appreciate that enzymes catalyzing enzymatic steps 5b may also catalyze enzymatic step 7a; and enzymes catalyzing enzymatic step 5e may also catalyze enzymatic step 7j.

Figure 9:
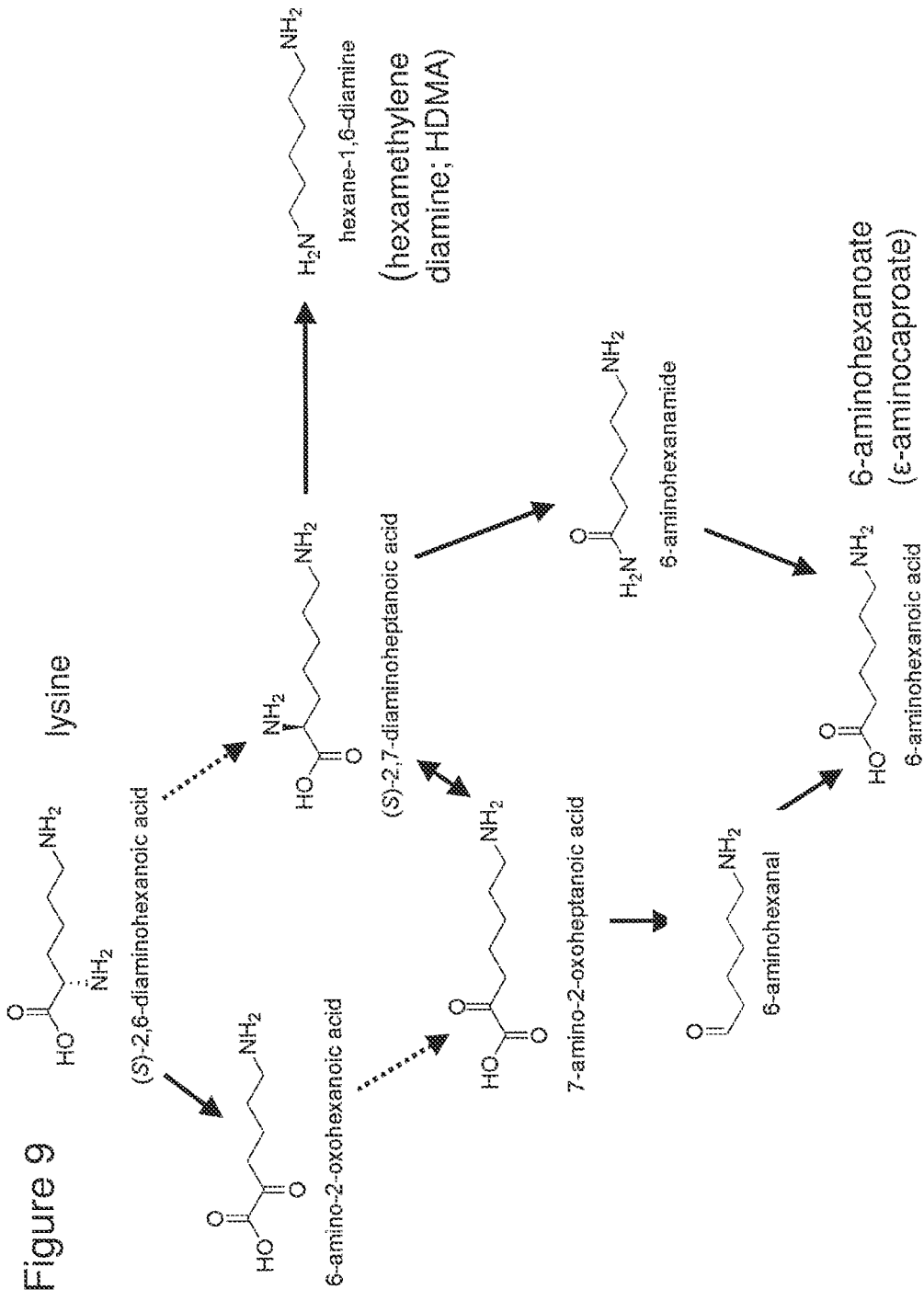
FIG. 9 represents a flow diagram for the bioproduction of C6 difunctional alkanes from lysine via a carbon extension process.

III. Engineered Pathways for the Production of 6-Aminocaproic Acid and Hexamethylenediamine from Lysine Via Carbon Extension Aspects of the invention relate to the bioproduction of C6 difunctional alkanes from lysine with C7 difunctional alkane intermediates (FIG. 9).

In some embodiments, the carbon chain of lysine is elongated to form a 2,7-diaminoheptanoic acid. In some embodiments, the carbon chain of lysine is elongated following a pathway similar to the α-keto-elongation pathway. The α-keto-elongation pathway comprises three enzymes: an homocitrate synthase, an homoaconitase and a homo-isocitrate dehydrogenase. One would appreciate that the lysine biosynthesis pathway IV provides enzymes for the elongation of 2-ketoglutarate to α-ketoadipate. For example, 2-ketoglutarate is converted to homocitrate by a homocitrate synthase (EC 2.3.3.14, LYS20 and LYS21 (*Sacharomyces cerevisiae*), nifV (*Klebsiella pneumoniae*), hcs (*Thermus thermophilus*)). Homocitrate is then converted to cis-homoaconitate and then to homoisocitrate by a homoaconitase (EC 4.2.1.36, LYS4 (*Sacharomyces cerevisiae*), lysU, lysT (*Thermus thermophilus*)) and homoisocitrate is converted to α-ketoadipate by a homo-isocitrate dehydrogenase (EC 1.1.1.87, LYS12 (*Sacharomyces cerevisiae*), hicdh (*Thermus thermophilus*)).

In an engineered pathway for the bioproduction of hexamethylenediamine, 2,7-diaminoheptanoic acid is converted to hexamethylenediamine in a single enzymatic step catalyzed by a decarboxylase. In a preferred embodiment, the decarboxylase is lysine decarboxylase. Lysine decarboxylases (EC 4.1.1.18) isolated from *Escherichia coli* having lysine decarboxylase activity are the cadA gene product and the ldc gene product. Other decarboxylases capable of catalyzing the substrate to product reaction are listed in Table 9.

In some embodiments, a 2,7-diaminoheptanoic acid is converted to 7-amino-2-oxoheptanoic acid by an aminotransferase enzyme (EC 2.6.1.x) or a dehydrogenase (EC 1.4.1.x or EC 1.4.3.x). Preferred enzymes are listed in Table 7 and may be engineered to catalyze the desired substrate to product reaction.

In an alternative embodiment, lysine is first converted to 6-amino-2-oxohexanoic acid by an aminotransferase enzyme (EC 2.6.1.x) or a dehydrogenase (EC 1.4.1.x or EC 1.4.3.x). Preferred enzymes are listed in Table 7 and may be engineered to catalyze the desired substrate to product reaction. In a subsequent step, 6-amino-2-oxohexanoic acid is subjected to a carbon elongation enzymatic step to produce 7-amino-2-oxoheptanoic acid.

In a subsequent step, 7-amino-2-oxoheptanoic acid is converted to 6-aminohexanal by a decarboxylase. Preferred decarboxylases are lysine decarboxylases (EC 4.1.1.18). However, in some embodiments, the 7-amino-2-oxoheptanoic acid to 6-aminohexanal conversion is catalyzed by an enzyme listed in Table 9. 6-aminohexanal is subsequently converted to 6-aminocaproic acid by an aldehyde dehydrogenase (EC 1.2.1.3) or aldehyde oxidase (EC 1.2.3.1, AAO2 (*Arabidopsis thaliana* col), AAO1 (*Arabidopsis thaliana* col), AOX1 (*Homo sapiens*)).

Yet, in another embodiment, 2,7-diaminoheptanoic acid is converted to 6-aminohexamide by a monooxygenase. Preferred monooxygenase is a L-lysine monooxygenase (EC 1.13.12.12, davB in *Pseudomonas fluorescens*) that catalyses the conversion of L-lysine to 5-aminopentamide in the lysine degradation IV pathway. In a subsequent step, 6-aminohexamide is converted to 6-aminocaproic acid by an amidase. In one embodiment, the amidase is a δ-aminovaleramidase (EC 3.5.1.30, davA (*Pseudomonas putida*)) that catalyses the conversion of 5-aminopentanamide to 5-aminopentanoate in the lysine degradation IV pathway.

III. Culture Conditions and Screening Techniques

Microorganisms may be cultivated continuously or discontinuously in a batch process (batch cultivation) or in a fed-batch process (feed process) or repeated fed-batch process (repetitive feed process) for the purposes of di functional alkanes.

The culture medium to be used must satisfy in a suitable manner the requirements of the respective strains. Descriptions of culture media for various microorganisms are contained in the handbook "Manual of Methods for General Bacteriology" of the American Society for Bacteriology (Washington D.C., USA, 1981). Media must contain suitable carbon sources such as monosaccharides (e.g. glucose and fructose), oligosaccharides (e.g. sucrose, lactose), polysaccharides (e.g. starch and cellulose), oils and fats or mixture thereof. Media must contain a nitrogen source such as organic nitrogen-containing compounds such as peptones, yeast extract, meat extract, malt extract, corn steep liquor, soy bean flour and urea, or inorganic compounds such as ammonium sulfate, ammonium chloride, ammonium phosphate, ammonium carbonate and ammonium nitrate. The nitrogen sources may be used individually or as a mixture.

In addition to the carbon sources and nitrogen sources, media must contain suitable minerals, salts, cofactors, buffers and other components, known to those skilled in the art, suitable for growth of the culture and promotion of the enzymatic pathways for C5 and C6 difunctional alkanes.

Typically cells are grown at a temperature in the range of 20° C. to about 45° C. and preferably 25° C. to 40° C. in an appropriate medium. Suitable growth media includes common commercially available media such as Luria Bertani (LB) broth, Yeast medium (YM) or any synthetic or defined media. Suitable pH ranges are between pH 5.0 to pH 9.0. In order to regulate the pH of the culture, basic compounds such as sodium hydroxide, potassium hydroxide, ammonia or ammonia water, or acidic compounds such as phosphoric acid or sulfuric acid are used as appropriate. Culture may be performed under aerobic or anaerobic conditions.

Screening Techniques

In accordance with the methods described herein, reaction mixtures for pathway development may be carried out in any vessel that permits cell growth and/or incubation. For example, a reaction mixture may be a bioreactor, a cell culture flask or plate, a multiwell plate (e.g., a 96, 384, 1056 well microtiter plates, etc.), a culture flask, a fermentor, or other vessel for cell growth or incubation.

Screening may be carried out by detection of expression of a selectable marker, which, in some genetic circumstances, allows cells expressing the marker to survive while other cells die (or vice versa). Efficient screening techniques are needed to provide efficient development of novel pathways using the methods described herein. Preferably, suitable screening techniques for compounds produced by the enzymatic pathways allow for a rapid and sensitive screen for the properties of interest. Visual (colorimetric) assays are optimal in this regard, and are easily applied for compounds with suitable light absorption properties. More sophisticated screening technologies include, for instance, high-throughput HPLC-MS analysis, SPME (Solid Phase Microextraction) and GC-MS (Gas chromatography-mass spectrometry) (see Handbook of analytical derivatization reaction, D. R. Knapp; John Wiley & Sons, 1979). In some instance, screening robots are connected to HPLC-MS systems for automated injection and rapid sample analysis. These techniques allow for high-throughput detection and quantification of virtually any desired compound.

Biologically produced products of interest may be isolated from the fermentation medium or cell extract using methods known in the art. For example, solids or cell debris may be removed by centrifugation, filtration, decantation and the like. Bioproducts of interest may be isolated by distillation, liquid-liquid extraction, membrane evaporation, adsorption, or using any methods known in the art.

In some embodiments, identification of the product of interest may be performed using an HPLC. For example, the standard samples are prepared with known amounts of the organic product in the medium (e.g. adipic acid, amino caproic acid). The retention time of the adipic acid produced can then be compared to that of the authentic standard. In some embodiments, identification of the product of interest may be performed using a GC-MS. The resolved samples are then analyzed by a mass selective detector and compared to previous mass spectra and retention time of authentic standards.

In some embodiments, cellular extracts may be screened for enzyme activity. For example, oxohexanoate dehydrogenase activity may be detected by measuring the rate of increase of absorbance at 340 nm as described in Donoghue and Trudgill (Eur. J. Biochem., 1975, 60:1-7).

The practice of the present methods will employ, unless otherwise indicated, conventional techniques of cell biology, cell culture, molecular biology, transgenic biology, microbiology, recombinant DNA, and immunology, engineering, robotics, optics, computer software and integration. The techniques and procedures are generally performed according to conventional methods in the art and various general references. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. 1. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986); Lakowicz, J. R. Principles of Fluorescence Spectroscopy, New York:Plenum Press (1983), and Lakowicz, J. R. Emerging Applications of Fluorescence Spectroscopy to Cellular Imaging: Lifetime Imaging, Metal-ligand Probes, Multi-photon Excitation and Light Quenching, Scanning Microsc. Suppl. VOL. 10 (1996) pages 213-24, for fluorescent techniques, Optics Guide 5 Melles Griot® Irvine Calif. for general optical methods, Optical Waveguide Theory, Snyder & Love, published by Chapman & Hall, and Fiber Optics Devices and Systems by Peter Cheo, published by Prentice-Hall for fiber optic theory and materials.

EQUIVALENTS

The present invention provides among other things compositions and methods for metabolic engineering. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

We claim:

1. A recombinant host cell producing hexamethylenediamine, the recombinant host cell comprising at least one recombinant nucleic acid encoding a polypeptide that catalyzes the conversion of lysine to 2,6-diaminohexanal.

2. The recombinant host cell of claim 1 wherein the polypeptide is an amino aldehyde dehydrogenase.

3. The recombinant host cell of claim 1 wherein the at least one recombinant nucleic acid encodes a second polypeptide that catalyzes the conversion of 2,6-diaminohexanal to 2-oxo-1,6-diaminohexane.

4. The recombinant host cell of claim 3 wherein the second polypeptide is a semialdehyde aminomutase.

5. The recombinant host cell of claim 4 wherein the polypeptide is glutamate-1-semialdehyde 2,1-aminomutase.

6. The recombinant host cell of claim 5 wherein the glutamate-1-semialdehyde 2,1-aminomutase is from *Escherichia coli, Synechococcus* sp, *Xanthomonas campestris*, or *Propionibacterium freudenreichii*.

7. The recombinant host cell of claim 5 wherein the glutamate-1-semialdehyde 2,1-aminomutase is encoded by hemL or GSA1.

8. The recombinant host cell of claim 3 wherein the at least one recombinant nucleic acid encodes a third polypeptide that catalyzes the conversion of 2-oxo-1,6-diaminohexane to hexamethylenediamine.

9. The recombinant host cell of claim 3 wherein the at least one recombinant nucleic acid encodes a third polypeptide that catalyzes the conversion of 2-oxo-1,6-diaminohexane to 2-hydroxy-1,6-diaminohexane.

10. The recombinant host cell of claim 9 wherein the fourth polypeptide is an alcohol dehydrogenase.

11. The recombinant host cell of claim 9 wherein the at least one recombinant nucleic acid encodes a fourth polypeptide that catalyzes the conversion of 2-hydroxy-1,6-diaminohexane to 1,6-diamino-hexene.

12. The recombinant host cell of claim 11 wherein the at least one recombinant nucleic acid encodes a fifth polypeptide that catalyzes the conversion of 1,6-diamino-hexene to hexamethylenediamine.

13. The recombinant host cell of claim 1 wherein the host cell is a prokaryotic cell.

14. The recombinant host cell of claim 1 wherein the host cell is a eukaryotic cell.

15. The recombinant host cell of claim 13 wherein the host cell is *E. coli, C. glutanicum, B. flavum* or *B. lactofermentum*.

16. The recombinant host cell of claim 8 expressing three or more polypeptides and wherein the polypeptides are encoded by a single nucleic acid molecule.

17. The recombinant host cell of claim 8 expressing three or more polypeptides and wherein each polypeptide is encoded by a different nucleic acid molecule.

18. The recombinant host cell of claim 1 wherein the at least one recombinant nucleic acid comprises an engineered nucleic acid having less than 95% identity with a natural nucleic acid.

19. A method of producing hexamethylenediamine, the method comprising:
    culturing a recombinant host cell, the recombinant host cell comprising at least one recombinant nucleic acid encoding a polypeptide that catalyzes the conversion of lysine to 2,6-diaminohexanal; and
    isolating the hexamethylenediamine.

20. The method of claim 19 wherein the at least one recombinant nucleic acid encodes a second polypeptide that catalyzes the conversion of 2,6-diaminohexanal to 2-oxo-1,6-diaminohexane.

* * * * *